United States Patent
Liu et al.

(10) Patent No.: US 12,286,485 B2
(45) Date of Patent: Apr. 29, 2025

(54) ANTI-CD24 COMPOSITIONS AND USES THEREOF

(71) Applicants: ONCOC4, INC., Rockville, MD (US); CHILDREN'S RESEARCH INSTITUTE, CHILDREN'S NATIONAL MEDICAL CENTER, Washington, DC (US)

(72) Inventors: Yang Liu, Baltimore, MD (US); Pan Zheng, Baltimore, MD (US); Rhonda Flores, Washington, DC (US); Hung-Yen Chou, McLean, VA (US); Zhihong Xue, Falls Church, VA (US); Peiying Ye, Potomac, MD (US); Martin Devenport, Gaithersburg, MD (US)

(73) Assignees: OncoC4, Inc., Rockville, MD (US); Children's Research Institute, Children's National Medical Center, Washington, DC (US)

( * ) Notice: Subject to any disclaimer, the term of this patent is extended or adjusted under 35 U.S.C. 154(b) by 1200 days.

(21) Appl. No.: 17/055,248

(22) PCT Filed: May 13, 2019

(86) PCT No.: PCT/US2019/031983
§ 371 (c)(1),
(2) Date: Jun. 8, 2021

(87) PCT Pub. No.: WO2019/222082
PCT Pub. Date: Nov. 21, 2019

(65) Prior Publication Data
US 2021/0214458 A1    Jul. 15, 2021

Related U.S. Application Data

(60) Provisional application No. 62/671,193, filed on May 14, 2018.

(51) Int. Cl.
*C07K 16/28* (2006.01)
*A61K 39/00* (2006.01)
*A61P 35/00* (2006.01)

(52) U.S. Cl.
CPC ...... *C07K 16/2896* (2013.01); *A61K 39/4611* (2023.05); *A61K 39/4631* (2023.05); *A61K 39/464429* (2023.05); *A61P 35/00* (2018.01); *C07K 16/2809* (2013.01); *A61K 2039/505* (2013.01); *A61K 2239/13* (2023.05); *A61K 2239/46* (2023.05); *C07K 2317/31* (2013.01); *C07K 2317/732* (2013.01)

(58) Field of Classification Search
CPC ............ C07K 16/2896; C07K 2317/52; C07K 2317/64; C07K 2317/56; A61K 2239/13; A61K 2039/505; A61K 47/6849; G01N 2333/70596
See application file for complete search history.

(56) References Cited

U.S. PATENT DOCUMENTS

| | | | |
|---|---|---|---|
| 2006/0167232 | A1 | 7/2006 | Aburatani et al. |
| 2015/0284475 | A1 | 10/2015 | Zhou et al. |
| 2016/0231328 | A1 | 8/2016 | Krishna et al. |
| 2016/0244526 | A1 | 8/2016 | Igawa et al. |
| 2017/0224818 | A1 | 8/2017 | Lindhofer et al. |

FOREIGN PATENT DOCUMENTS

| | | |
|---|---|---|
| CN | 1894413 A | 1/2007 |
| CN | 103819561 A | 5/2014 |
| WO | 2009063461 A1 | 5/2009 |
| WO | 2015058048 A | 4/2015 |
| WO | 2017125897 A1 | 7/2017 |
| WO | 2013045112 A1 | 4/2023 |

OTHER PUBLICATIONS

Kay et al., J of Immunology 147(4):1412-1416 (Year: 1991).*
Japanese Office Action for JP Application No. 2023-093016, dated May 15, 2024, 5 pages.
Canadian Office Action for CA Application No. 3,089,768, mailed on Jun. 4, 2024, 7 pages.
Chinese Office Action for CN Application No. 201980010939.7, mailed May 25, 2024, 5 pages.
Mexican Office Action for MX Application No. MX/a/2020/012091, mailed Jun. 7, 2024, 26 pages.
Igawa, et al., "pH-dependent antigen-binding antibodies as a novel therapeutic modality," Biochimica et Biophysica Acta, vol. 1844, No. 11, pp. 1943-1950, Aug. 12, 2014.
M C Salamone et al. Antibodies recognizing CD24 LAP epitope on human T cells enhances CD28 and IL-2 T cell proliferation, Feb. 2001, "J Leukoc Biol", vol. 69, Issue 02, pp. 215 to 223.
Amit Maliar et al. Redirected T cells that target pancreatic adenocarcinoma antigens eliminate tumors and metastases in mice, Jun. 2012, "Gastroenterology", vol. 143, Issue 05, pp. 1375 to 1384.
"Shiran Shapira et al. An Immunoconjugate of anti-CD24 and Pseudomonas exotoxin selectively kills human colorectal tumors in mice," Mar. 2011, "Gastroenterology", vol. 140, Issue 03, pp. 935 to 946.
Fumou Sun et al. Engineering a high-affinity humanized anti-CD24 antibody to target hepatocellular carcinoma by a novel CDR grafting design. Oncotarget. 8(31). Apr. 19, 2017. 51238-51252. (Entire Document).

(Continued)

*Primary Examiner* — Jeffrey Stucker
*Assistant Examiner* — Sarah Cooper Patterson
(74) *Attorney, Agent, or Firm* — Ron Galant; POLSINELLI PC

(57) ABSTRACT

Provided herein are anti-CD24 antibodies that selectively bind human CD24 expressed in cancer cells, but not human CD24 expressed in non-cancerous cells, and the use of such antibodies in cancer therapy.

13 Claims, 34 Drawing Sheets
Specification includes a Sequence Listing.

(56) References Cited

OTHER PUBLICATIONS

"Yang. et al., Attenuated Listeria Monocytogenes as cancer vaccine vector for the delivery of CD24, abiomarker for hepatic cancer stem cells." Cell Mol Immunol.Mar. 2014;11(2): 184-96.

Kim K.H. et al., Enhanced CD24 expression in endometrial carcinoma and its expression pattern in normal and hyperplastic endometrium. Histol Histopathol. Mar. 2009; 24(3):309-16.

Office Action for Chinese Application No. 20980032893.9, issued on Aug. 17, 2022, 18 Pages (10 Pages of Official Copy and 08 Pages of English Translation).

Office Action for Taiwan Application No. 108116423, issued on May 25, 2023, 10 Pages (05 Pages of Official Copy and 05 Pages of English Translation).

Office Action for Eurasian Application No. 202092306, issued Nov. 18, 2022 (45 Pages).

Office Action for Canadian Application No. 3,099,554, issued Sep. 13, 2023 (4 Pages).

Weber, et al., "Antibodies to the protein core of the small cell lung cancer workshop antigen cluster-w4 and to the eucocyte workshop antigen cluster-w4 and to the leucocyte workshop antigen CD24 recognize the same short protein sequence leucine-alanine-proline"; Clin Exp Immunol, Aug. 1993, vol. 93, No. 2, pp. 279-285.

Tsubokawa et al., "The monoclonal antibody HCM31 specifically recognizes the Sd(a) tetrasaccharide in goblet cell mucin"; FEBS Open Bio, Jul. 20, 2012, vol. 2, pp. 223-233.

International Search Report and Written Opinion mailed Oct. 16, 2019 in corresponding International Patent Application No. PCT/US2019/031983.

Barkal, A et al., "CD24 signalling through macrophage Siglec-10 is a new target for cancer immunotherapy," Nature, 572(7769), pp. 392-396 (2019).

Panagiotou, E et al., "CD24: A Novel Target for Cancer Immunotherapy," Journal of Personalized Medicine, 12, 1235, pp. 1-15 (2022).

Li, S et al., "IMM47, a humanized monoclonal antibody that targets CD24, exhibits exceptional anti-tumor efficacy by blocking the CD24/Siglec-10 interaction and can be used as monotherapy or in combination with anti-PD1 antibodies for cancer immunotherapy," Antibody Therapeutics, vol. 6, No. 4, pp. 240-252 (2023).

Maliar A., et al., "Redirected T cells that target pancreatic adenocarcinoma antigens eliminate tumors and metastases in mice," Gastroenterology Nov. 2012;143(5):1375-1384.e5. doi: 10.1053/j.gastro.2012.07.017. Epub Jul. 20, 2012.

First Exam Report for New Zealand Patent Application No. 769355, issued on Aug. 13, 2024, 3 pages.

Office Action for Korean Patent Application No. 10-2020-7033131, issued on Sep. 12, 2024, 11 pages.

* cited by examiner

3B6 DAPI

Mapping 3B6 binding site through peptide inhibition

ANTI-CD24 COMPOSITIONS AND USES THEREOF

FIELD OF THE INVENTION

The disclosure relates to anti-CD24 antibodies that selectively bind human CD24 expressed in cancer cells but not human CD24 expressed in non-cancerous cells. The disclosure also relates to the use of such antibodies in cancer therapy.

BACKGROUND OF THE INVENTION

CD24 is a small heavily glycosylated mucin-like glycosylphosphatidyl-inositol (GPI) linked cell surface protein. CD24 is expressed at higher levels on hematopoietic cell, including B cells, T cells, neutrophils, eosinophils, dendritic cells, and macrophages, as well as non-hematopoietic cells, including neural cells, ganglion cells, epithelia cells, keratinocytes, muscle cells, pancreatic cells, and epithelial stem cells. In general, CD24 tends to be expressed at higher levels in progenitor cells and metabolically active cells and to a lesser extend in terminally differentiated cells. The function of CD24 is unclear in most cell types, but diverse immunological functions of CD24 have been reported.

Although CD24 is found in many normal tissues and cell types, CD24 is overexpressed in nearly 70% of human cancers. High levels of CD24 expression detected by immunohistochemistry have been found in epithelial ovarian cancer (83%), breast cancer (85%), non-small cell lung cancer (45%), prostate cancer (48%) and pancreatic cancer (72%). CD24 is one of the most overexpressed proteins in cancer cells. CD24 expression is upregulated during tumorigenesis, suggesting its role in tumor progression and metastasis. Overexpression of CD24 in cancer has also been identified as a marker indicative of poor prognosis and a more aggressive course of the disease for cancer patients. In breast cancer, expression of CD24 is significantly higher in invasive carcinoma than benign or precancerous lesions. In non-small cell lung cancer, CD24 expression has been identified as an independent marker for the overall survival of the patient. Furthermore, in esophageal squamous cell carcinoma, CD24 overexpression is suggestive of tumor lymph node metastasis, poor tumor grade as well as reduced survival time. Similar observations were found in many other cancers including colon cancer, hepatocellular carcinoma, glioma, ovarian cancer, and prostate cancer. While CD24 has been heavily used as a prognosis marker for cancer, it has not been utilized as a neoantigen that can be a potential target for cancer therapy due to its expression on normal cell types and potential toxicity.

Mature CD24 is a small highly glycosylated sialoglycoprotein of 31 amino acids with 16 potential O-glycosylation sites and 2 predicted N-glycosylation sites. Glycosylation is one of the most complex post-translational modifications of proteins. A shift from the normal glycosylation pathway occurs is known to occur in many cancer cells, leading to altered glycan expression and resulting in hyper-glycosylation or hypo-glycosylation of many cellular proteins. The altered glycosylation patterns found in cancer cells are the result of many contributory factors including dysregulation at the transcriptional level, dysregulation of chaperone proteins during glycosylation, and altered glycosidase and glycotransferase activities. Tumor-associated glycan changes include longer or shorter branching of N-glycans, higher or lower density of O-glycans, generation of truncated version of normal counterparts (Tn, sTn, and T antigens), and generation of unusual forms of terminal structures with sialic acid and fucose (sLea and sLex epitopes).

Accordingly, there is a need in the art for improved ways of identifying and treating cancer, in particular for methods and compositions capable of differentiating cancerous from non-cancerous cells.

SUMMARY OF THE INVENTION

Provided herein is a monoclonal anti-CD24 antibody whose binding to CD24 is blocked by glycosylation present in normal cells but not in cancer cells. The antibody thereof may bind to a glycan-shielded epitope that is exposed on cancer cells, but not on non-cancerous cells. The antibody may bind to a peptide comprising the sequence set forth in SEQ ID NO: 48.

In another aspect the monoclonal antibody may bind to cancerous cells with minimal or no reactivity to noncancerous cells.

In another aspect the monoclonal antibody may bind tumor cells with minimal or no reactivity to non-tumor cells.

In another aspect the monoclonal antibody may bind to circulating cancer cells with minimal or no reactivity to haemopoietic cells.

In another aspect the monoclonal antibody cannot bind CD24 on cells lacking cancer-specific glycosylation patterns but can bind CD24 on cells with cancer-specific glycosylation patterns.

In another aspect, a composition, which may be a pharmaceutical composition, comprises the monoclonal antibody, or one or more antigen binding fragments thereof.

In another aspect the composition is used to kill cancer cells through antibody mediated cellular cytotoxicity (ADCC).

In another aspect the composition is used to kill cancer cells through antibody-mediated cellular phagocytosis (ADCP).

In another aspect the composition is used to kill cancer cells through combined ADCC and ADCP.

In another aspect the composition comprises a chimeric antigen receptor T cell, which may be used to confer cancer cell-specificity to T cells.

In another aspect the composition comprises monoclonal antibody 3B6.

In another aspect the composition comprises a monoclonal antibody comprising the sequences set forth in SEQ ID NOS: 1 and 2.

In another aspect the composition comprises monoclonal antibodies derived by affinity maturation of monoclonal antibody 3B6.

In another aspect the composition comprises a monoclonal antibody comprising a heavy chain selected from any one of the sequences set forth in SEQ ID NOS: 3-10.

In another aspect the composition comprises a monoclonal antibody comprising a light chain selected from any one of the sequences set forth in SEQ ID NOS: 11-16.

In another aspect the composition comprises monoclonal antibody PP6373 derived by affinity maturation of monoclonal antibody 3B6.

In another aspect the composition comprises a monoclonal antibody comprising the sequences set forth in SEQ ID NOS: 6 and 16.

In another aspect the composition comprises a monoclonal antibody derived by humanizing monoclonal antibody PP6373.

In another aspect the composition comprises a monoclonal antibody comprising a heavy chain selected from any one of the sequences set forth in SEQ ID NOS: 29-32.

In another aspect the composition comprises a monoclonal antibody comprising a light chain selected from any one of the sequences set forth in SEQ ID NOS: 33-36.

In another aspect the pharmaceutical composition comprises monoclonal antibody H2L3 derived by humanizing monoclonal antibody PP6373.

In another aspect the pharmaceutical composition comprises monoclonal antibody H3L3 derived by humanizing monoclonal antibody PP6373.

In another aspect the composition comprises a monoclonal antibody comprising a heavy chain variable sequence comprising the sequence set forth in SEQ ID NO: 30 and a light chain variable region comprising the sequence set forth in SEQ ID NO: 35.

In another aspect the composition comprises a monoclonal antibody comprising a heavy chain variable region comprising the sequence set forth in SEQ ID NO: 31 and a light chain variable region comprising the sequence set forth in SEQ ID NO: 33.

In another aspect the composition comprises a single chain monoclonal antibody comprising the sequence set forth in SEQ ID NO: 17.

In another aspect the composition comprises a bi-specific antibody comprising a first antibody domain comprising the anti-CD24 antibody or antigen binding fragment thereof, and a second antibody domain comprising a second antibody or antigen binding fragment thereof. The bi-specific antibody may be used to bridge cancer and immune effector T cells in a patient requiring treatment for or prevention of a cancer.

In another aspect the second antibody domain possesses a different binding specificity from the first antibody domain.

In another aspect the second antibody domain attracts immune effector T-cells to the cancer cells.

In another aspect the second antibody or antigen binding fragment thereof binds CD3.

In another aspect the second antibody or antigen binding fragment thereof binds TCR-α chain, TCR-β chain, TCR-γ chain, or TCR-δ chain.

In another aspect the first antibody domain comprises an antibody comprising the sequence set forth in SEQ ID NO: 17 and the second antibody domain comprises the sequence set forth in SEQ ID NO: 18.

In another aspect the first antibody domain comprises an antibody comprising any one of the sequences set forth in SEQ ID NOS: 23-27 and 37-41.

In another aspect the composition comprising a bi-specific antibody may be used to treat cancer cells through antibody-mediated cellular cytotoxicity (ADCC).

In another aspect the composition comprises a bi-specific antibody with enhanced ADCC activity.

In another aspect the composition comprises a bi-specific antibody is used to treat cancer cells through antibody-mediated cellular phagocytosis (ADCP).

In another aspect the composition comprising a bi-specific antibody has enhanced ADCP activity.

In another aspect the composition comprises a chimeric antigen receptor for use in immunotherapy, wherein said receptor comprises a single chain antibody comprising any one of the sequences set forth in SEQ ID NOS: 1-36.

In another aspect the chimeric antigen receptor is used in immunotherapy, wherein said receptor comprises a single chain antibody comprising the sequence set forth in SEQ ID NO: 28.

In another aspect the pharmaceutical composition is used in conjunction with a second anti-cancer therapy.

Provided herein is a method of treating cancer in a patient in need thereof comprising administering any one or more of the antibodies, bi-specific antibodies, chimeric antigen receptors, or compositions described herein to the patient, wherein the cancer is lung cancer, liver, cancer, brain cancer, cervical cancer, ovarian cancer, renal cancer, testicular cancer, prostate cancer, or neuroblastoma. The cancer may bind to an anti-CD24 antibody composition described herein.

Further provided herein is a method of diagnosing a malignant tissue or metastatic lesion by using the anti-CD24 antibody composition. The anti-CD24 antibody composition may bind the malignant tissue or metastatic lesion at a level above a threshold amount, which may be indicative of a malignant tissue or metastatic lesion.

Also provided herein is a method of identifying circulating cancer cells using the anti-CD24 antibody composition. The anti-CD24 antibody composition may bind circulating cancer cells at a level above a threshold amount, which may be indicative of circulating cancer cells. Further provided herein is use of a composition described herein in the manufacture of a medicament for treating a disease or condition described herein.

DESCRIPTION OF THE DRAWINGS

FIG. 2A. Normalized affinity plots of anti-CD24 monoclonal antibodies ML5, 3B6, and SN3 and a control antibody were tested against 6 neuroblastoma cell lines, IMR32, SK-N-SH, SH-SY5Y, SK-N-BE(2), SK-N-AS, and SK-N-BE(2)C. Although 3B6 has some affinity to all the neuroblastoma cell lines except SK-N-AS, the affinity of 3B6 was considerably lower relative to commercially available anti-CD24 antibodies ML5 (BD Bioscience Cat #555426) and SN3 (Thermo Fisher Cat #MA5-11833). FIG. 2B. Fluorograph of 3B6 treatment of 4 medulloblastoma tumors. 3B6 bound 3 of the 4 tumors.

DETAILED DESCRIPTION

Figure 1:
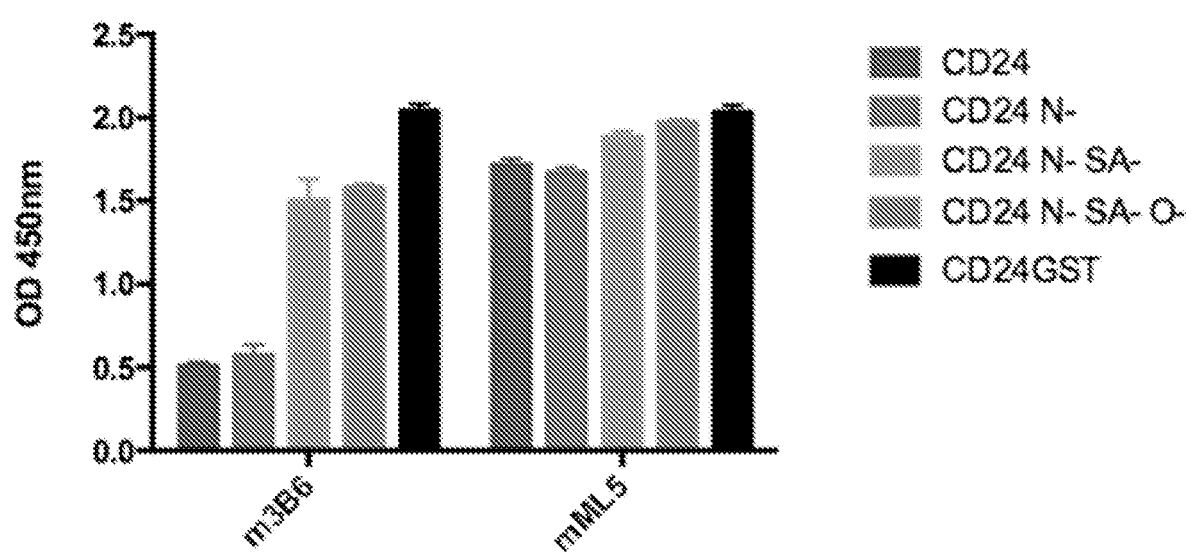
FIG. 1. Bar plot of ELISA results indicating binding of anti-CD24 monoclonal antibody 3B6 is hindered by presence of glycan whereas the commercially available anti-CD24 monoclonal antibody ML5 is not. 3B6 binds strongly to CD24 stripped of N-glycan and sialic acid modifications (N-SA-CD24) and CD24 stripped of N-glycan, sialic acid, and O-glycan modifications (N-SA-O-CD24) but binds very weakly to both CD24 stripped of N-glycan modifications (N-CD24) or fully modified (N-glycan+sialic acid+O-glycan modifications) CD24. CD24GST represents a negative control CD24-GST fusion.

Targeting of cancer expressed epitopes is a widely adopted approach for the treatment of cancer. However, many such epitopes do not make good drug targets because they are also expressed on normal tissues, which can lead to toxicity issues. An ideal Tumor-Specific Antigen (TSA) will have broad expression in cancer but minimal or no expression in essential host organs. Attributes of less ideal but equally workable TSAs are those expressed but differentially modified in normal vs cancer tissues, so-called Tumor-Associated Antigens (TAA). Examples of well characterized tumor antigens are MAGE-A3, MUC-1 and NY-ESO 1.

Identification of novel TSAs and TAAs is a limiting factor in the development of new or more effective cancer therapies, particularly for those cancers where tumor antigens do not currently exist. CD24 is a good cancer target for the following reasons: it is broadly overexpressed in over 70% of all human cancers and is differentially glycosylated in cancer, it appears to be oncogenic and is associated with poor prognoses in various cancers and significantly shorter patient survival, and it is a marker for cancer stem cells which can cause relapse and metastasis by giving rise to new tumors. The inventors have discovered anti-CD24 antibodies whose binding to CD24 is blocked by glycosylation that occurs in normal cells but not cancer cells. As a result, the antibodies bind to cancer cell lines and cancer tissues, but with minimal reactivity to a variety of normal tissues and hematopoietic cells.

Provided herein are antibodies and antigen-binding fragments thereof. The antibody may be a monoclonal antibody, a human antibody, a chimeric antibody or a humanized antibody. The antibody may be monospecific, bispecific, trispecific, or multispecific. The antigen-binding fragment of the antibody may immunospecifically bind to CD24, and in particular human CD24, preferably expressed on the surface of a live cell at an endogenous or transfected concentration. The antigen-binding fragment may bind to CD24. The antibody may be detectably labeled, or may comprise a conjugated toxin, drug, receptor, enzyme, or receptor ligand.

In addition to direct tumor targeting, the immune system has the ability to recognize and eliminate cancers in experimental model systems and in patients. As a result, cancer immunotherapies are emerging as one of the most promising areas of cancer therapy. Active cancer immunotherapies involve agents that amplify natural immune responses (including antibodies against PD-1, PD-L1 or CTLA-4); bispecific molecules such as antibodies that bridge cancer and immune effector T cells; or, adoptive cell transfer (ACT) using ex vivo stimulated tumor infiltrating lymphocytes (TILs), activated natural killer (NK) cells, or genetically-engineered T cells (chimeric antigen receptors (CARs) and T cell receptor (TCR) modified T cells). Many of these technologies require a tumor targeting component for specificity and efficacy.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise. The word "about" in association with a numeric value denotes a reasonable approximation of that value. In certain cases "about" may be construed as being within as much as 10% of the specific value with which it is associated. For example, the phrase "about 100" would encompass any value between 90 and 110.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Treatment" or "treating," when referring to protection of an animal from a disease, means preventing, suppressing, repressing, or completely eliminating the disease. Preventing the disease involves administering a composition of the disclosure to an animal prior to onset of the disease. Suppressing the disease involves administering a composition of the disclosure to an animal after induction of the disease but before its clinical appearance. Repressing the disease involves administering a composition of the disclosure to an animal after clinical appearance of the disease.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelid antibodies, single chain antibodies, disulfide-linked Fvs (sdFv), intrabodies, and anti-idiotypic (anti-Id) antibodies (including, e.g., anti-Id and anti-anti-Id antibodies to antibodies of the invention). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's CDR and optionally the framework residues that comprise the antibody's "variable region"

antigen recognition site, and exhibit an ability to immunospecifically bind antigen. Such fragments include Fab', F(ab')₂, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.).

A "chimeric antibody" is a molecule in which different portions of the antibody are derived from different immunoglobulin molecules such as antibodies having a variable region derived from a non-human antibody and a human immunoglobulin constant region. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089, the contents of each of which are incorporated herein in their entirety), veneering or resurfacing (EP 592,106; EP 519,596, the contents of each of which are incorporated herein by reference), and chain shuffling (U.S. Pat. No. 5,565,332, the contents of which are incorporated herein by reference.

As used herein, the term "humanized antibody" refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. The donor antibody may be referred to as having been "humanized," by the process of "humanization," because the resultant humanized antibody is expected to bind to the same antigen as the donor antibody that provides the CDRs. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

2. Anti-CD24 Antibody Compositions

Described herein is an anti-CD24 antibody that may specifically target a cancer-specific glycoform of CD24. The anti-CD24 antibody may be used to develop cancer-therapies including, but not limited to: antibody-drug conjugates, ADCC-enhanced therapeutic antibodies, bi-specific antibodies, CAR-T therapies and TCR therapies. Specifically, the anti-CD24 antibody or antigen binding fragment thereof may bind to a glycan-shielded epitope that is exposed on cancer cells but not on non-cancerous cells. And in particular, the anti-CD24 antibody or antigen binding fragment thereof may bind to a CD24 peptide comprising the amino acid sequence SNSGLAPN (SEQ ID NO: 48).

The anti-CD24 antibody may be 3B6, which may comprise a heavy chain variable region comprising the sequence set forth in SEQ ID NO: 1 and a light chain variable region comprising the sequence set forth in SEQ ID NO: 2. The anti-CD24 antibody or antigen binding fragment thereof may be an affinity matured version of 3B6, and may comprise a heavy chain variable region comprising any one of the sequences set forth in SEQ ID NOS: 3-10, and a light chain variable region comprising any one of the sequences set forth in SEQ ID NOS: 11-16. The anti-CD24 antibody or antigen binding fragment thereof may be PP6373, which may comprise a heavy chain variable region comprising the sequence set forth in SEQ ID NO: 6, and a light chain variable region comprising the sequence set forth in SEQ ID NO: 16. For therapeutic applications in humans, the anti-CD24 antibody or antigen binding fragment thereof may be a humanized version of PP6373 and may comprise a heavy chain variable region comprising any one of the sequences set forth in SEQ ID NOS: 29-32, and a light chain variable region comprising any one of the sequences set forth in SEQ ID NOS: 33-36. In particular, the humanized the anti-CD24 antibody or antigen binding fragment thereof may be H2L3, which may comprise a heavy chain variable region comprising the sequence set forth in SEQ ID NO: 30, and a light chain variable region comprising the sequence set forth in SEQ ID NO: 35; or may be H3L3, which may comprise a heavy chain variable region comprising the sequence set forth in SEQ ID NO: 31, and a light chain variable region comprising the sequence set forth in SEQ ID NO: 35.

3. Antibody-Drug Conjugate Compositions

A tumor targeting antibody can be used to prevent or limit the growth of tumors directly by affecting the biology of the tumor. For example, the humanized anti-VEGF monoclonal antibody (bevacizumab; Avastin) blocks the growth of tumors by preventing VEGF-induced tumor vascularization. Other tumor targeting antibodies are used to inhibit tumor cell growth or kill cancer cells through modification of the antibody itself. For example, tumor-targeted immunoconjugates consist of an antibody and an effector moiety bonded together by either covalent cross-links or genetic fusion. The effector moiety can be a cytotoxic drug (an antibody-drug conjugate), a protein toxin (an immunotoxin), or a radionuclide (a radioimmunoconjugate). An example of an antibody-drug conjugate is brentuximab vedotin (ADCETRIS®, Seattle Genetics), which consists of the chimeric monoclonal antibody brentuximab (cAC10, which targets the cell-membrane protein CD30) linked to three to five units of the antimitotic agent monomethyl auristatin E (MMAE, reflected by the 'vedotin' in the drug's name).

The anti-CD24 antibody or antigen binding fragment thereof may be included in antibody drug conjugates, immunotoxins, or radioimmunoconjugates. The anti-CD24 targeting component of such compositions may allow specific delivery of the conjugate to the cancer cells and tissues, while limiting exposure of normal cells and tissues and thus preventing off target toxicity.

4. ADCC Antibody Compositions

The anti-CD24 antibody or antigen binding fragment thereof, or an antibody composition comprising one of the foregoing, may be used to stimulate cancer cell death through at least one of antibody-mediated cellular cytotoxicity (ADCC) and antibody-mediated cellular phagocytosis (ADCP). ADCC is an immune defense mechanism whereby a particular set of immune cells (effector cells) of the body actively engage and lyse a target cell (e.g. pathogen). ADCC has been identified as an important cell-mediated innate immune response and functions as the body's first-line of defense against pathogens and acts to limit and contain infections. The ADCC process is designed to kill the antibody-coated target cell through a non-phagocytic process, and is characterized either by the targeted release of cytotoxic granules or by the expression of cell death-inducing molecules. ADCC is typically initiated when specific antibodies (mostly IgG classes) of the host recognize and bind the membrane-surface antigens of the target cells and simultaneously engage the Fc receptors (FcR) on the effector cell surface. The most common effector cells that mediate ADCC are the natural killer (NK) cells, although monocytes, macrophages, neutrophils, eosinophils and dendritic cells are also capable of mediating an ADCC response. Although ADCC is a rather fast response, the efficacy varies depending on the several parameters such as the antigen density on the surface of the target cells and the affinity of the antigen-antibody interaction as well as characteristics of Fc fragments that determines antibody interactions with varies members of Fc receptor family.

Binding of the antibody to the specific cell surface receptors on the target cells, a process called opsonization, is the key event of the ADCC process. The opsonization process attracts phagocytes to the target cell and may initiate phagocytosis. The binding of the antibody Fc region to the FcRs on the phagocytes also facilitates the formation of C3b, a cleaved product of the complement component 3, which is an important protein that initiates the engulfment of the antibody opsonized target cell. The antibody mediated phagocytosis is also often called as antibody-dependent cell-mediated phagocytosis (ADCP). However, for ADCC, the pathogen does not need to be phagocytosed to be destroyed. As noted above, FcR on the surface of cytotoxic effector cells is the key for eliciting ADCC. In humans, the most important FcR classes that are capable of eliciting ADCC are FcγRI (CD64), FcγRIIa and FcγRIIc (CD32), and the FcγRIIIa (CD16). However, the FcγRIIb receptor suppresses ADCC response. Thus the balance between activating and inhibitory signals from the FcγRs is an important determinant for the magnitude of ADCC response. Upon recognition of the target, specialized intracellular granules (also termed secretory lysosomes) are released by the cytotoxic effector cells in a calcium-dependent polarized exocytotic process. Perforin, cytolysin, and granzyme B are the key components that are released from granules. Perforin inserts and forms a pore within the target cell membrane. This process requires calcium. The granzyme B causes fragmentation of the target cell DNA. An example of a therapeutic antibody that works by ADCC is trastuzumab (Herceptin, Genentech). Trastuzumab targets HER2, which is expressed at abnormally high levels in a larger number of breast cancers and are often called HER2 positive breast cancers, and inhibits the growth of HER2-positive breast cancer by inducing ADCC in the host.

Antibodies used for ADCC mediated activity usually require some kind of modification in order to enhance their ADCC activity. There are a number of technologies available for this which typically involves engineering the antibody so that the oligosaccharides in the Fc region of the antibody do not have any fucose sugar units, which improves binding to the FcγIIIa receptor. Afucosylated antibodies exhibit increased antibody-dependent cellular cytotoxicity (ADCC). For example, Biowa's POTELLIGENT® technology uses a FUT8 gene knockout CHO cell line to produce 100% afucosylated antibodies. FUT8 is the only gene coding a1,6-Fucosyltransferase which catalyzes the transfer of Fucose from GDP-Fucose to GlcNAc in a1,6-linkage of complex-type oligosaccharide. Probiogen has developed a CHO line that is engineered to produce lower levels of fucosylated glycans on MAbs, although not through FUT knockout. Probiogen's system introduces a bacterial enzyme that redirects the de-novo fucose synthesis pathway towards a sugar-nucleotide that cannot be metabolized by the cell. As an alternative approach, Seattle Genetics has a proprietary feed system which will produce lower levels of fucosylated glycans on MAbs produced in CHO (and perhaps other) cell lines. Xencor has developed an XmAb Fc domain technology is designed to improve the immune system's elimination of tumor and other pathologic cells. This Fc domain has two amino acid changes, resulting in a 40-fold greater affinity for FcγRIIIa. It also increases affinity for FcγRIIa, with potential for recruitment of other effector cells such as macrophages, which play a role in immunity by engulfing and digesting foreign material.

The anti-CD24 antibody or antigen binding fragment thereof may be incorporated into ADCC-mediated cancer killing antibodies. The anti-CD24 targeting component of such compositions may allow specific delivery targeting of the cancer cells for ADCC-mediated destruction while sparing normal cells and tissues. The ADCC activity of the anti-CD24 antibody or antigen binding fragment thereof may be enhanced by one or more of the modifications described herein.

5. Bi-Specific Antibody Compositions

Further provided herein is a bi-specific antibody that comprises a first antibody domain comprising a first antibody or antigen binding fragment thereof bridged to a second antibody or antigen binding fragment thereof. The first antibody domain may comprise an anti-CD24 antibody or antigen binding fragment thereof described herein, and the second antibody or antigen binding fragment thereof may bind to other immune-stimulating molecules. In a specific embodiment, the second antibody domain comprises an anti-CD3 antibody or antigen binding fragment thereof. In this case, the bi-specific antibody may specifically target tumor cells expressing the cancer-specific glycoform of CD24, while simultaneously binding to CD3 on cytotoxic T cells, thereby attracting the T cells to the tumor site whereby the T cells would infiltrate the tumor and lead to tumor cytotoxicity. Other examples of partner antibodies for use in a bi-specific antibody for the purpose of attracting cytotoxic T cells or other effector cells to the tumor site are known in the art.

The second antibody or antigen binding fragment thereof may target a complementary anti-tumor pathway or mechanism. The second antibody domain may comprise a cancer immunotherapy antibody or antigen binding fragment thereof that amplifies natural immune responses. Examples of such cancer immunotherapy antibodies include anti-PD-1, anti-B7-H1, anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1BB. Such antibodies may be used to treat cancer. The second antibody or antigen binding fragment thereof may bind TCR-α chain, TCR-β chain, TCR-γ chain, or TCR-δ chain.

The bi-specific antibody may comprise the sequences set forth in SEQ ID NOs: 17 and 18, or any one of the sequences set forth in SEQ ID NOs: 23-27 and 37-41.

There are many different bi-specific antibody technologies known in the art. Most of these require that the 2 component antibodies are in a single chain format so that the two parts can be expressed in a single construct. A preferred method is to express the antibodies as a single-chain variable fragment (scFv). Non-limiting examples of bi-specific antibody technologies include BiTE (for Bi-specific T-cell Engager), DART (for Dual-Affinity Re-Targeting), Fabs-in-tandem immunoglobulin (FIT-Ig), and knobs-into-holes. Such bi-specific antibodies comprising the anti-CD24 antibody or antigen binding fragment thereof are specifically contemplated herein.

6. CAR-T Therapy Compositions

Chimeric antigen receptor (CAR) T-cell therapy, or CAR-T therapy, is a type of cellular treatment in which a cancer patient's T cells are genetically modified ex vivo to express a CAR protein so they will attack cancer cells. Specifically, T cells are taken from a patient's blood, which in particular may be the patient's own blood (autologous), and transfected with a gene construct that expresses the recombinant CAR receptor. Large numbers of the CAR T cells are then grown in the laboratory and infused back into the patient where it can target and destroy the patient's cancer cells. The T cells may also be allogeneic from a matched donor or from a universal, or "off-the-shelf," T cell line wherein one or more of the TCR gene and HLA class I loci of the allogeneic T cells are disrupted and the resulting T cells are not capable of recognizing allogeneic antigens.

CAR protein constructs have modular structures typically comprising the following core components: an extracellular single-chain variable fragment (scFv) derived from an antibody, joined to a hinge/spacer peptide and a transmembrane domain, which is further linked to the intracellular T cell signaling domains of the T cell receptor. The scFv is the targeting element and is expressed on the surface of a CAR T cell to confer antigen specificity. The spacer connects the extracellular targeting element to the transmembrane domain and affects CAR function and scFv flexibility. The transmembrane domain traverses the cell membrane, anchors the CAR to the cell surface, and connects the extracellular domain to the intracellular signaling domain, thus impacting expression of the CAR on the cell surface. The costimulatory domain is derived from the intracellular signaling domains of costimulatory proteins, such as CD28 and 4-1BB, that enhance cytokine production. The CD3 zeta domain is derived from the intracellular signaling portion of the T cell receptor, which mediates downstream signaling during T cell activation. Examples of CAR-T therapies include those targeting the B cell surface antigens CD19 (such as JCAR017 and JCAR014 [Juno Therapeutics]), CTL019 (tisagenlecleucel-T (Kymriah™) [Novartis]) and KTE-C19 (axicabtagene ciloleucel (Yescarta®) [Kite Pharma]), and CD22 (JCAR014 [Juno Therapeutics]). Other examples of CAR-T therapies include those targeting L1-CAM (JCAR023 [Juno Therapeutics]), ROR-1 (JCAR024 [Juno Therapeutics]) and MUC16 (JCAR020 [Juno Therapeutics]).

The scFv portion of the CAR is a critical component and it ensures specificity for cancer cells while preventing activity against normal cells, which is associated with off target toxicity. Therefore, the scFv portion is typically derived from the portion of an antibody that recognizes a target protein specifically expressed on cancer cells but much less frequently, or ideally not at all, on other cells and tissues. Accordingly, a scFv fragment derived from any of the anti-CD24 antibodies described herein may be used as a cancer targeting component of a recombinant CAR protein. In particular, the scFv protein may comprise the sequence set forth in SEQ ID NO: 28.

CAR T cells have demonstrated impressive effects against hematologic tumors such as acute lymphoblastic leukemia (ALL), B-cell Acute Lymphoblastic Leukemia, adult myeloid leukemia, (AML), diffuse large B-cell lymphoma (DLBCL), non-Hodgkin Lymphoma (NHL), Chronic Lymphocytic Leukemia (CLL), primary mediastinal B-cell lymphoma (PMBCL), mantle cell lymphoma (MCL), and multiple myeloma (MM). However, CAR-T therapies have demonstrated only limited effects against solid tumors to date. Due to the characteristic expression pattern of CD24 in tumors and normal tissues, data generated using a CD24 CAR-T have demonstrated that the types of cancer that can be targeted include but are not limited to, brain tumors, head and neck cancer, sarcoma, lung cancer, gastrointestinal cancer, breast cancer, testicular cancer, prostate cancer, pancreatic cancer, cervical cancer, ovarian cancer, liver cancer or hematological malignancies.

7. TCR Therapy Compositions

Similar to CAR-T therapy, genetically modified T cell receptor therapy (TCR) is a type of cellular treatment in which a cancer patient's T cells are genetically modified ex vivo to express a modified TCR to improve the ability of T cell receptors to recognize and attack specific antigenic cell antigens when they are infused back into the patient. However, unlike CAR T cells that recognize proteins expressed on the surface, T cell immunotherapies using gene-modified TCRs have been targeted more towards solid tumors. TCRs can recognize tumor-specific proteins on the inside of cells. When tumor-specific proteins are broken into fragments, they show up on the cell surface with another protein called major histocompatibility complex, or MHC. TCRs are engineered to recognize a tumor-specific protein fragment/MHC combination. Examples of targets for TCR modified T cells include those targeting MAGE-A3, such as KITE-718 (Kite Pharma), Wilms tumor antigen 1 (WT-1), such as JTCR016 (Juno Therapeutics), and NY-ESO 1.

The TCR is a heterodimer consisting of two subunits, TCRα and TCRβ. Each subunit contains a constant region that sits next to the T-cell membrane and anchors the receptor to the cell membrane, and a hypervariable region that functions in antigen recognition. Accordingly, a scFv fragment derived from any of the anti-CD24 antibodies described herein may be used as a cancer targeting component of a recombinant TCR protein. In particular, the scFv protein may comprise the sequence set forth in SEQ ID NO: 28.

8. Peptide Compositions

The anti-CD24 antibody described herein, or antigen binding fragment thereof, may bind to a glycan shielded epitope that is exposed on cancer cells but not on non-cancerous cells. Specifically, the anti-CD24 antibody or antigen binding fragment thereof may bind to a CD24 peptide comprising the amino acid sequence SNSGLAPN (SEQ ID NO: 48). Accordingly, peptides comprising the sequence set forth in SEQ ID NO: 48 may be used to neutralize anti-CD24 antibodies that bind to epitopes comprising the core sequence of the sequence set forth in SEQ ID NO: 48. This could be used in anti-drug antibody assays for detecting neutralizing antibodies. Peptides comprising the sequence set forth in SEQ ID NO: 48 may be used to inhibit potential adverse effects associated with antibodies that bind to epitopes comprising the core of the sequence set forth in SEQ ID NO: 48. The peptide may be modified for better stability for in vivo use using methods known in the art, including but not limiting to use of D-amino acids, replacement of 0 with S in one or more peptide-bonds, addition of a fusion sequence to improve solubility or half-life (e.g. albumin fusions). In yet another embodiment, a molecule comprising the sequence set forth in in SEQ ID NO: 48 may be used as a vaccine for treatment and prophylaxis of cancer.

9. Methods of Treatment

The anti-CD24 antibody compositions, or cellular therapies comprising such antibody compositions, described herein may be used to treat or prevent cancer or another abnormal proliferative disease. Provided herein is a method of such use in a patient in need thereof, which may comprise administering the anti-CD24 antibody or an antigen binding fragment thereof, or a pharmaceutical composition comprising the foregoing, to the patient. Such molecules and pharmaceutical compositions may also be used in the manufacture of a medicament for treating or preventing cancer or another abnormal proliferative disease. As used herein, the term "cancer" refers to a neoplasm or tumor resulting from abnormal uncontrolled growth of cells. As used herein, cancer explicitly includes leukemia and lymphomas. The term refers to a disease involving cells that have the potential to metastasize to distal sites. The patient may be a human.

The cancer or other abnormal proliferative disease may be (but is not limited to) one or more of the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkett's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoacanthoma, seminoma, thyroid follicular cancer and teratocarcinoma. It is also contemplated that cancers caused by aberrations in apoptosis would also be treated by the methods and compositions of the invention. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. The cancer may also be sarcoma, melanoma, or leukemia.

The anti-CD24 antibody or antigen binding fragment thereof may be used in combination with one or more other anti-tumor therapies, including but not limited to, current standard and experimental chemotherapies, hormonal therapies, biological therapies, immunotherapies, radiation therapies, or surgery. In some embodiments, the anti-CD24 antibody or antigen binding fragment thereof may be administered in combination with a therapeutically or prophylactically effective amount of one or more agents, therapeutic antibodies or other agents known to those skilled in the art for the treatment and/or prevention of cancer, autoimmune disease, infectious disease or intoxication. Such agents include for example, any of the above-discussed biological response modifiers, cytotoxins, antimetabolites, alkylating agents, antibiotics, or anti-mitotic agents, as well as immunotherapeutics.

The anti-CD24 antibody or antigen binding fragment thereof may be used in combination with one or more anti-tumor immunotherapies. The anti-tumor immunotherapy may involve molecules that disrupt or enhance alternative immunomodulatory pathways (such as TIM3, TIM4, OX40, CD40, GITR, 4-1-BB, B7-H1, PD-1, B7-H3, B7-H4, LIGHT, BTLA, ICOS, CD27 or LAG3) or modulate the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. Specific embodiments include a bi-specific antibody comprising the anti-CD24 antibody or antibody binding fragment thereof and anti-PD-1 (pembrolizumab (Keytruda®) or nivolumab (Opdivo®)), anti-B7-H1

(atezolizumab (Tecentriq®) or durvalumab), anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1BB. In yet another embodiment, the anti-CD24 antibody or antigen binding fragment thereof may be administered in combination with molecules that activate different stages or aspects of the immune response in order to achieve a broader immune response. In more preferred embodiment, the anti-CD24 antibody or antigen binding fragment thereof may be combined with anti-PD-1 or anti-4-1BB antibodies, without exacerbating autoimmune side effects.

10. Production

The anti-CD24 antibody or antigen binding fragment thereof may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The anti-CD24 antibody or antigen binding fragment thereof may also be produced from a stable cell line that expresses the antibody from a vector or a portion of a vector that has been integrated into the cellular genome. The stable cell line may express the antibody from an integrated replication-defective retroviral vector. The expression system may be GPExTM.

The anti-CD24 antibody or antigen binding fragment thereof may be purified using, for example, chromatographic methods such as affinity chromatography, ion exchange chromatography, hydrophobic interaction chromatography, DEAE ion exchange, gel filtration, and hydroxyapatite chromatography. In some embodiments, fusion proteins can be engineered to contain an additional domain containing amino acid sequence that allows the polypeptides to be captured onto an affinity matrix. For example, the antibodies described herein comprising the Fc region of an immunoglobulin domain can be isolated from cell culture supernatant or a cytoplasmic extract using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides.

Vaccines

Provided herein is a method of treating cancer or providing prophylaxis of a cancer described herein in a patient. The method may vaccinate the patient against the cancer. The method may comprise administering a composition comprising the sequence set forth in SEQ ID NO: 48 to a patient in need thereof. The composition may also be administered to a patient in need of treating adverse effects associated with a therapy comprising the use of an anti-CD24 antibody or cells expressing receptors binding CD24. The composition may also be used in the manufacture of a medicament for treating cancer or providing prophylaxis of cancer.

11. Pharmaceutical Compositions

Provided herein is a pharmaceutical composition comprising a therapeutically effective amount of any of the above-described anti-CD24 antibodies, cellular therapies, or peptide compositions, and a physiologically acceptable carrier or excipient. The pharmaceutical composition may comprise a prophylactically or therapeutically effective amount of the anti-CD24 antibody or antigen binding fragment thereof, and a pharmaceutically acceptable carrier In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, may also contain minor amounts of wetting or emulsifying agents, or pH buffering agents. These compositions may take the form of solutions, suspensions, emulsion, tablets, pills, capsules, powders, sustained-release formulations and the like.

Generally, the ingredients of the pharmaceutical composition may be supplied either separately or mixed together in unit dosage form, for example, as a dry lyophilized powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampoule of sterile water for injection or saline may be provided so that the ingredients may be mixed prior to administration.

The pharmaceutical composition may be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

12. Methods of Administration

Methods of administering the compositions and the pharmaceutical compositions thereof include, but are not limited to, parenteral administration (e.g., intradermal, intramuscular, intraperitoneal, intravenous and subcutaneous), epidural, and mucosal (e.g., intranasal and oral routes). In a specific embodiment, the composition is administered intramuscularly, intravenously, or subcutaneously. The composition may be administered by any convenient route, for example, by infusion or bolus injection, by absorption through epithelial or mucocutaneous linings (e.g., oral mucosa, rectal and intestinal mucosa, etc.) and may be administered together with one or more other biologically active agents. Administration can be systemic or local.

EXAMPLES

The disclosure has multiple aspects, illustrated by the following non-limiting examples.

Example 1

Generation of Monoclonal Antibodies Against Hypoglycosylated CD24

Overexpression of NEU1 and CD24 in tumors suggests the dysregulation of glycosidase. The dysregulation of glycosidase suggests that CD24, similar to MUC1, may be hypoglycosylated in tumors. Binding of the antibody, 3B6, to CD24 is hindered by sialic acid glycans (FIG. 1). Relative to commercially available anti-CD24 antibody, ML5 (BD bioscience), 3B6 binds strongly to N-SA-CD24 and N-SA-O-CD24 but only weakly to N-CD24 or fully glycosylated CD24 as detected by ELISA. This suggested that the epitopes to which 3B6 binds is indeed the protein backbone and that the binding of 3B6 is hindered by glycosylation of the epitope.

Figure 2A:
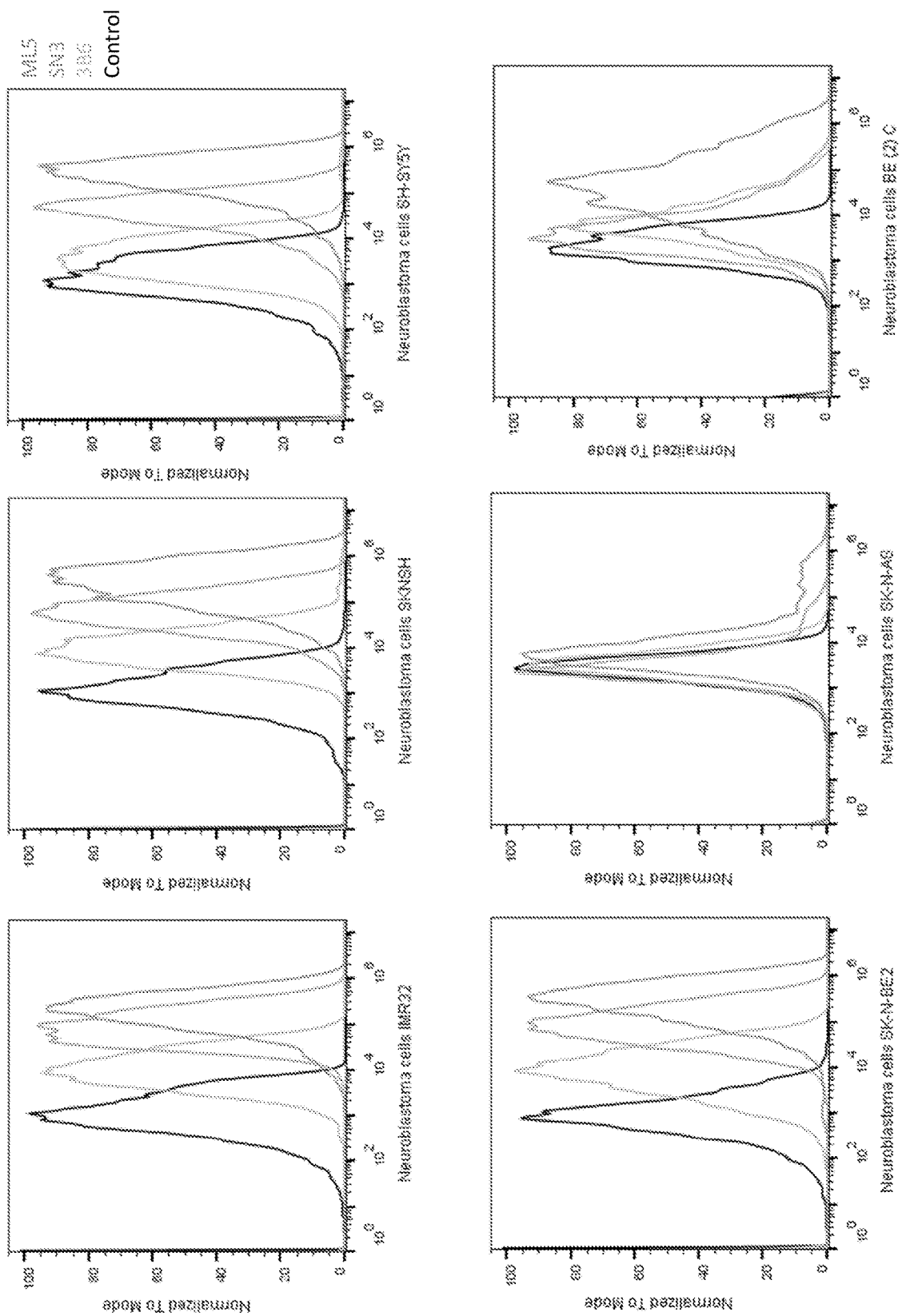
FIGS. 2A-B. Binding assays indicate 3B6 binds to neuroblastoma cell lines and medulloblastoma tumors.
Figure 2B:
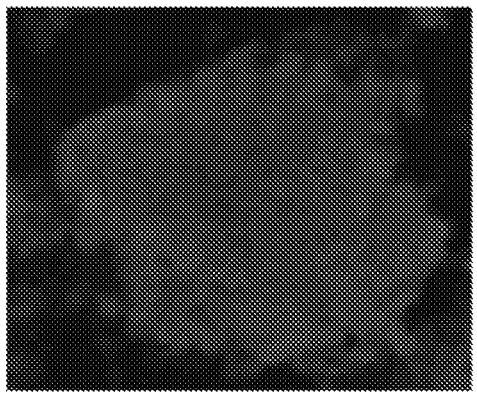
Figure 2B:
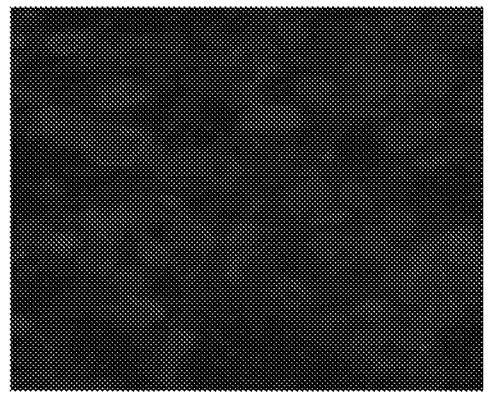
Figure 2B:
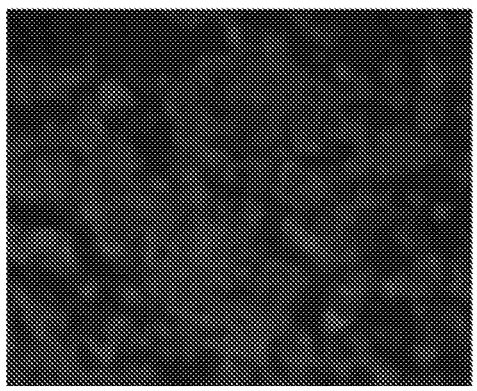
Figure 2B:
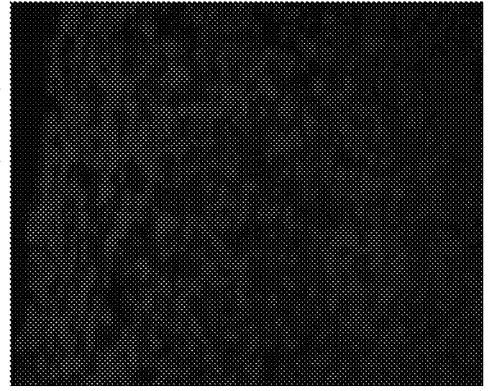

Fluorescence activated cell sorting (FACS) and immunofluorescence (IFA) staining results show that 3B6 binds multiple cancer cell lines, including neuroblastoma and medulloblastoma (FIGS. 2A-B). 3B6 binds to neuroblastoma cell lines IMR32, SK-N-SH, SH-SY5Y, SK-N-BE(2), and SK-N-BE(2)C, but not SK-N-AS (FIG. 2A). 3B6 also binds to 3 out of 4 medulloblastoma tumors obtained from patients as evaluated by IFA staining (FIG. 2B). These data suggest that 3B6 is capable of binding to cancerous cell lines and tumors.

Example 2

Affinity Maturation

Binding affinity of 3B6 for CD24 was considerably lower in comparison to commercial antibodies ML5 (BD Bioscience) and SN3 (Thermo Fisher). To increase the affinity and specificity of the binding of 3B6 to its antigen, affinity maturation of 3B6 was performed. We first cloned the heavy (IgH) and light (IgL) chains of the 3B6 antibody, and identified the Ig variable region sequence as follows:

EVKFEESGGGLVQPGGSIKLSCAASGVTFSEAWMDWVRQSPEKGLEWVA

EIRDKTKNYVTYYAESVKGRFTISRDDSKSRVYLQMNNLRTEDTGIYYC

TGAMDYWGQGTSVTVSS

The VH and VL fragments from the parental 3B6 antibody were converted into the scFv format and cloned into a phage display vector. The scFv was displayed monovalently on the phage, and thus allowing the selection of phage clones with higher affinities. In order to verify the scFv display level, the scFv was fused with the Flag-6xHis detection tag. Phage ELISA was carried out to validate the binding of the parental antibody to the antigen in phage display format. The binding signal from the phage supernatant was significant, and so the project proceeded to library construction.

Three rounds of selection and screening were carried out. Decreasing concentrations of antigen CD24-GST and biotinylated CD24-GST were used in screening to select higher binder clones. 48 clones from each CDR mutagenesis library were picked, cultured, assayed for binding and sequenced.

Once the sequences of the affinity matured scFv clones were confirmed, the scFv of affinity matured clones were reformatted to full-length antibody genes and transiently expressed in mammalian cells. All affinity matured antibodies underwent 0.01 liter small scale production. The parental antibody was also scaled-up for direct comparison. Plasmids for the indicated heavy and light chains (Table 1) were transfected into suspension HEK293 cells using chemically defined media in the absence of serum to make the antibodies. Five days after transfection, the conditioned media was collected and clarified. Whole antibodies in the conditioned media were purified using MabSelect SuRe Protein A medium (GE Healthcare).

DIVMTQTPLSLSVTIGQPASISCKSSQSLLYSNGKTYLNWLQQRPGQSP

KRLIYQVSKLDPGIPDRFSGSGSETDFTLKISRVEAEDLGIYYCLQGTS

YPWTFGGGTKLEIK

Figure 3:
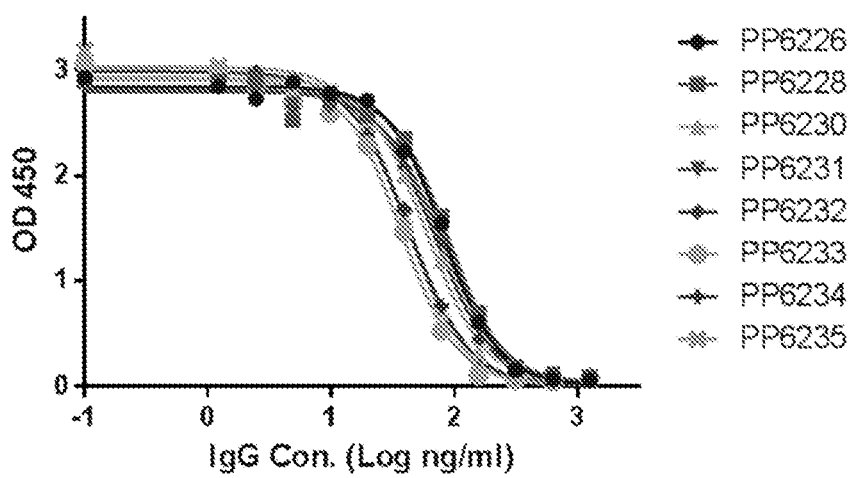
FIG. 3. Plot of competitive ELISA comparing the ability of variants of 3B6 to block 3B6 binding to CD24-GST fusion protein. PP6226 has the same variable region as 3B6.
Figure 4:
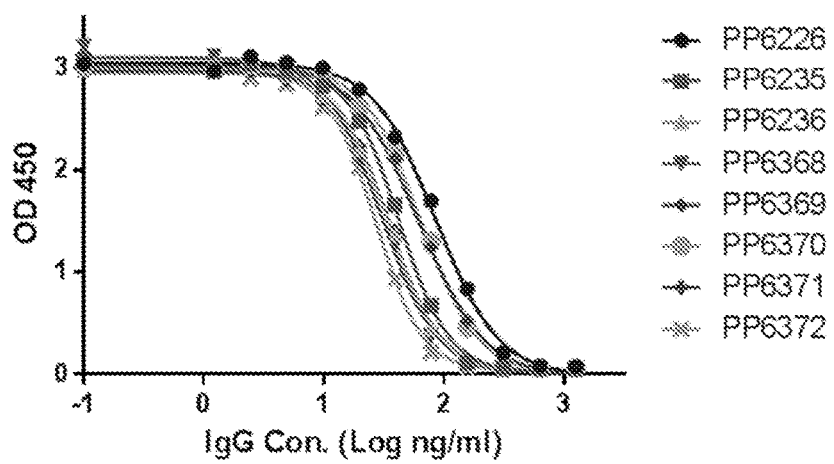
FIG. 4. Plot of competitive ELISA comparing the ability of variants of 3B6 for their ability to block 3B6 binding to CD24-GST fusion protein. PP6226 has the same variable region as 3B6.
Figure 5:
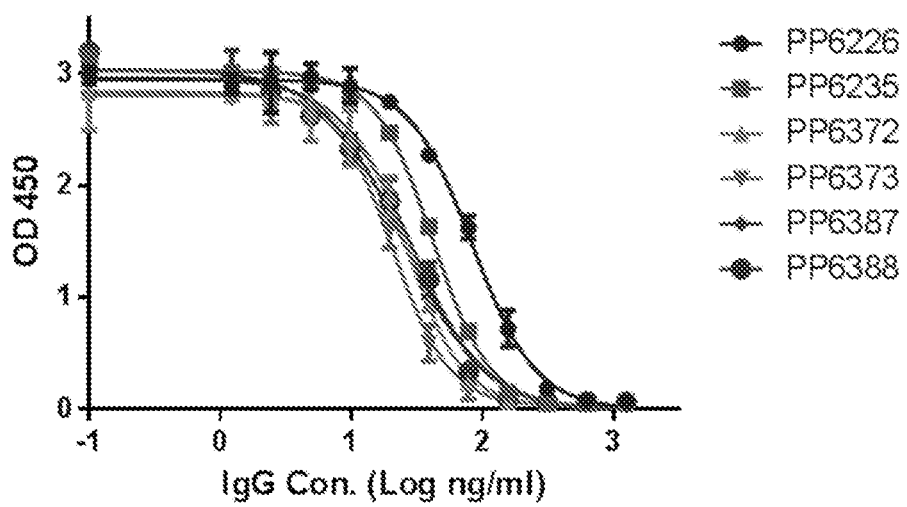
FIG. 5. Plot of competitive ELISA comparing the ability of variants of 3B6 for their ability to block 3B6 binding to CD24-GST fusion protein. PP6226 has the same variable region as 3B6.

Purified affinity matured antibodies and the parental antibody were evaluated by competition ELISA for their affinity to the antigen. Antibody PP6226 (3B6 parent variable regions) was coated onto plates at 2 µg/mL. Affinity matured antibodies were incubated with CD24-GST first, then incubated with the plate, followed by secondary detection antibody incubation. As shown in FIGS. 3-5, we generated 16 antibodies with varying ability to compete with its parent clones. The amino acid sequences of the heavy and light chains of these antibodies are SEQ ID NOS: 3-10 (heavy chains) and SEQ ID NOS: 11-16 (light chains).

Figure 6:
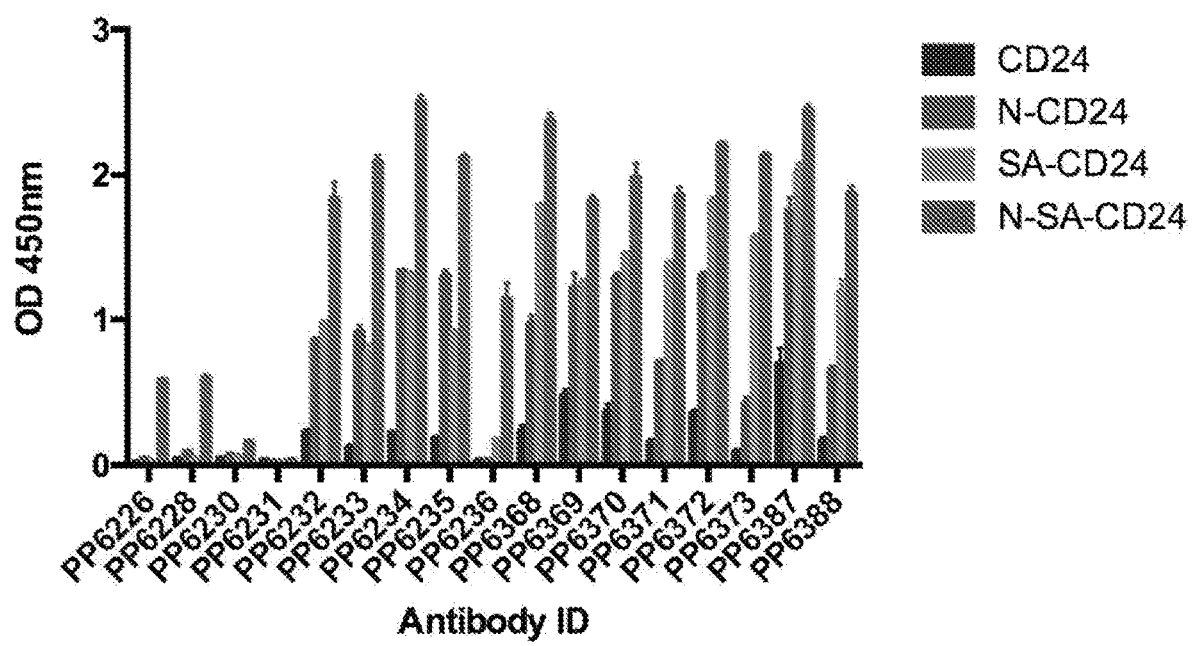
FIG. 6. Bar plot of ELISA results indicating the relative affinity of affinity-mature chimeric anti-CD24 antibodies to CD24 expressed by CHO cells. Twelve of the clones showed increased affinity and different specificity against fully glycosylated CD24, N-CD24, SA-CD24, and N-SA-CD24 relative to 3B6 (PP6226).

To determine if the affinity-matured clones have stronger binding to CD24 and if the interactions are glycan-regulated, we treated CD24 with either N-glycanase (N-CD24), sialidase NanA (SA-CD24) or both (N-SA-CD24). The 16 clones described in FIGS. 3-5 were tested using ELISA. As shown in FIG. 6, despite significant affinity for CD24-GST, PP6231 and PP6230 failed to bind to CD24 expressed by mammalian cells regardless of glycosylation. On the other hand, most other clones maintained preferential binding to CD24 that are treated with sialidase and/N-glycanase. Nevertheless, since the relative impact of sialidase and N-glycanase on antibody binding varies considerably among different clones, each clone must be tested individually in order to determine their susceptibility to glycan hindrance.

Figure 7:
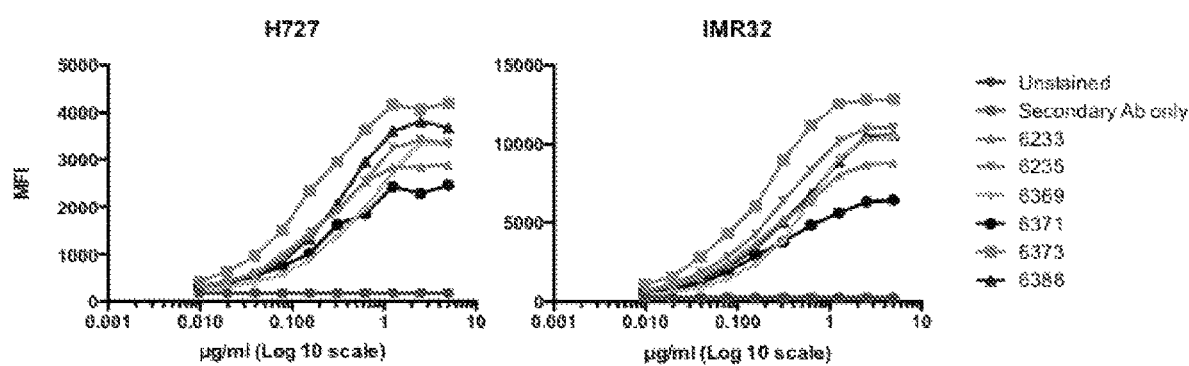
FIG. 7. Titration assay of various affinity-mature chimeric anti-CD24 antibodies tested against lung cancer cell line NCI-H727 (left panel) and neuroblastoma cell line IMR32 (right panel). The maximum antibody concentration tested was 5 μg/ml with a titration factor of 2× to a minimum concentration of 0.01 μg/ml. An unstained (0 μg/ml) negative control is also shown.
Figure 8:
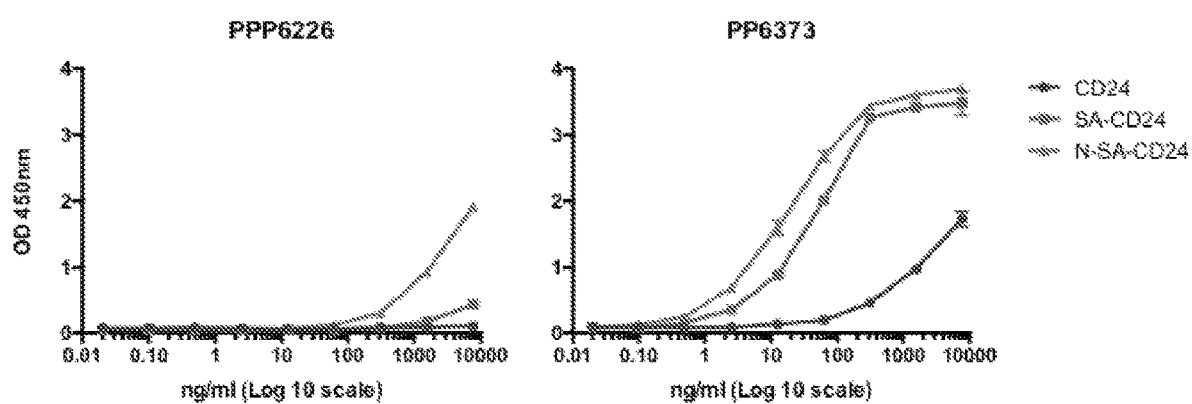
FIG. 8. Quantitative comparison of binding between different CD24 glycoforms and anti-CD24 antibodies: parental PP6229 vs affinity matured PP6373. Fc removed CD24 were coated onto ELISA plate, and were then treated with either buffer (CD24), NanA (SA-) or NanA+N-glycanse (SA-N—) prior to adding given doses of PP6626 (left panel) or PP6373 (right panel). The maximum concentration tested was 7812.50 ng/ml with titration factor of 5× to a minimum concentration of 0.02 ng/ml.

We choose 6 clones with strong binding SA-N-CD24, but which exhibit minimal binding to CD24, and tested them for binding to two cancer cell lines, lung cancer cell line H727 and neuroblastoma cell line IMR32. As shown in FIG. 7, despite their similar binding to SA-N-CD24, the 6 clones showed significantly different binding to cancer cells. Importantly, PP6373 exhibit significantly stronger binding to both cancer cell lines tested. Therefore, this clone is chosen for further study. The heavy chain sequence for PP6373 is listed in SEQ ID NO: 6 and the light chain sequence is listed on SEQ ID No.16. Compared with the parental sequence, the heavy chain has three mutations in CDR2, while the light chain has one mutation in CDR3 of the light chain. As shown in FIG. 8, these mutations not only increased binding to SA-N-CD24 by nearly 100-fold, but also make the interaction more strictly regulated by desialylation. It is also of note that PP6373 gained the ability to bind to CD24 even without deglycosylation at 1/1000 level of that to SA-N-CD24. However, since CHO cells is known to have incomplete glycosylation, it is likely that the binding reflect the higher sensitivity of the antibody to detect minor glycoform in the recombinant CD24 prepared from CHO cells.

Example 3

Antigenic Epitope Recognized by 3B6 and PP6373

Figure 9:
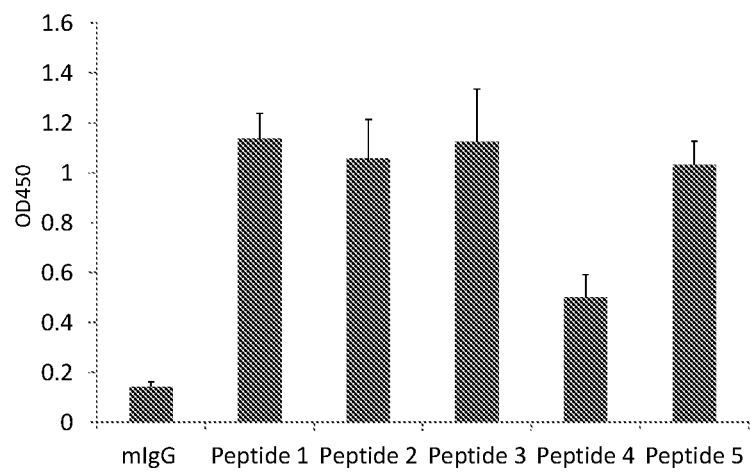
FIG. 9. Mapping 3B6 binding site through peptide inhibition assay. Of the five overlapping CD24 peptides tested, only one (peptide 4) contains the antigenic epitope.
Figure 10:
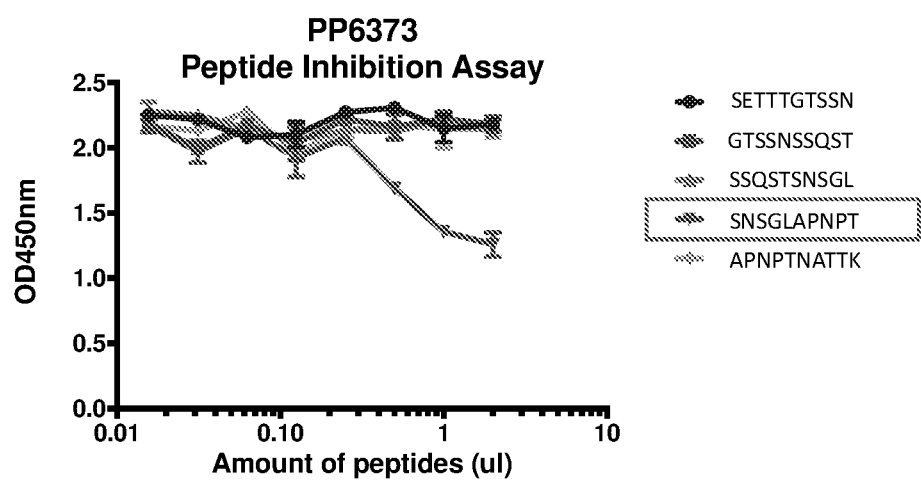
FIG. 10. Mapping the PP6373 binding site through peptide inhibition assay. Of the five overlapping CD24 peptides tested, only one (SNSGLAPNT (SEQ ID NO: 46)) contains the antigenic epitope.

To determine the antigenic epitope recognized by 3B6 and affinity matured clone PP6373, we synthesized overlapping peptides covering the mature CD24 amino acid sequence (Seq ID No 42), and pre-incubated them with 3B6 antibody prior to adding 3B6 to plates pre-coated with N$^-$O$^-$ CD24 protein (CD24Fc pretreated sequentially with N-glycosidase, NanA and O-glycosidase). As shown in FIG. 9, of the 5 peptides tested (SEQ ID NOS: 43-47), only peptide 4 (SEQ ID NO: 46) demonstrates significant blocking of the 3B6-CD24 interaction, which suggest that the CD24 binding epitope is encompassed in this sequence. To confirm that PP6373 recognizes the same epitope, we titrated the five peptides over a large dose range. As shown in FIG. 10, only peptide 4 showed dose-dependent inhibition of PP6373 binding to SA-N-CD24.

Figure 11:
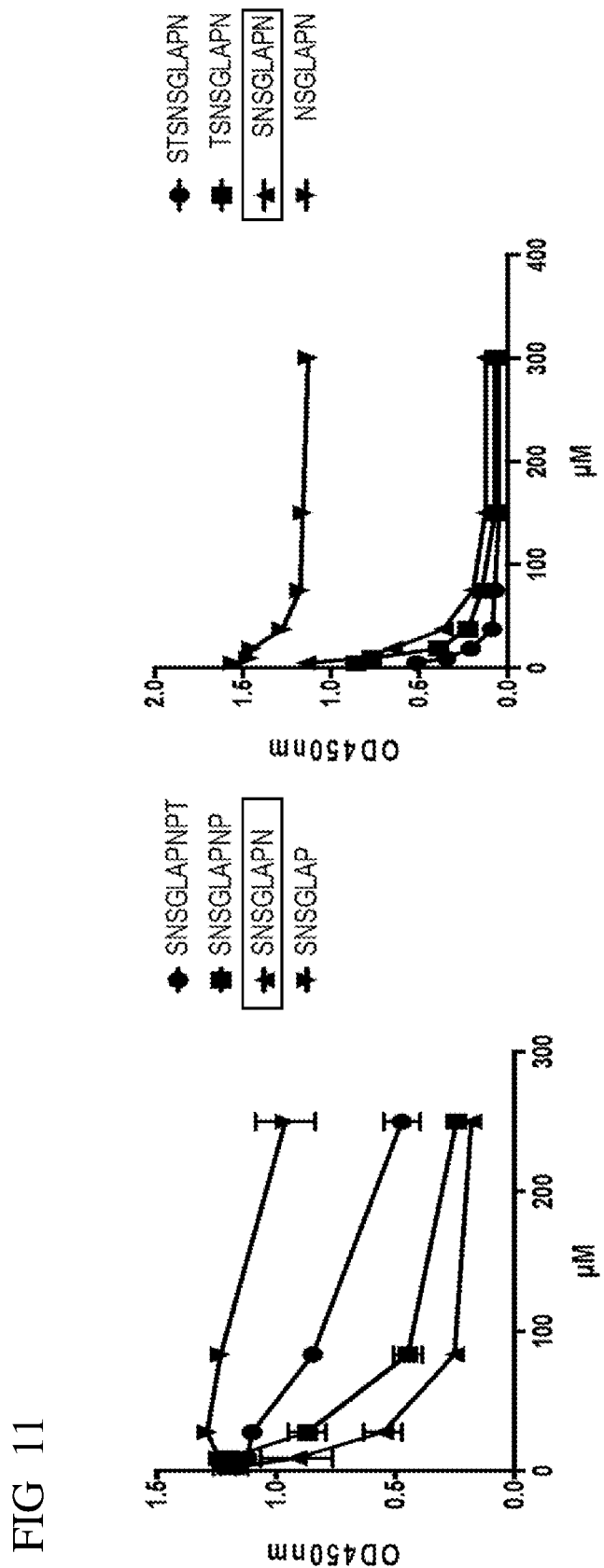
FIG. 11. Mapping the PP6373 epitope with truncated peptides from the peptide 4 antigenic epitope sequence. The data indicate that the optimal epitope is contained within the sequence SNSGLAPN (SEQ ID NO: 48).

To define the minimal PP6373 binding site, we truncated peptide 4 one amino acid at a time and compared their inhibition of PP6373 binding to SA-N-CD24. As shown in FIG. 11, while deletion of 3 amino acids from the C-terminus abrogated the inhibition, deletion of one or two amino acids significantly improved the inhibition (left panel). Furthermore, deletion of any amino acid from the N-terminus of peptide 4 also abrogated the inhibition (right panel). These data identify SNSGLAPN (SEQ ID NO: 48) as the optimal epitope recognized by PP6373.

Our identification of the antigenic epitope allows one to generate additional antibodies with similar properties. In one embodiment, one could generate new antibodies using the synthetic peptide comprising the sequence SNSGLAPN (SEQ ID NO: 48). The peptide may be coupled to another immunogenic protein carrier, or used in conjunction with adjuvants. In another embodiment, one could use the peptide to identify other anti-CD24 mAbs that recognize the same epitope to generate cancer-specific antibodies for diagnosis and treatment of cancer. In yet another embodiment, the antigenic peptide can be used to neutralize or inhibit potential adverse effects associated with antibodies that bind to epitopes comprising the core sequence of SEQ ID NO: 48. The peptide may be modified for better stability for in vivo use using methods known in the art, including but not limiting to use of D-amino acids, replacement of 0 with S in one or more peptide-bonds, addition of a fusion sequence to improve solubility or half-life (e.g. albumin fusions). In yet another embodiment, a molecule comprising the amino acid sequence in SEQ ID NO: 48 can be used as a vaccine for treatment and prophylaxis of cancer vaccine.

Example 4

Expression of Antigenic Epitope in Normal Versus Malignant Tissues

To determine whether the epitope recognized by the PP6373 is preferentially presented in cancer vs normal tissues, we analyzed the tissue binding by immunofluorescence using biotinylated PP6373. The data on normal tissues are summarized in Table 2, while that of the cancer tissues are summarized in Table 3. Furthermore, we evaluate the binding of the antibody to normal benign and malignant brain cancer. The data are summarized in Table 4.

TABLE 1

Antibodies produced in HEK293 cells through transient transfection and purified with IgG1

| Parental | | Affinity matured panel 1 | | Affinity matured panel 2 | |
|---|---|---|---|---|---|
| PP6226- anti-CD24 | PP6228-H4041 + L4040 | P3050.H1.A4 | PP6368-H4069 + L4069 | P3050.ComF1.A11 |
| H4040 + L4040 | PP6230-H4042 + L4040 | P3050.H2.A7 | PP6369-H4070 + L4069 | P3050.ComF1.H4 |
| | PP6231-H4043 + L4040 | P3050.H2.B11 | PP6370-H4071 + L4069 | P3050.ComF1.2F4 |
| | PP6232-H4040 + L4041 | P3050.L3.B9 | P6371-H4072 + L4070 | P3050.ComF1.2F5 |
| | PP6233-H4040 + L4042 | P3050.L3.C7 | PP6372-H4073 + L4071 | P3050.ComF1.C9 |
| | PP6234-H4040 + L4043 | P3050.L3.D8 | PP6373-H4069 + L4071 | P3050.ComF1.2H1 |
| | PP6235-H4041 + L4042 | P3050.H1.A4.L3.C7 | PP6387-H4071 + L4071 | P3050.ComF2.B1 |
| | PP6236-H4043 + L4042 | P3050.H2.B11.L3.C7 | PP6388-H4072 + L4069 | P3050.ComF2.A5 |

Table: List of the transient transfection and purification done to obtain the IgG. H40xx indicates the heavy chain construct and L40xx the light chain construct. P3050.xx indicates the original clone obtained from phage panning. All the IgG expressed well. The PP numbers are serial codes used to distinguish the proteins produced.

TABLE 2

Immunofluorescence staining of PP6373 showed minimal binding to normal tissues.

| Organ | +/− | Staining pattern |
|---|---|---|
| Normal stomach | − | |
| Normal duodenum | − | |
| Normal small intestine | − | |
| Normal colon | − | |
| Normal parotid gland | − | |
| Normal thyroid gland | − | |
| Normal pancreas | + | Weak cell surface, Intracellular? |
| Normal prostate | − | |
| Normal aorta | − | |
| Normal testis | − | |
| Normal greater omentum | − | |
| Normal breast | − | |

TABLE 2-continued

Immunofluorescence staining of PP6373 showed minimal binding to normal tissues.

| Organ | +/− | Staining pattern |
|---|---|---|
| Normal lymph node | − | |
| Normal skin | − | |
| Normal medulla oblongata | | |
| Normal spleen | − | Few positive, cell surface? |
| Normal uterus | − | |
| Normal vagina | − | |
| Normal bladder | − | |
| Normal nerve | − | |

TABLE 3

Reactivity of PP6373 to malignant tissues

| Organ | Percent positive | Staining pattern |
|---|---|---|
| Malignant colon | 0/1 | |
| Malignant esophagus | 0/1 | |
| Malignant stomach | 0/2 | |
| Malignant ovary | 16/25 | cell surface |
| Malignant soft tissue | 0/1 | |
| Malignant kidney | 1/1 | weak surface |
| Malignant liver | 14/19 | cell surface |
| Malignant breast | 12/20 | cell surface |
| Malignant skin | 1/1 | cell surface |
| Malignant testis | 1/1 | Intracellular/cell surface |
| Malignant lung | 11/39 | cell surface |

TABLE 4

PP6373 binding to normal benign and malignant brain tumors

| Pathology | Cell surface | Intracellular | Negative |
|---|---|---|---|
| Astrocytoma | 2/24 (8%) | 17/24 (71%) | 5/24 (21%) |
| Glioblastoma | 3/8 (38%) | 2/8 (25%) | 5/8 (37%) |
| Oligodendroglioma | 4/8 (50%) | 3/8 (38%) | 1/8 (12%) |
| Ependymoma | 5/8 (63%) | 0/8 (0%) | 3/8 (37%) |
| Medulloblastoma | 7/10 (70%) | 0/10 (0%) | 3/10 (30%) |
| Meningioma benign | 0/22 (0%) | 15/22 (68%) | 7/22 (32%) |
| Normal CNS tissue | 0/16 (0%) | 0/16 (0%) | 16/16 (100%) |

As shown in Table 2, with exception of pancreas and perhaps spleen, PP6373 did not stain normal tissues. It is of note that most of the staining in the pancreas appear intracellular. In the spleen, a rare number of cells showed staining. In contrast, as shown in Table 3, most cancers tested show strong binding to PP6373. As shown in Table 4, while normal CNS tissues are devoid of CD24, benign meningioma show intracellular although not cell surface staining. Importantly, malignant brain tumors, including astrocytoma, glioblastoma and oligodendroglioma exhibit cell surface staining at rate ranging 8-70%, in addition, some cancer tissues showed intracellular staining.

In one embodiment, PP6373 may be used to differentiate malignant brain tumor from normal or benign brain tissue. In another embodiment, PP6367 can be used to identify cancer tissues in solid organs, such as liver, lung, breast and ovary.

Example 5

PP6373 Retards Lung Cancer Growth In Vivo

Figure 12:
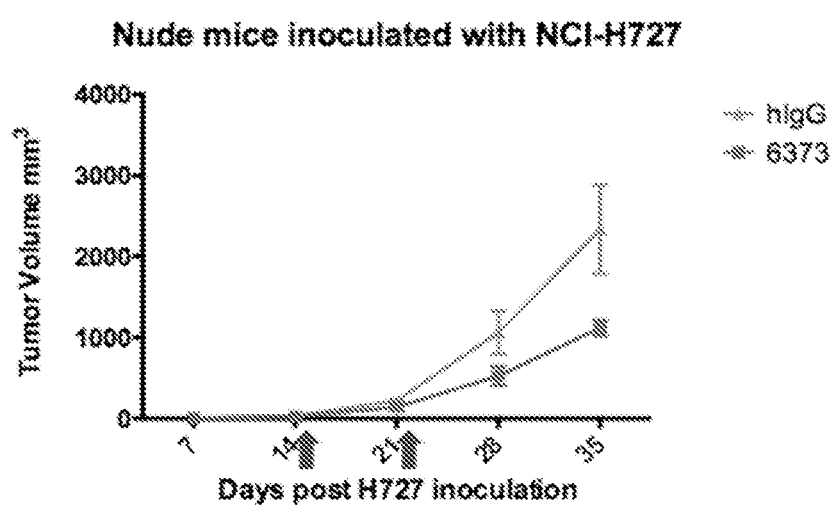
FIG. 12. Plot indicating PP6373 reduces tumor growth in vivo in a mouse model. Nude mice with palpable lung cancer xenograft received either control human IgG or PP6373 at the two time points indicated by arrows, the growth of tumors were subsequently measured weekly.

To test if PP6373 can retard tumor growth in vivo, we challenged nude mice with human lung cancer cell line H727 subcutaneously. Once the tumor become palpable, the tumor bearing mice received two injections of PP6373 of 5 mg/kg (14 and 21 days post H727 inoculation). As shown in FIG. 12, compared with IgG control, PP6373-treated tumor grew at a substantially reduced rate. These data demonstrate that unmodified PP6373 is capable of exhibiting anti-tumor activity in vivo.

Figure 13:
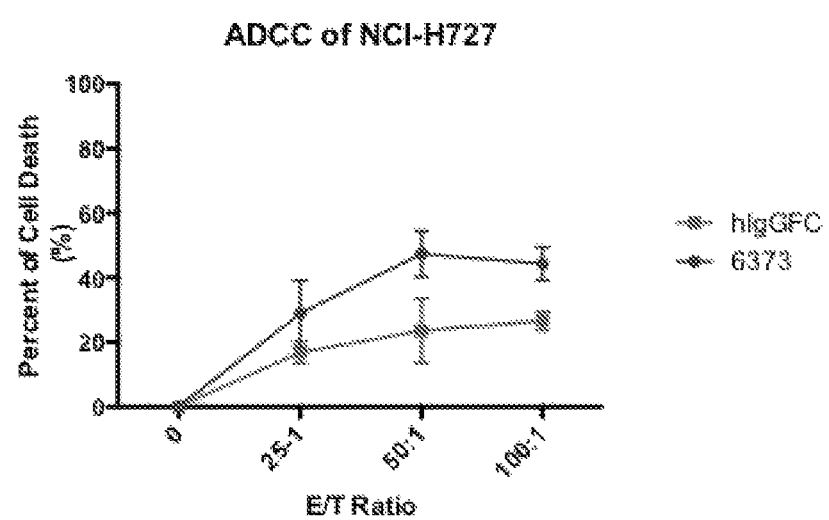
FIG. 13. Plot indicating PP6373 induced cellular cytotoxicity (ADCC) against human cancer cell line H727. H727 cells co-incubated with effector cells PBL with PP6373 and human IgG FC at 5 μg/ml induced ADCC.

Consistent with the tumor-retardation in vivo, our in vitro studies demonstrate that PP6367 mediates potent antibody-dependent cellular cytotoxicity, as demonstrated in FIG. 13.

Figure 14:
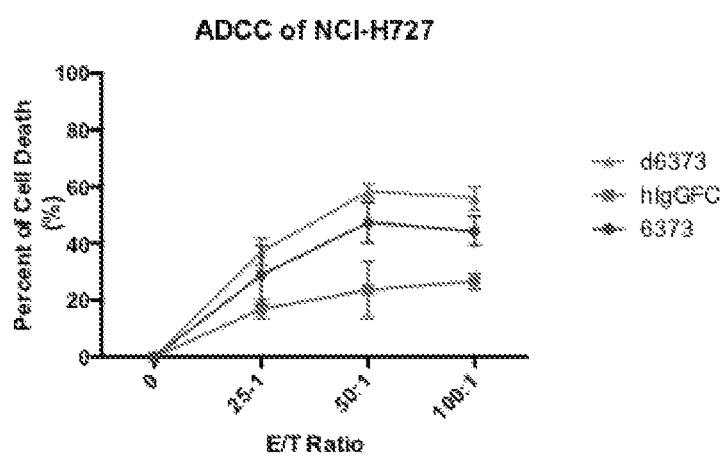
FIG. 14. Plot indicating PP6373 without core fucosylation (d6873) induces higher ADCC against human cancer cell line H727 than PP6373. H727 cells co-incubated with effector cells PBL with d6373, PP6373 and human IgG FC at 5 μg/ml induced ADCC.

Since ADCC is affected by glycosylation, especially fucosylation, we used antibody engineering to generate PP6373 without core FC fucosylation (d6373). As shown in FIG. 14, fucosylation increased the ADCC activity of PP6373.

Our data demonstrate that PP6373 can be used to treat cancer. In one embodiment, PP6373 WT IgG1 can be used as cancer therapeutic antibodies, to be administrated to cancer patients. In another embodiment, the antibody can be glycoengineered either chemically, or produced in cell line lacking fucosyl transferase.

Example 6

Bispecific Antibodies Based on PP6373 and OKT3 Sequence

To weaponize anti-CD24 antibodies, we produced bispecific antibodies that bind to both CD24 and CD3. In one embodiment, anti-CD24 and anti-CD3 (OKT3) antibodies are converted into single chain antibodies with reactivity to CD24 and CD3, respectfully, and linked by the flexible linker sequence GGGGSGGGGSGGGGS (SEQ ID NO: 49). The sequence of PP6373 single chain antibody is listed in SEQ ID NO:17, while the OKT3 single chain sequence is listed as SEQ ID NO: 18.

Figure 15:
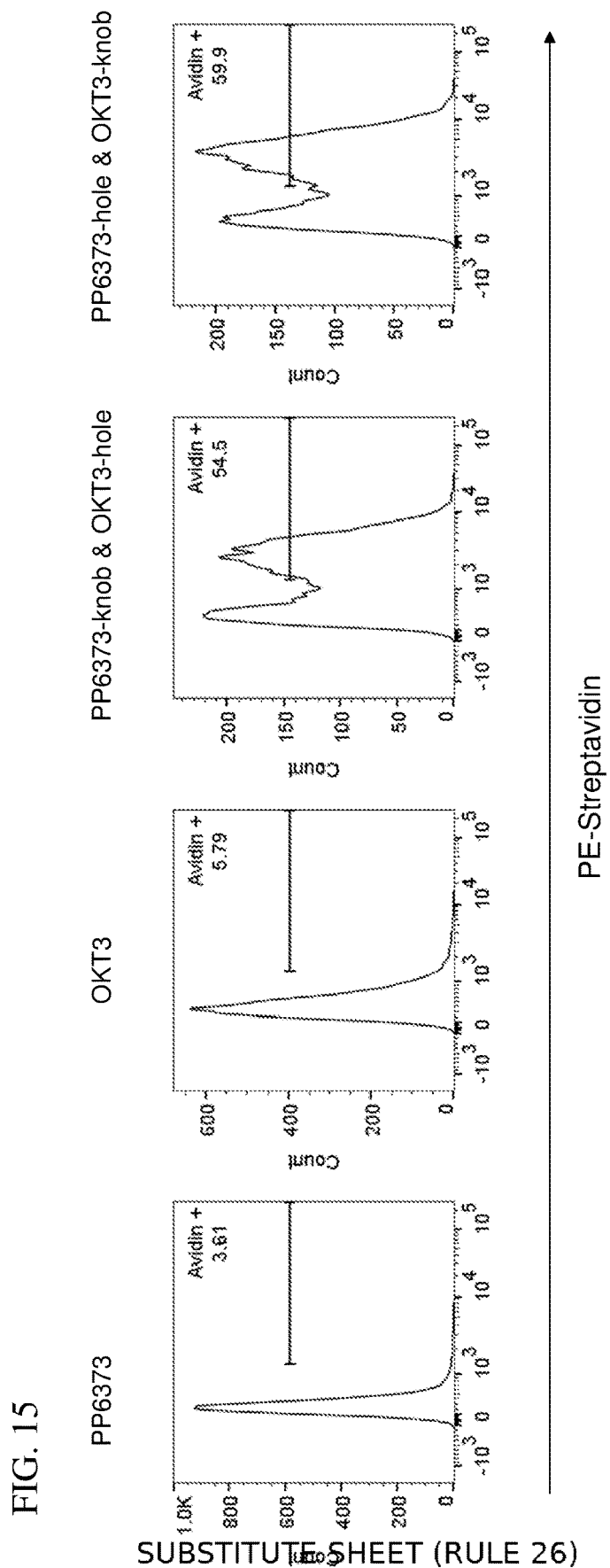
FIG. 15. Flow cytometry plots indicating PP6373-hole and OKT3-knob combination show higher bispecificity than PP6373-knob and OKT3-hole. Jurkat cells were stained with tissue culture supernatants of 293T cells transfected with PP6373, OKT3, PP6373-knob & OKT3-hole, or PP6373-hole & OKT3-knob, followed by incubation with biotinylated SA-N-CD24 protein. PE-Steptavidin signal was measured by flow cytometry. Three independent experiments were performed.

In one embodiment, the bispecific antibody is generated through knob and hole technology in which the two partners of the bispecific molecule have complementary mutations in the Fc region to create knob and holes to facilitate formation of bispecific heterodimers. The sequences of the knob and hole variants of PP6373 and OKT3 are listed in SEQ ID NOS:19-22. To evaluate the bispecificity of different knob and hole configurations, we developed an assay consisting of staining Jurkat cells with the product of co-transfection of different knob-hole products. Briefly, CD3+Jurkat cells were stained first with the tissue culture supernatants from transfected 293T cells. After washing away unbound antibodies, the cells were incubated with biotinylated SA-N-CD24. The amounts of SA-N-CD24 on Jurkat cells were detected by PE-Streptavidin. As shown in FIG. 15, combination of PP6373-hole and OKT3-knob yields the highest CD24 binding to Jurkat cells, which indicated that PP6373-hole and OKT3-knob pairing is the most suitable for the knob-hole strategy.

Figure 16:
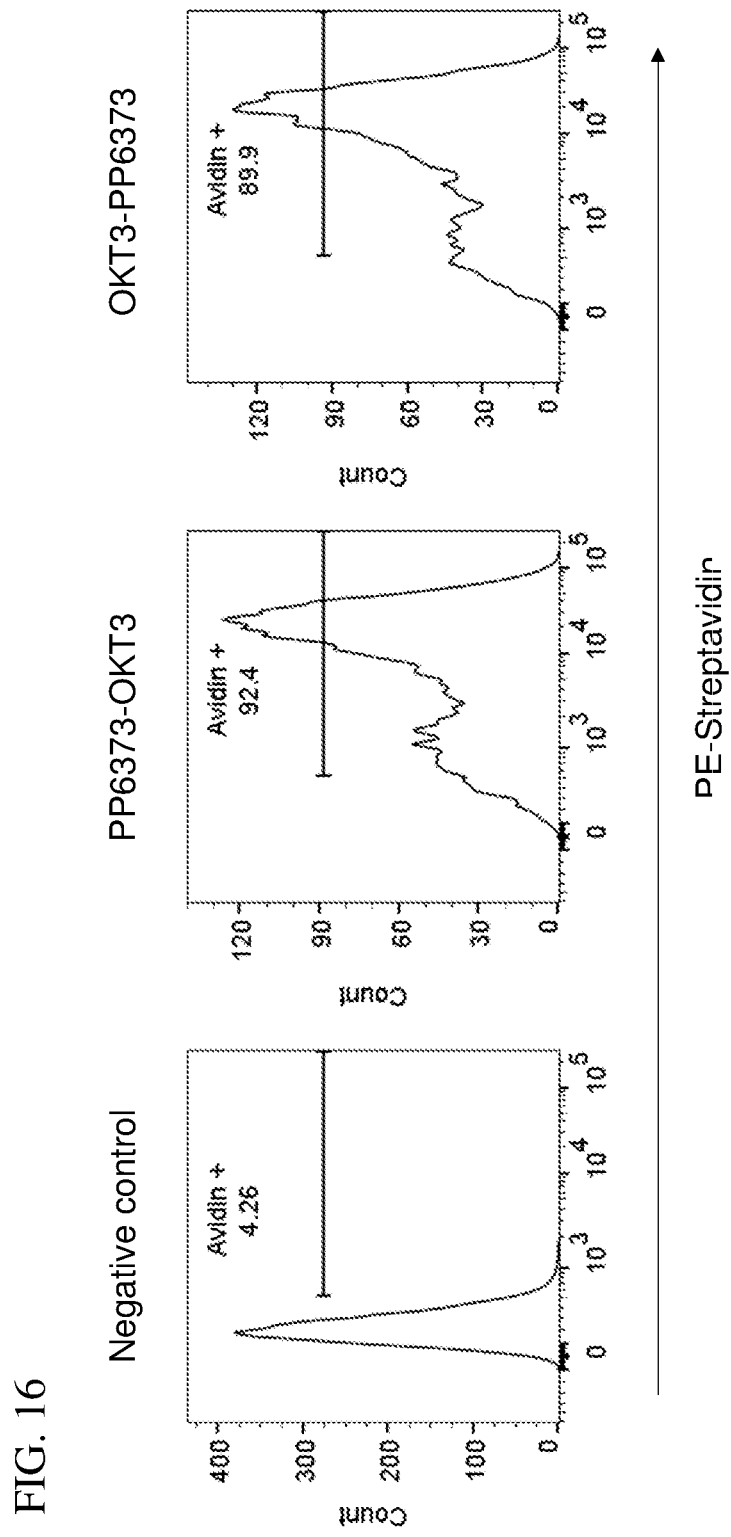
FIG. 16. Flow cytometry plots indicating PP6373-OKT3 induces higher bispecific activity than OKT3-PP6373. Jurkat cells were stained with tissue culture supernatants of 293T cells transfected with empty plasmid (negative control), PP6373-OKT3 or OKT3-PP6373, followed by incubation with biotinylated SA-N-CD24 protein. PE-Steptavidin signal was measured by flow cytometry. Three independent experiments were performed.

In another embodiment, the bispecific antibody is generated through tandem repeat of two single-chain binding motives. Again, we compared the activity of two configurations with the different binding motifs in opposing orders, PP6373-OKT3 and OKT3-PP6373, as listed in Seq ID-23 and 24, respectively. As shown in FIG. 16, the construct with PP6373 single chain at the N terminal end (PP6373-OKT3; SEQ ID NO:23) shows higher bispecific activity.

Figure 17:
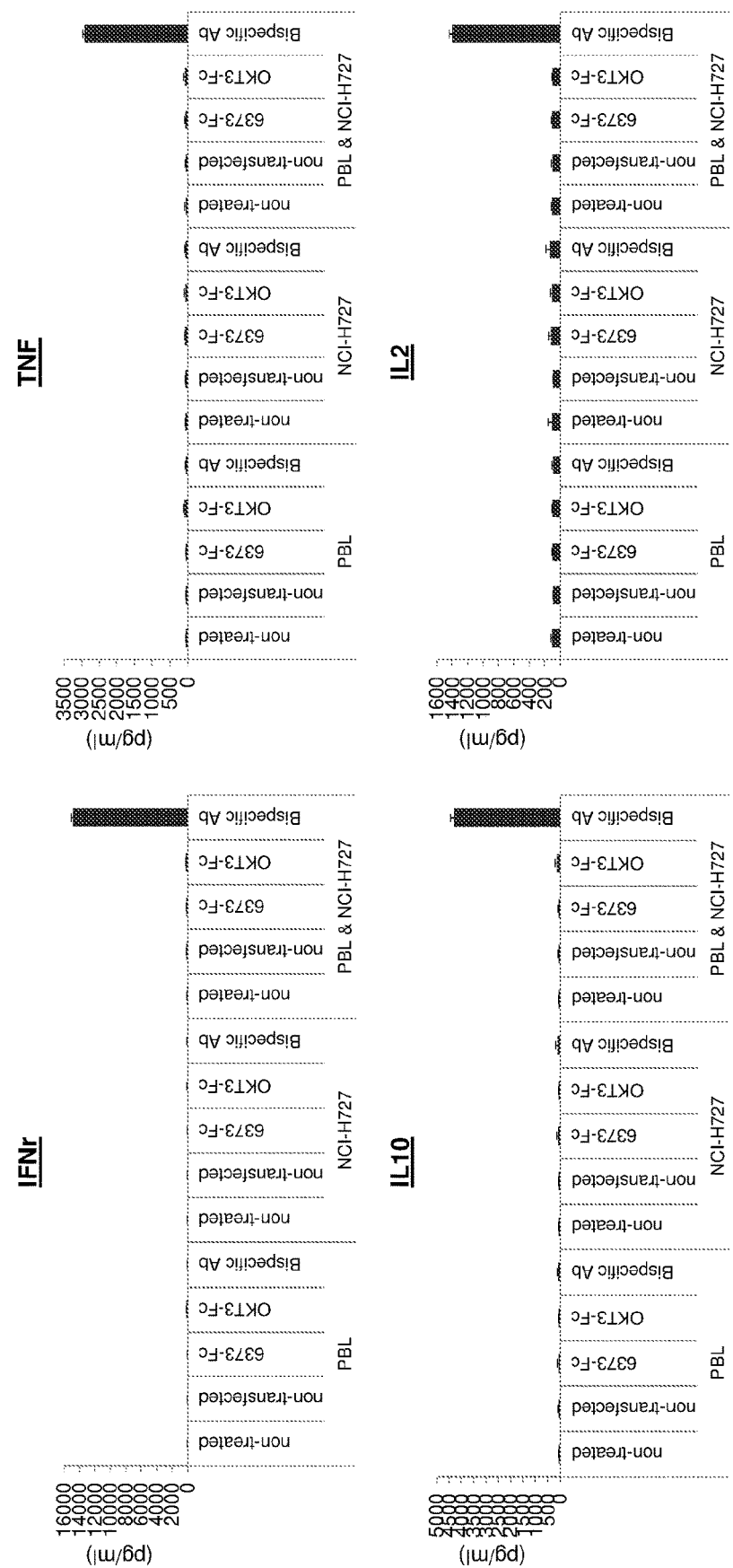
FIG. 17. Flow cytometry plot indicating bispecific antibody PP6373-OKT3 has anti-tumor activity. Lung cancer cell H727 and activated human T cells were incubated at 1:5 with tissue culture supernatants of non-treated 293T cells or transfected with empty plasmid (non-transfected), PP6373, OKT3, PP6373-OKT3 for 12 hours. Cytokines (IFNr, TNF, IL10, IL6, IL4 and IL2) in tissue culture media were measured by flow cytometry. Three independent experiments were performed.

To determine whether the bi-specific antibody has anti-tumor cell activity, we co-incubated the lung cancer cell line H727 with T cells that had been activated with anti-CD3 and anti-CD28 for 2 days. We first tested if the cancer cell can specifically trigger production of cytokines. As shown in FIG. 17, significant cytokines are induced by the bispecific antibody but not by OKT3-Fc of PP6373-Fc. More importantly, the bispecific antibody does not induce cytokine production unless both T cells and tumor cells are present together. These data demonstrate that the bispecific antibodies trigger T cell activation by engaging both T cells and tumor cells.

Figure 18:
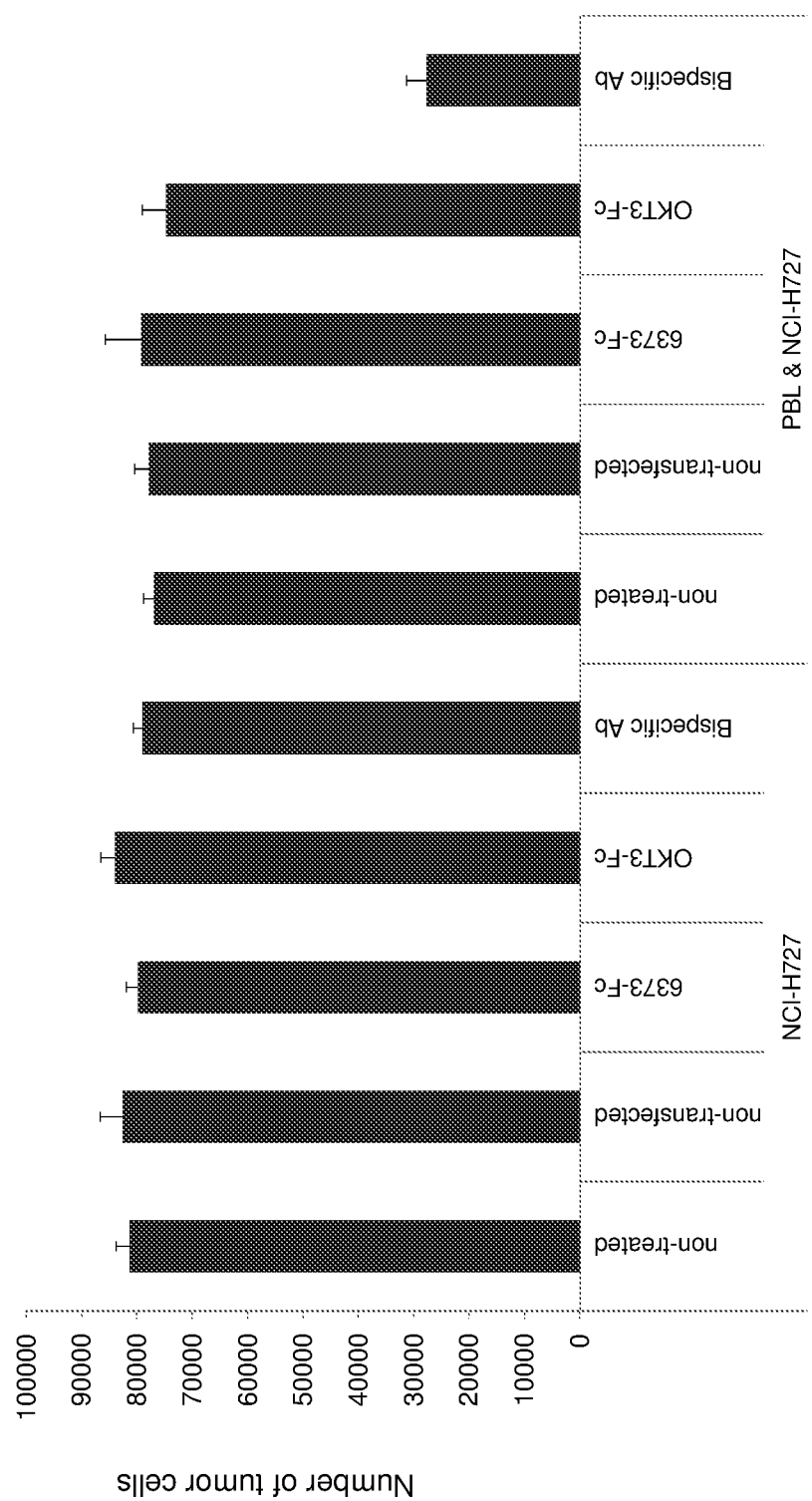
FIG. 18. Flow cytometry plot indicating bispecific antibody PP6373-OKT3 induced cytotoxicity of tumor cells by T cells. Lung cancer cell H727 and activated human T cells were incubated at 1:5 with tissue culture supernatants of non-treated 293T cells or transfected with empty plasmid (non-transfected), PP6373, OKT3, PP6373-OKT3 for 12 hours. Lung cancer cells and human T cells were collected and stained with anti-human CD45 and live/dead reagent Aqua. Tumor cells number was plotted as double negative of anti-CD45 and Aqua. Three independent experiments were performed.

Concurrent with the cytokine release assay, we also evaluated the cytotoxicity on tumor cells based on bead-based counting of live dye-labeled tumor cells by flow cytometry. As shown in FIG. 18, the bispecific antibodies cause loss of tumor cells if, and only if, T cells are present.

Figure 19:
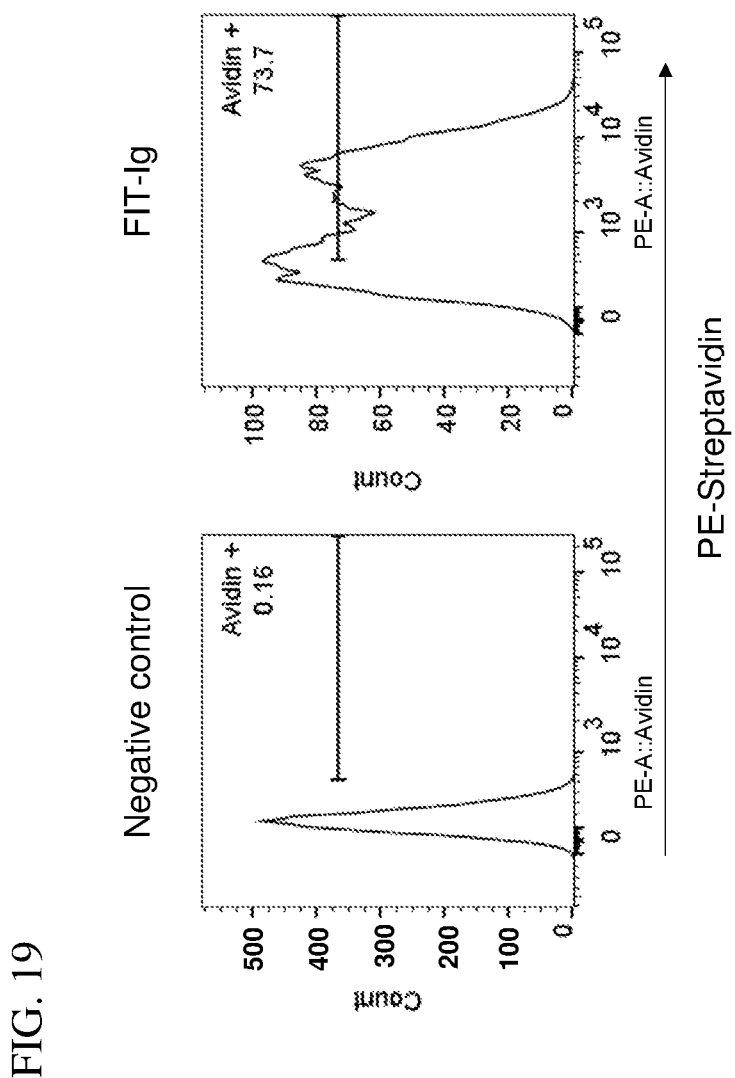
FIG. 19. Flow cytometry analysis of FIT-Ig induced high bispecific activity. Jurkat cells were stained with negative control (non-transfected 293T supernatant) or FIT-Ig, followed by incubation with biotinylated SA-N-CD24 protein. PE-Steptavidin signal was measured by flow cytometry. Three independent experiments were performed.
Figure 20:
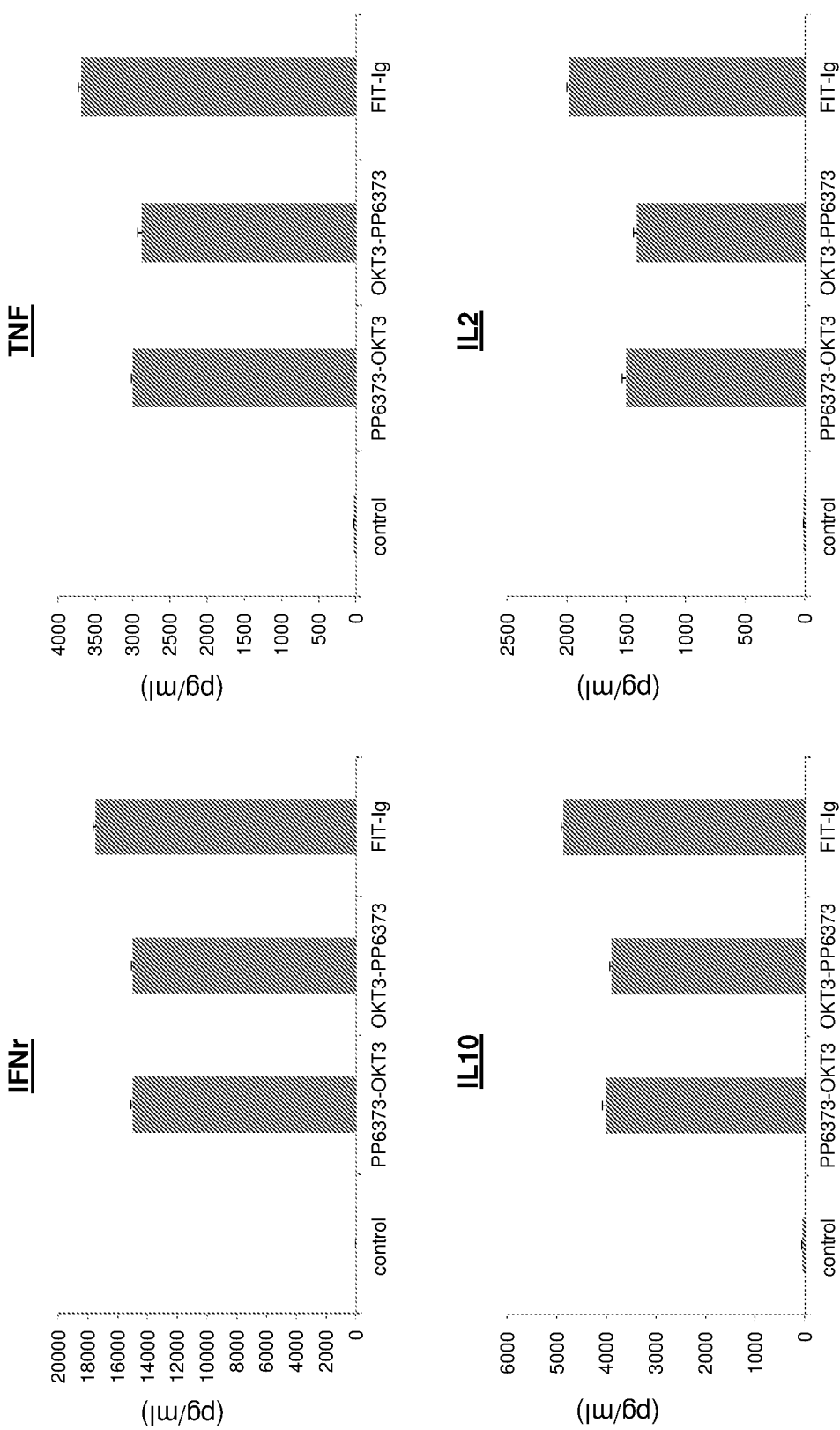
FIG. 20. Flow cytometry analysis indicates FIT-Ig has higher anti-tumor activity than PP6373-OKT3 and OKT3-PP6373. Lung cancer cell H727 and activated human T cells were incubated at 1:5 with negative control (non-transfected 293T supernatant), PP6373-OKT3, OKT3-PP6373 or FIT-Ig for 12 hours. Cytokines (IFNr, TNF, IL10, IL6, IL4 and IL2) in tissue culture media were measured by flow cytometry. Three independent experiments were performed.
Figure 21:
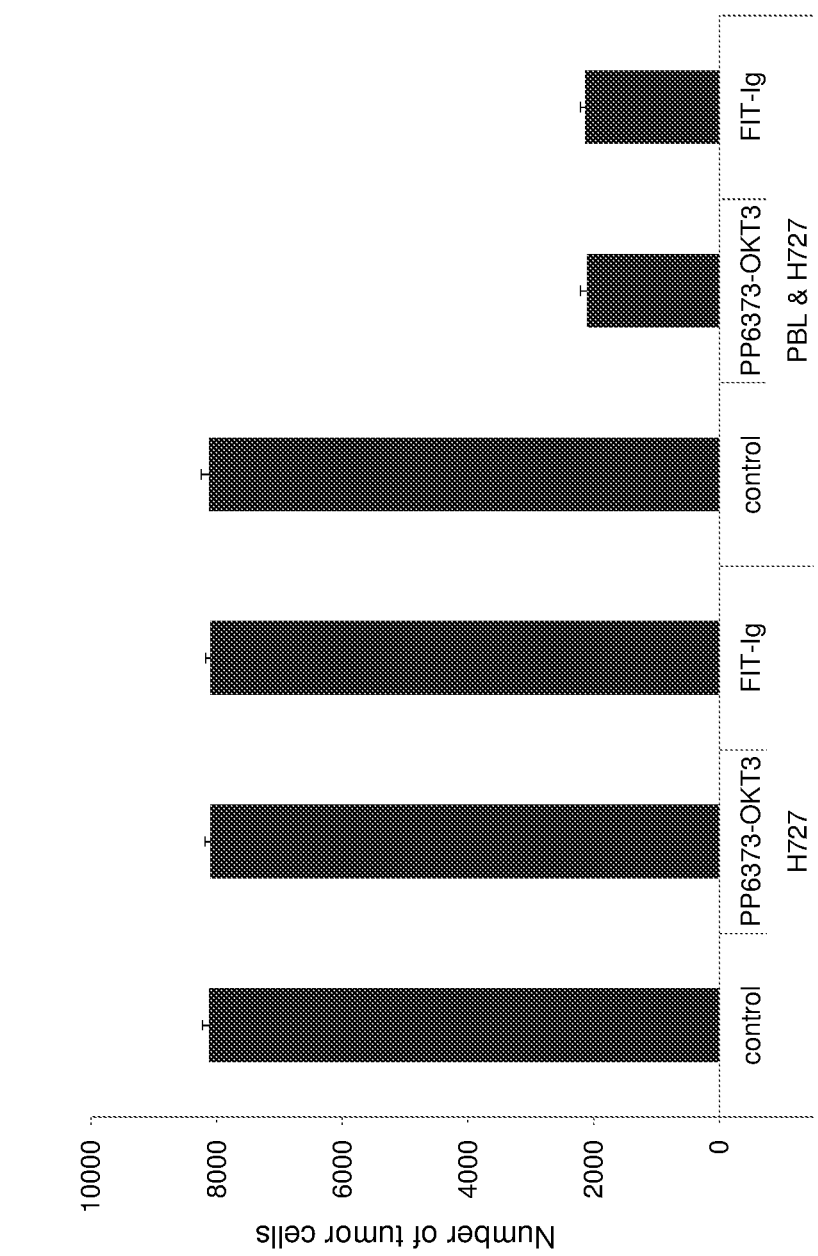
FIG. 21. Flow cytometry analysis indicates FIT-Ig induces cytotoxicity of tumor cells by T cells. Lung cancer cell H727 and activated human T cells were incubated at 1:5 with negative control (non-transfected 293T supernatant), PP6373-OKT3, OKT3-PP6373 or FIT-Ig for 12 hours. Lung cancer cells and human T cells were collected and stained with anti-human CD45 and live/dead reagent Aqua. Tumor cells number was plotted as double negative of anti-CD45 and Aqua. Three independent experiments were performed.
Figure 22:
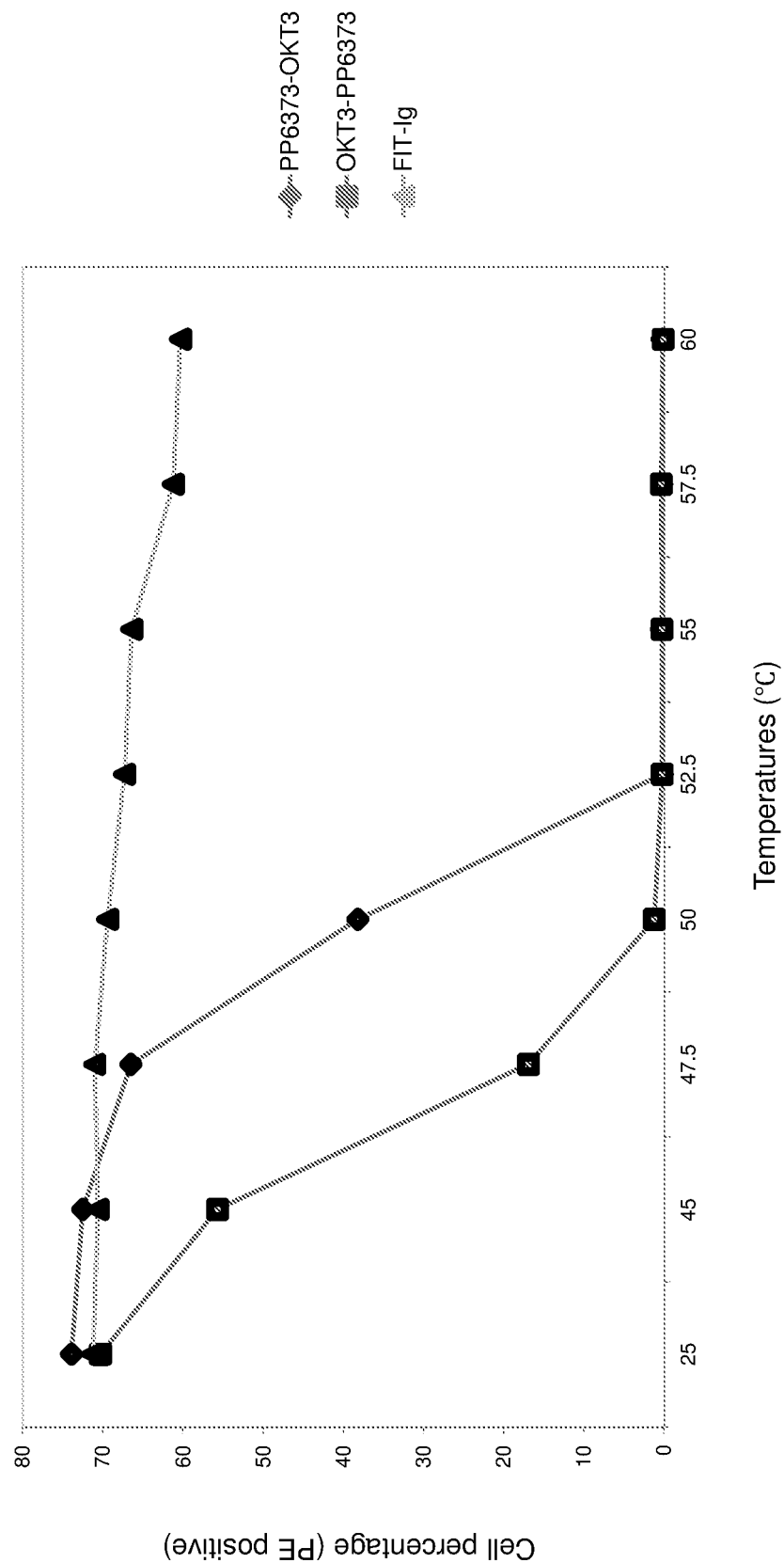
FIG. 22. Flow cytometry analysis indicates FIT-Ig has higher thermal stability than PP6373-OKT3 and OKT3-PP6373. All bispecific antibodies PP6373-OKT3, OKT3-PP6373 and FIT-Ig were incubated at the indicated temperature for 20 min, and the supernatants after spinning at 14000 g for 5 min were used for Jurkat cells staining. Then biotinylated SA-N-CD24 protein was incubated with Jurkat cells and PE-Steptavidin signal was measured by flow cytometry.

As yet another embodiment, the bispecific antibody can be produced by a FIT-Ig technology. Briefly, bispecific antibody is formed by co-expression of three constructs encoding $VL_{6373}$-CL-$VH_{OKT3}$-CH1-Fc (SEQ ID NO: 25), $VH_{6373}$-CH1 (SEQ ID NO: 26), and $VL_{OKT3}$-CL (SEQ ID NO: 27), respectively. As shown in FIG. 19, the FIT-Ig antibody showed good bispecific binding activities for both OKT3 and SA-N-CD24. In addition to binding, we also found that this bispecific antibody induced significant cytokine response (FIG. 20) and cytotoxicity toward tumor cells (FIG. 21). Additionally, this bispecific antibody (FIT-Ig) showed higher thermal stability as compared with previous bispecific antibodies PP6373-OKT3 and OKT3-PP6373 (FIG. 22).

Example 7

Figure 23:
FIG. 23. Schematic of CarT construct comprising anti-CD24-scFv.

Use of PP6373 for Chimeric Antigen Receptor (CAR)-Modified T Cells (CAR-T) for Cancer Therapy The anti-CD24 antibodies react with a broad-spectrum of cancer cells and can be used to produce a chimeric antigen receptor to confer anti-cancer activity to T cells. In one embodiment, the PP6373 single chain Fv sequence (SEQ ID NO:28) or other anti-CD24 mAb single chain (alphaCD24SC) is inserted into a CAR-T vector known in the art, as diagramed in FIG. 23. The construct is then inserted into gene vectors known in the art, including those derived from retrovirus, lentivirus, adeno-associated virus or adenoviral vectors.

To test the activity of the CAR, PBMCs from healthy donor were enriched for T cells by using Pan T Cell Isolation Kit, human (Miltenyl Biotec) (Day 0). Human pan T cells were stimulated with anti-CD3 and anti-CD28 for 24 hours and cultured with IL-2 for 2 days. Activated T cells were mock treated (control T) or infected with lenti-virus carrying CD24-CAR (Day 2). To test the anti-tumor activity of the CAR-T, control T cells or CD24 CAR-T cells were co-cultured with CellTrace Violet (Thermo Fisher) labeled tumor cells overnight. Lysis of tumor cells was measured by staining with Fixable Viability Dye eFluor™ 660 (eBioscience) and calculated with the formula:

Lysis %=(Dead %−autolysis %)/(1−autolysis %)

Figure 24:
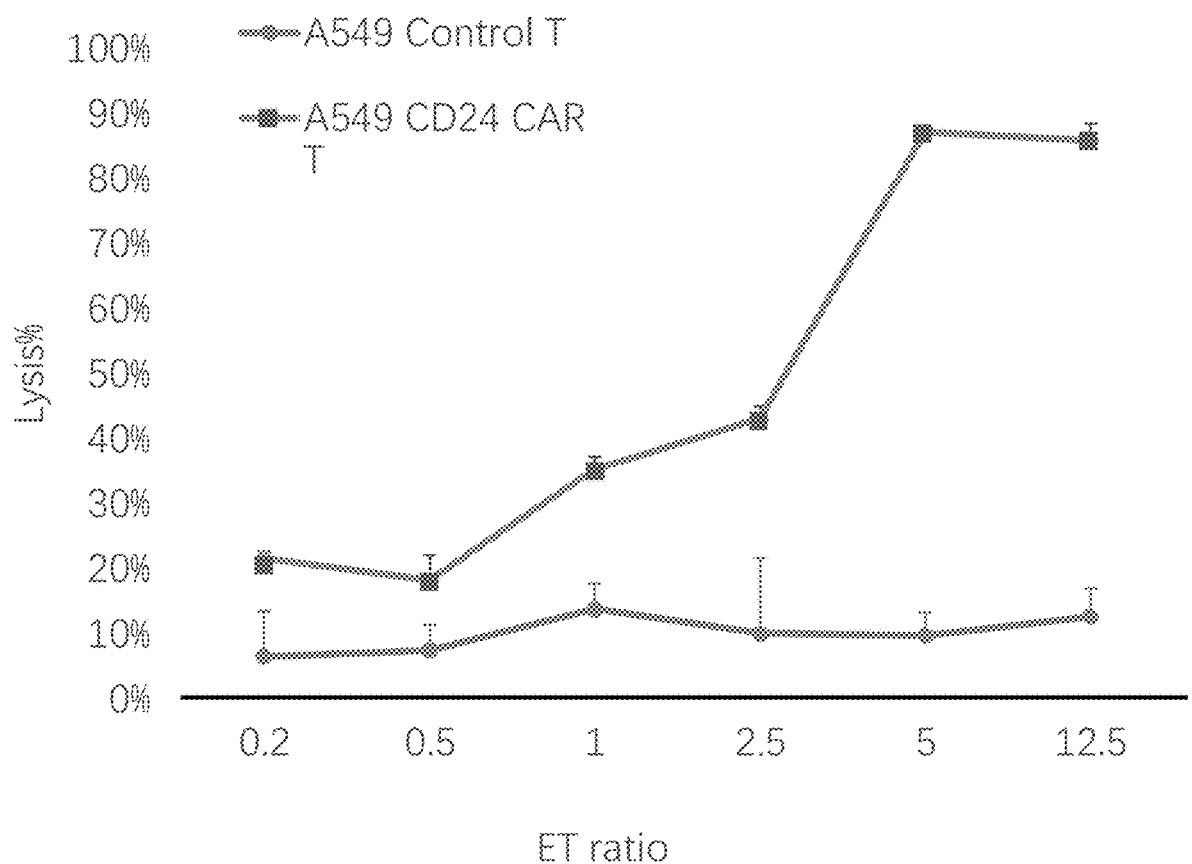
FIG. 24. Plot of CD24 CART induced cytotoxicity for lung cancer cell line A549.

As shown in FIG. 24, over a wide-range of effector to target ratio (E/T), the CD24 CAR-T shows potent cytotoxicity over lung cancer cell line A549.

Figure 25:
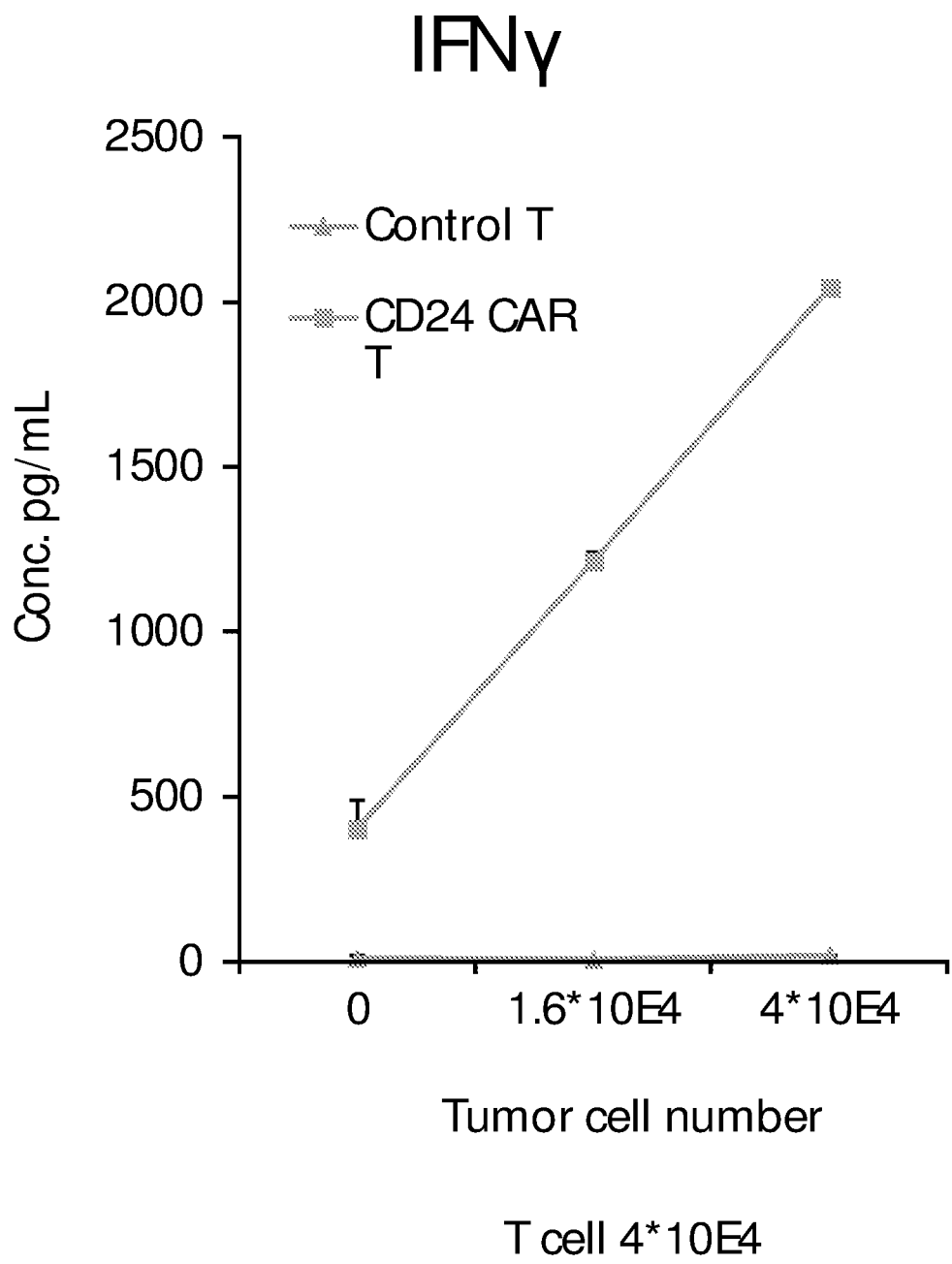
FIG. 25. Plot of CART activation by tumor cell line as demonstrated by production of IFNγ.

To test if the CAR-T is activated by cancer cells, we incubated $4\times10^4$ CAR-T or control T cells with A549 tumor cells overnight and measured IFNγ in the supernatants. As shown in FIG. 25, CAR-T but not control T cells produced IFNγ in response to A549 tumor cell stimulation.

Figure 26:
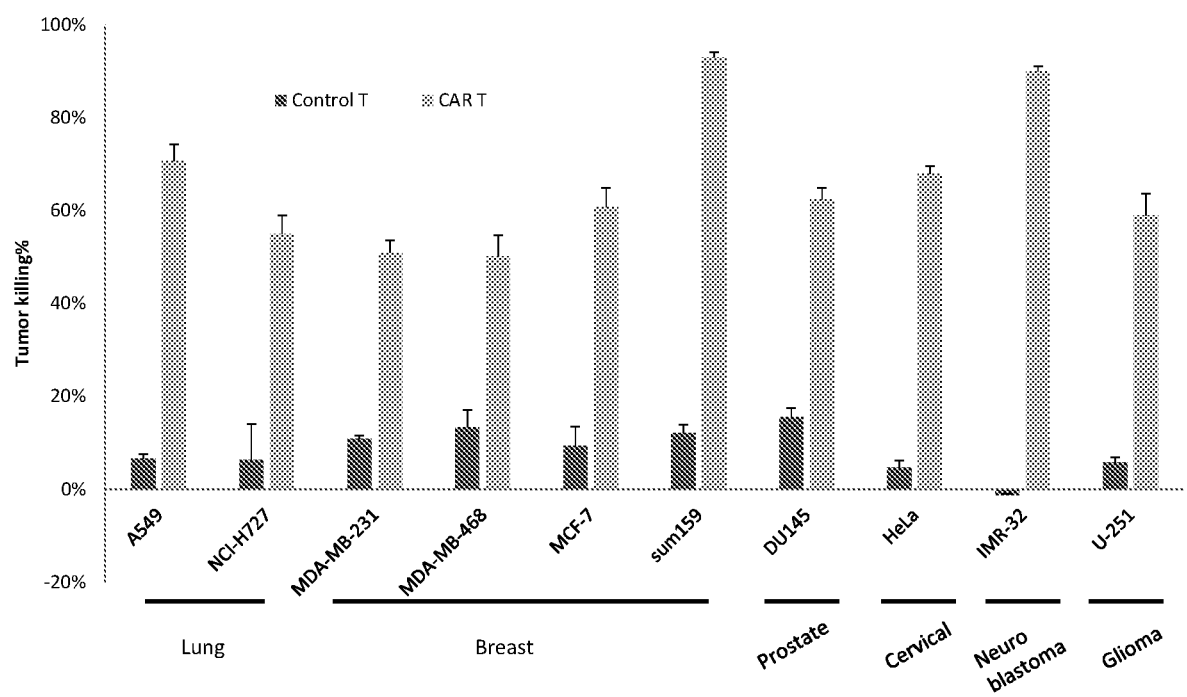
FIG. 26. Bar plot of anti-tumor activity of CD24 CART against various tumor types. The E/T ratio for the data presented is 5.

Since CD24 is broadly expressed among multiple lineages of cancer types. As shown in FIG. 26, CD24 CAR-T exhibits broad cytotoxicity against many cancer types, including lung cancer, breast cancer, prostate cancer, cervical cancer, neuroblastoma, and glioma.

Taken together, our data demonstrate that a CD24 CAR-T based on our antibody have great potential in cancer treatment. The types of cancer that can be targeted include but not limited to, brain tumors, head and neck cancer, sarcoma, lung cancer, gastrointestinal cancer, breast cancer, testicular cancer, prostate cancer, pancreatic cancer, liver cancer or hematological malignancies.

Example 8

Humanization of PP6373 for Cancer Therapy

Figure 27:
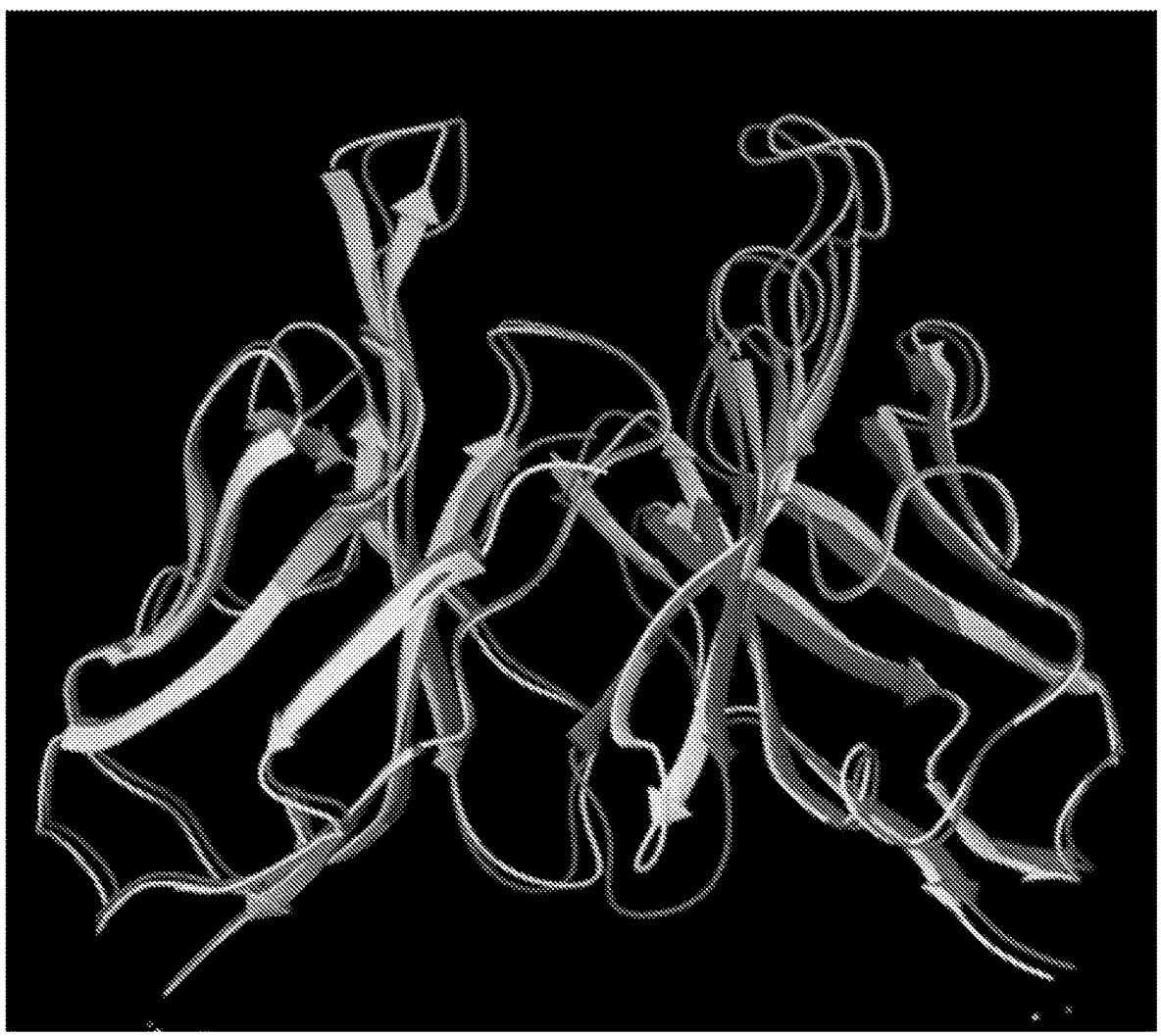
FIG. 27. Ribbon diagram of three dimensional structural alignment of chimeric PP6373 (FR: white, CDR: light gray) and huVHv1VLv1 (FR: gray, CDR: dark gray).

A PP6373 Fv homology model was built up by using the structure of pdb 4PB0 as the model structure. Both VH and VL share >90% homology to that of 4PB0. Upon querying a human Ig database, human germline V region sequence IGHV3-73*01 and J region sequence IGHJ4*01 were identified as suitable structures and were used as the human acceptor framework for the CDR regions of the heavy chain (Onc-1 VH). Human germline V region IGKV2-29*02 and J region sequence IGKJ4*01 were applied as the human acceptor framework for CDR regions of the light chain (Onc-1 VL). Four VH and four VL sequences were designed (SEQ ID NOS: 29-36). The new products improve humanization scores from 73% to >83% in VH and from 80% to >83% in VL. Structural alignment of PP6373 murine Fv, and the Fv of a humanized version PP6373 (hu-VHv1VLv1; SEQ ID NOS: 29 and 33) demonstrated a high degree of similarity (FIG. 27).

Figure 28:
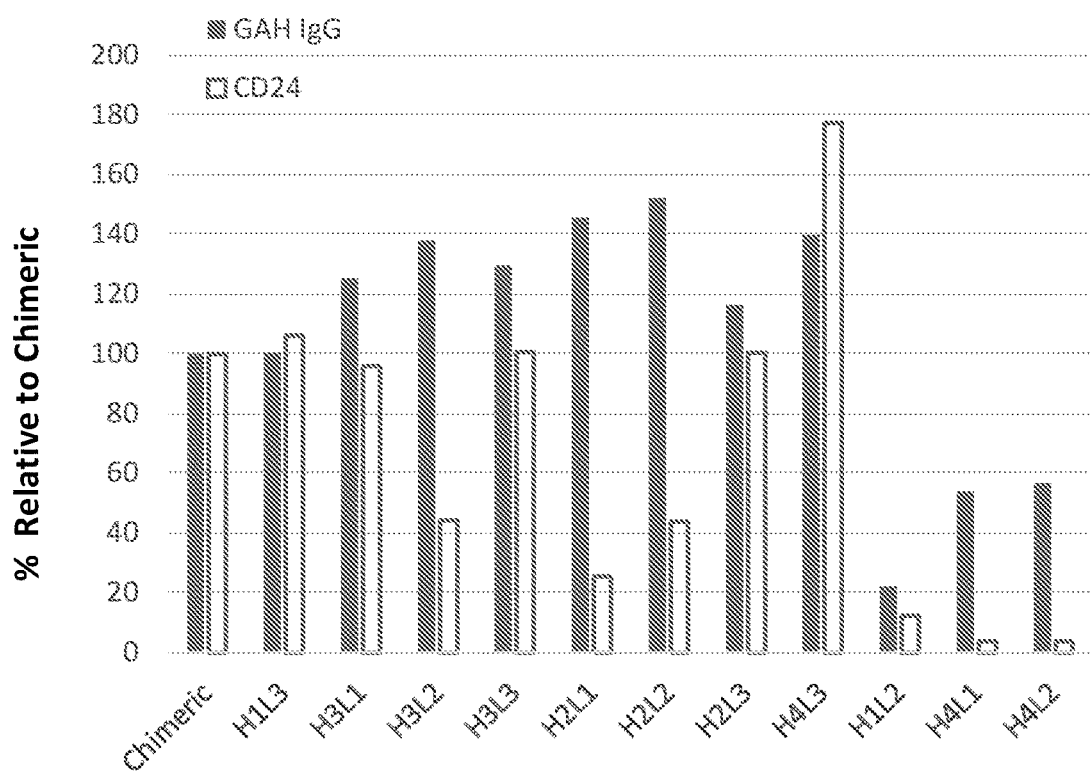
FIG. 28. Plot of relative effectiveness of different antibody pairs for expression and binding to CD24-GST.

To select the best working combination of HuVH and HuVL for CD24 binding, different combinations were co-transfected into 293 cells for 72 hrs. Two ELISAs are then performed with expression media. ELISA 1: a 96 well plate was coated with purified goat-anti-human polyclonal IgG (GAH) and, after blocking, expression media or purified control IgGs were added, and goat-anti-human IgG-HRP was used as detection antibody. ELISA 2: a 96 well plate was coated with CD24-GST protein and, after blocking, expression media or purified control IgGs were added, and goat-anti-human IgG-HRP was used as detection antibody. If binding of the chimeric PP6373 antibody is considered to be 100% in both ELISAs, the various VH & VL combinations exhibiting differing degrees of binding will be compared to that of chimeric antibody and ranked by relative binding (leads selected from pre-screen will be compared again after purification). The first round pre-screening data are summarized in FIG. 28 and the data of this experiment suggested that, a) L3 showed high binding capacity per unit protein that made L3 a lead; and b) H1L3 (SEQ ID NOS: 29 and 35), H2L3 (SEQ ID NOS: 30 and 35), H3L3 (SEQ ID NOS 31 and 35 and H4L3 (SEQ ID NOS: 32 and 35) are the four humanization leads for PP6373.

Figure 29:
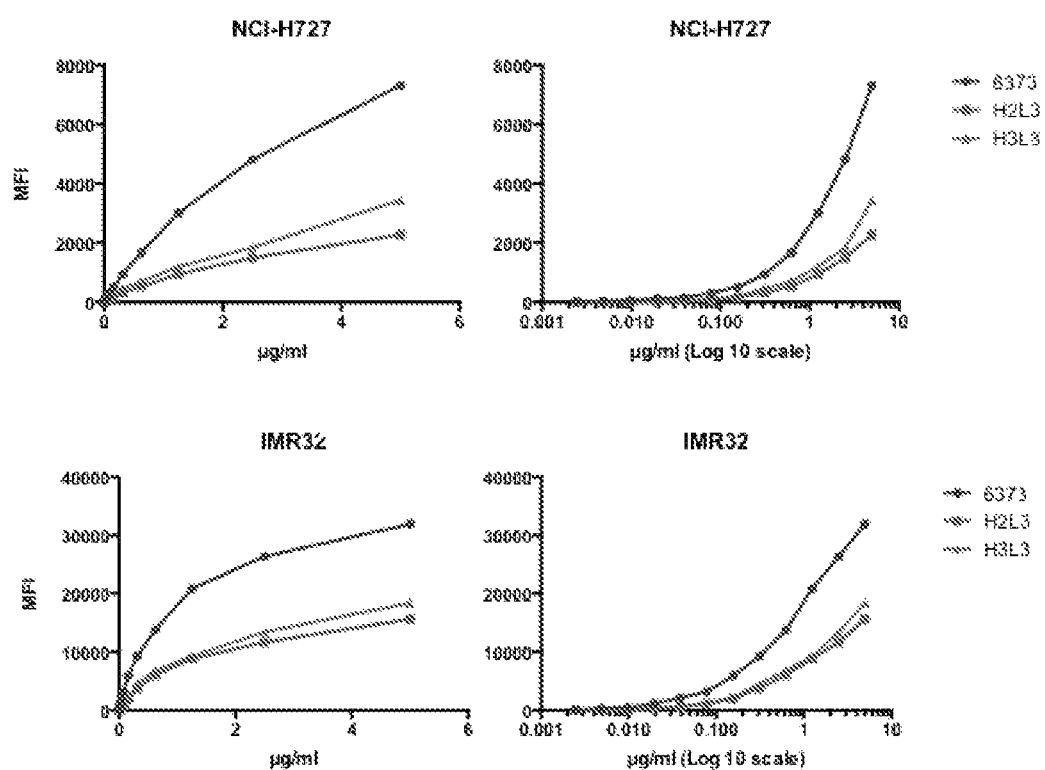
FIG. 29. Plot of H2L3 and H3L3 binding to human cancer cell lines NCI-H727 (top) and IMR32 (bottom). Data shown are mean fluorescence intensity when a wide range of antibodies were used.

To test if the lead antibodies H2L3 and H3L3 retain their ability to bind tumor cells, we biotinylated the humanized antibodies along with PP6373. As shown in FIG. 29, although PP6373 had better binding to two human cancer cells tested, both H2L3 and H3L3 exhibit strong binding with $IC_{50}$ in the nM range.

Figure 30:
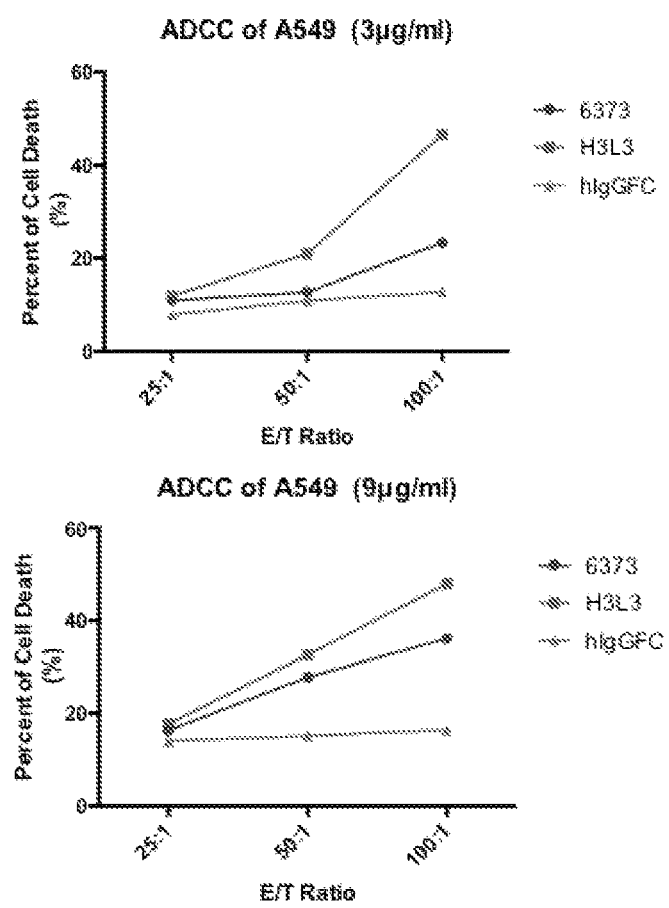
FIG. 30. Cell death plots indicate that at low concentration HL33 is more potent than PP6373 in ADCC. Lung cancer cell line A549 was used as target, while human PBL were used as effectors. The dose of antibodies used was 3 µg/ml (top panel) or 9 µg/ml (bottom panel).
Figure 31:
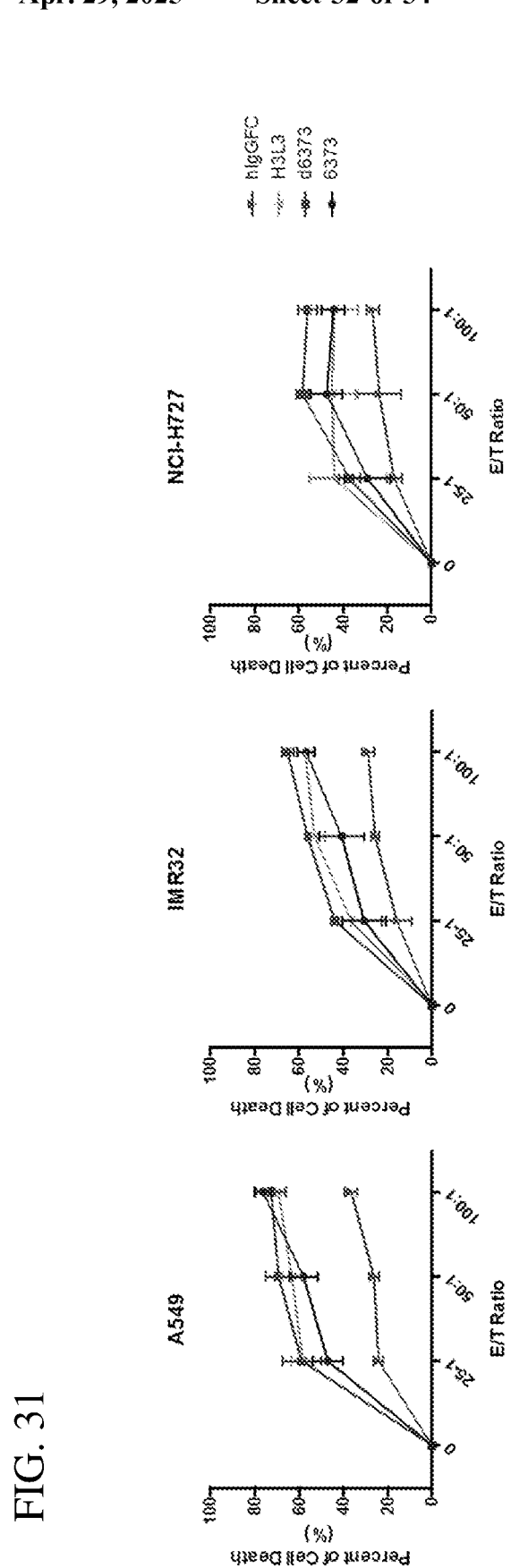
FIG. 31. Cell death plots indicate H3L3 confers potent ADCC activity to multiple tumor cell lines, including lung cancer cell lines A549 and NCI-H727 and neuroblastoma cell line IMR-32. Human PBMC was used as effector cells.
Figure 32:
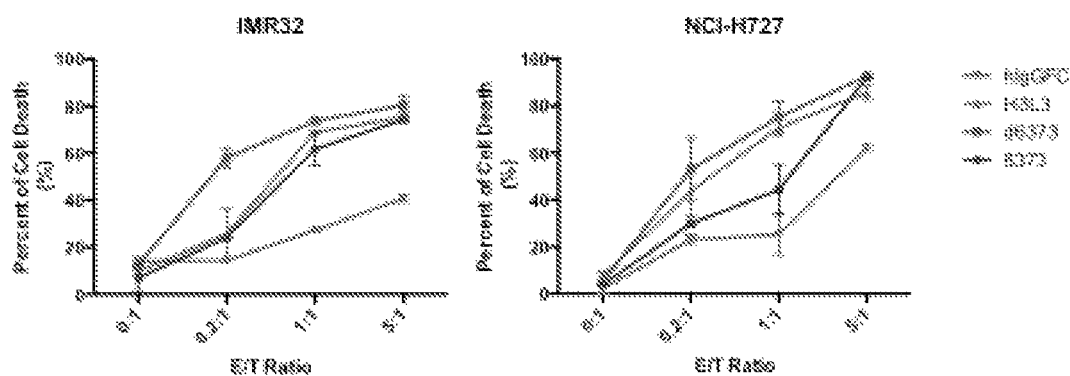
FIG. 32. Cell death plots indicate H3L3 confers potent ADCC activity to multiple tumor cell lines, including lung cancer cell lines A549 and NCI-H727 and neuroblastoma cell line IMR-32. NK cells purified from human PBMC are used as effector cells.

We performed ADCC assays using either PBL (FIG. 30, FIG. 31) or purified NK cells (FIG. 32) from PBL as effectors, and A549 cells as target cells. Surprisingly, although H2L3 and H3L3 binds less well to tumor cells (FIG. 29), they are more potent effectors in ADCC when low concentration of antibody is used (FIG. 30). As expected, defucosylated PP6373 (d6373) is more potent in ADCC (FIG. 31, FIG. 32).

Taken together, our data demonstrated that humanized clones of PP6373 exhibit significant binding to human cancer cells and surprisingly potent ADCC activity. In one embodiment, the antibodies can be used to treat cancer. In another embodiment, the humanized antibody can be used as a key component of a bispecific antibody. To explore this activity, we generated two constructs containing H3 and L3 to produce FIT-Ig technology based bispecific antibodies. The sequences for the humanized FIT-Ig antibodies are listed in Seq ID-37 and 38, and are used in conjunction with SEQ ID NO: 27. Additionally, we also made some mutations to optimize humanized FIT-Ig sequences and they were listed in Seq ID-39-41. Specifically: all three sequences comprise a signal sequence on the N terminal end for protein purification and synthesis; in Seq ID-39: a mutation (D to A) was introduced into the Fc region to prevent ADCC; in Seq ID-27, there is one extra R between VLOKT3 and CL which was induced by restriction enzyme site during construction and in Seq ID-41, the extra R was deleted.

In yet another embodiment, humanized antibodies can be used as a key component of CAR-T for cancer therapy, using methods known in the art.

Example 9

Anti-CD24 Antibodies with Glycan-Shielded Epitopes do not Bind to Normal Cells with High Expression of CD24

Figure 33:
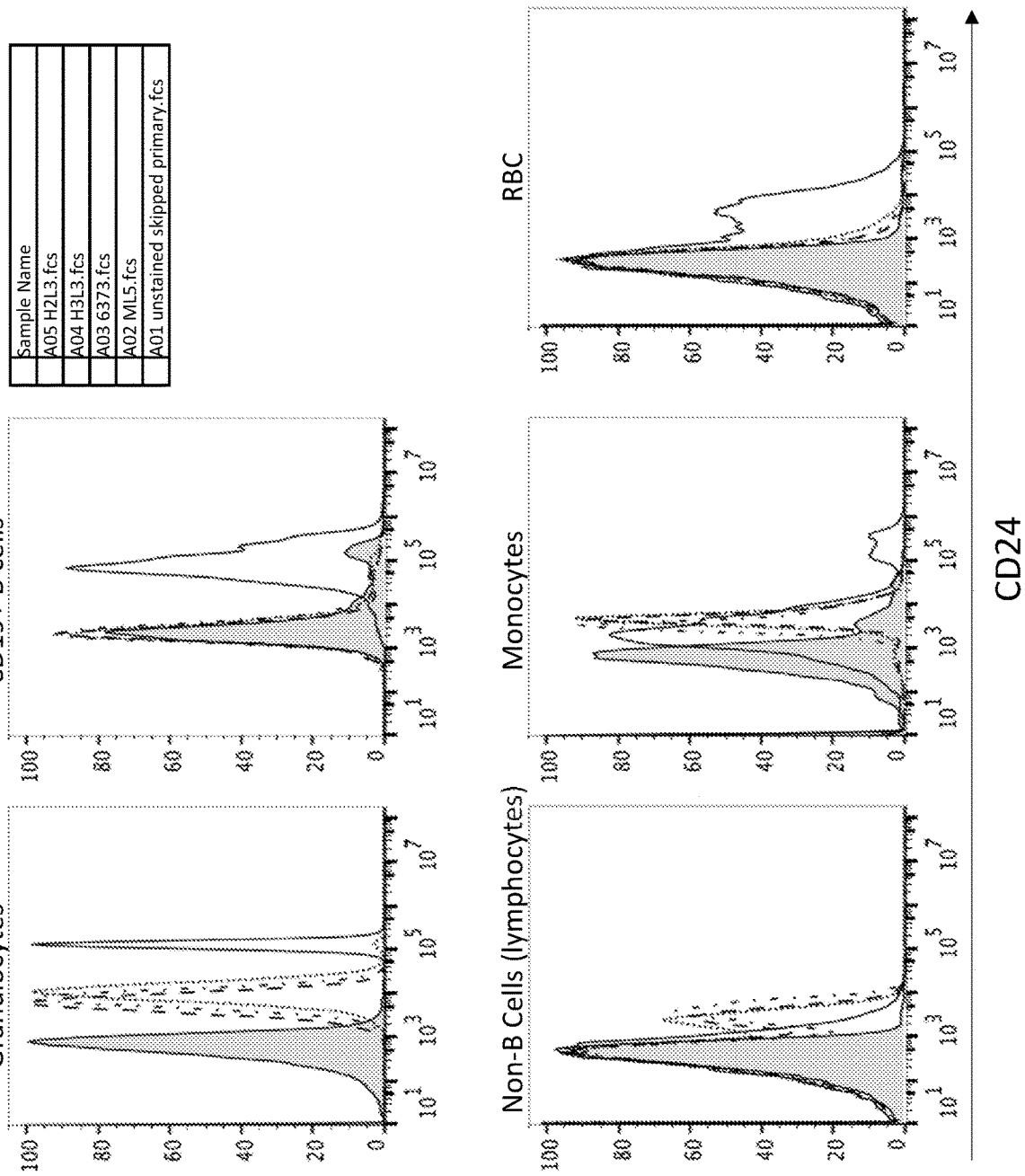
FIG. 33. Flow cytometry analysis indicates antibodies that recognized glycan shielded epitope do not recognize B cells, red blood cells, and interact poorly with neutrophils.

A key requirement of antibody-based immunotherapy is minimal reactivity to normal tissues. Since CD24 is abundantly expressed on hematopoietic cells, especially granulocytes, B cells, part of red blood cells and part of monocytes, we compared PP6373 and its two humanized clones, H2L3 and H3L3, with conventional anti-CD24 mAb, ML5. As shown in FIG. 33, while ML5 shows strong binding to cells that normally express high levels of CD24, H2L3 and H3L3 do not bind to B cells and red blood cells, and bind poorly to granulocytes. This result demonstrates minimal binding to other cells types such as macrophages, and a fraction of non-B lymphocytes.

The invention claimed is:

1. An anti-CD24 antibody comprising (a) a heavy chain variable region comprising the sequence set forth in SEQ ID NO: 31 or 30 and a light chain variable region comprising the sequence set forth in SEQ ID NO: 35; or (b) a heavy chain variable region from the sequence set forth in SEQ ID NO: 6 and a light chain variable region from the sequence set forth in SEQ ID NO: 16.

2. The anti-CD24 antibody of claim 1, further comprising a human immunoglobulin constant (Fc) region.

3. The anti-CD24 antibody of claim 1, wherein the anti-CD24 antibody comprises the heavy chain variable region from the sequence set forth in SEQ ID NO: 6 and the light chain variable region from the sequence set forth in SEQ ID NO: 16.

4. The anti-CD24 antibody of claim 1, wherein the anti-CD24 antibody comprises the heavy chain variable region comprising the sequence set forth in SEQ ID NO: 30 and the light chain variable region comprising the sequence set forth in SEQ ID NO: 35.

5. The anti-CD24 antibody of claim 1, wherein the anti-CD24 antibody comprises the heavy chain variable region comprising the sequence set forth in SEQ ID NO: 31 and the light chain variable region comprising the sequence set forth in SEQ ID NO: 35.

6. A bi-specific antibody comprising a first antibody domain comprising the anti-CD24 antibody of claim 1, and a second antibody domain comprising a second antibody or antigen binding fragment thereof, wherein the bi-specific antibody comprises the sequences set forth in SEQ ID NOs: 17 and 18, or any one of the sequence set forth in SEQ ID NOs: 23-27 and 37-41.

7. A chimeric antigen receptor, comprising a single chain antibody comprising the anti-CD24 antibody of claim 1.

8. The chimeric antigen receptor of claim 7, comprising the sequence set forth in SEQ ID NO: 28.

9. A composition comprising the anti-CD24 antibody of claim 1, and a second anti-cancer therapy.

10. A method of reducing growth of a cancer in a patient in need thereof, comprising administering the anti-CD24 antibody of claim 1 to the patient, wherein cells of the cancer express CD24.

11. The method of claim 10, wherein the cancer is lung cancer, ovarian cancer, breast cancer, liver cancer, brain cancer, cervical cancer, renal cancer, testicular cancer, prostate cancer, or neuroblastoma.

12. The method claim 10, wherein the anti-CD24 antibody comprises the heavy chain variable region comprising the sequence set forth in SEQ ID NO: 31 and the light chain variable region comprising the sequence set forth in SEQ ID NO: 35.

13. The method of claim 10, wherein the anti-CD24 antibody comprises the heavy chain variable region comprising the sequence set forth in SEQ ID NO: 30 and the light chain variable region comprising the sequence set forth in SEQ ID NO: 35.

* * * * *

SEQUENCE LISTING

```
<160> NUMBER OF SEQ ID NOS: 49

<210> SEQ ID NO 1
<211> LENGTH: 468
<212> TYPE: PRT
<213> ORGANISM: Artificial Sequence
<220> FEATURE:
<223> OTHER INFORMATION: Antibody 3B6 heavy chain 4040

<400> SEQUENCE: 1

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Ser
    50                  55                  60

Pro Glu Lys Gly Leu Glu Trp Val Ala Glu Ile Arg Asp Lys Thr Lys
65                  70                  75                  80

Asn Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

Arg Thr Glu Asp Thr Gly Ile Tyr Tyr Cys Thr Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

```
Thr Val Pro Ser Ser Ser Leu Gly Thr Gln Thr Tyr Ile Cys Asn Val
        210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly
465

<210> SEQ ID NO 2
<211> LENGTH: 239
<212> TYPE: PRT
<213> ORGANISM: Artificial Sequence
<220> FEATURE:
<223> OTHER INFORMATION: Antibody 3B6 light chain 4040

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
                20                  25                  30

Val Thr Ile Gly Gln Pro Ala Ser Ile Ser Cys Lys Ser Gln Ser
            35                  40                  45

Leu Leu Tyr Ser Asn Gly Lys Thr Tyr Leu Asn Trp Leu Gln Gln Arg
    50                  55                  60

Pro Gly Gln Ser Pro Lys Arg Leu Ile Tyr Gln Val Ser Lys Leu Asp
65                  70                  75                  80

Pro Gly Ile Pro Asp Arg Phe Ser Gly Ser Gly Ser Glu Thr Asp Phe
                85                  90                  95
```

```
Thr Leu Lys Ile Ser Arg Val Glu Ala Glu Asp Leu Gly Ile Tyr Tyr
            100                 105                 110

Cys Leu Gln Gly Thr Ser Tyr Pro Trp Thr Phe Gly Gly Gly Thr Lys
            115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 3
<211> LENGTH: 468
<212> TYPE: PRT
<213> ORGANISM: Artificial Sequence
<220> FEATURE:
<223> OTHER INFORMATION: Affinity matured heavy chain 4041

<400> SEQUENCE: 3

```
Met Asp Pro Lys Gly Ser Leu Ser Trp Arg Ile Leu Phe Leu Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Ala Phe Ser Gly Ala Trp Met Asp Trp Val Arg Gln Ser
    50                  55                  60

Pro Glu Lys Gly Leu Glu Trp Val Ala Glu Ile Arg Asp Lys Thr Lys
65                  70                  75                  80

Asn Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

Arg Thr Glu Asp Thr Gly Val Tyr Tyr Cys Thr Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220
```

Asn His Lys Pro Ser Asn Thr Lys Val Asp Lys Val Glu Pro Lys
225                 230                 235                 240

Ser Cys Asp Lys Thr His Thr Cys Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly
465

<210> SEQ ID NO 4
<211> LENGTH: 468
<212> TYPE: PRT
<213> ORGANISM: Artificial Sequence
<220> FEATURE:
<223> OTHER INFORMATION: Affinity matured heavy chain 4042

<400> SEQUENCE: 4

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Ser
    50                  55                  60

Pro Glu Lys Gly Leu Glu Trp Val Ala Glu Ile Arg Asp Lys Ser Thr
65                  70                  75                  80

Asn Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

```
Arg Thr Glu Asp Thr Gly Ile Tyr Tyr Cys Thr Gly Ala Met Asp Tyr
            115                 120                 125

Trp Gly Gln Gly Thr Ser Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
    275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
    450                 455                 460

Leu Ser Pro Gly
465

<210> SEQ ID NO 5
<211> LENGTH: 468
<212> TYPE: PRT
<213> ORGANISM: Artificial Sequence
<220> FEATURE:
<223> OTHER INFORMATION: Affinity matured heavy chain 4043

<400> SEQUENCE: 5
```

```
Met Asp Pro Lys Gly Ser Leu Ser Trp Arg Ile Leu Leu Phe Leu Ser
1               5                   10                  15
Leu Ala Phe Glu Leu Ser Tyr Gly Glu Val Lys Phe Glu Glu Ser Gly
            20                  25                  30
Gly Gly Leu Val Gln Pro Gly Gly Ser Ile Lys Leu Ser Cys Ala Ala
            35                  40                  45
Ser Gly Val Thr Phe Ser Glu Ala Trp Met Asp Trp Val Arg Gln Ser
50                  55                  60
Pro Glu Lys Gly Leu Glu Trp Val Ala Glu Ile Arg Asp Asn Thr Thr
65                  70                  75                  80
Asn Tyr Val Thr Tyr Tyr Ala Glu Ser Val Lys Gly Arg Phe Thr Ile
                85                  90                  95
Ser Arg Asp Asp Ser Lys Ser Arg Val Tyr Leu Gln Met Asn Asn Leu
            100                 105                 110
Arg Thr Glu Asp Thr Gly Ile Tyr Tyr Cys Thr Gly Ala Met Asp Tyr
            115                 120                 125
Trp Gly Gln Gly Thr Ser Val Thr Val Ser Ser Ala Ser Thr Lys Gly
            130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Gln Thr Tyr Ile Cys Asn Val
210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
            275                 280                 285
Ser His Glu Asp Pro Glu Val Lys Phe Asn Trp Tyr Val Asp Gly Val
290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
            355                 360                 365
Gln Val Tyr Thr Leu Pro Pro Ser Arg Asp Glu Leu Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
```

```
                    420                 425                 430
Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly
465

<210> SEQ ID NO 6
<211> LENGTH: 468
<212> TYPE: PRT
<213> ORGANISM: Artificial Sequence
<220> FEATURE:
<223> OTHER INFORMATION: Affinity matured heavy chain 4069 (PP6373)

<400> SEQUENCE: 6

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Ser
    50                  55                  60

Pro Glu Lys Gly Leu Glu Trp Val Ala Glu Ile Arg Asp Lys Pro Asn
65                  70                  75                  80

Ser Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

Arg Thr Glu Asp Thr Gly Ile Tyr Tyr Cys Thr Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
```

```
            305                 310                 315                 320
        Thr Tyr Arg Val Val Ser Val Leu Thr Val Leu His Gln Asp Trp Leu
                        325                 330                 335
        Asn Gly Lys Glu Tyr Lys Cys Lys Val Ser Asn Lys Ala Leu Pro Ala
                        340                 345                 350
        Pro Ile Glu Lys Thr Ile Ser Lys Ala Lys Gly Gln Pro Arg Glu Pro
                        355                 360                 365
        Gln Val Tyr Thr Leu Pro Pro Ser Arg Asp Glu Leu Thr Lys Asn Gln
                370                 375                 380
        Val Ser Leu Thr Cys Leu Val Lys Gly Phe Tyr Pro Ser Asp Ile Ala
        385                 390                 395                 400
        Val Glu Trp Glu Ser Asn Gly Gln Pro Glu Asn Asn Tyr Lys Thr Thr
                        405                 410                 415
        Pro Pro Val Leu Asp Ser Asp Gly Ser Phe Phe Leu Tyr Ser Lys Leu
                        420                 425                 430
        Thr Val Asp Lys Ser Arg Trp Gln Gln Gly Asn Val Phe Ser Cys Ser
                        435                 440                 445
        Val Met His Glu Ala Leu His Asn His Tyr Thr Gln Lys Ser Leu Ser
                450                 455                 460
        Leu Ser Pro Gly
        465

<210> SEQ ID NO 7
<211> LENGTH: 468
<212> TYPE: PRT
<213> ORGANISM: Artificial Sequence
<220> FEATURE:
<223> OTHER INFORMATION: Affinity matured heavy chain H4070

<400> SEQUENCE: 7

Met Asp Pro Lys Gly Ser Leu Ser Trp Arg Ile Leu Leu Phe Leu Ser
        1               5                   10                  15
        Leu Ala Phe Glu Leu Ser Tyr Gly Glu Val Lys Phe Glu Glu Ser Gly
                        20                  25                  30
        Gly Gly Leu Val Gln Pro Gly Gly Ser Ile Lys Leu Ser Cys Ala Ala
                        35                  40                  45
        Ser Gly Val Pro Phe Ser Gly Ala Trp Met Asp Trp Val Arg Gln Ser
                50                  55                  60
        Pro Glu Lys Gly Leu Glu Trp Val Ala Glu Ile Arg Asp Lys Thr Lys
        65                  70                  75                  80
        Asn Tyr Val Thr Tyr Tyr Ala Glu Ser Val Lys Gly Arg Phe Thr Ile
                        85                  90                  95
        Ser Arg Asp Asp Ser Lys Ser Arg Val Tyr Leu Gln Met Asn Asn Leu
                        100                 105                 110
        Arg Thr Glu Asp Thr Gly Ile Tyr Tyr Cys Thr Gly Ala Met Asp Tyr
                        115                 120                 125
        Trp Gly Gln Gly Thr Ser Val Thr Val Ser Ser Ala Ser Thr Lys Gly
                130                 135                 140
        Pro Ser Val Phe Pro Leu Ala Pro Ser Ser Lys Ser Thr Ser Gly Gly
        145                 150                 155                 160
        Thr Ala Ala Leu Gly Cys Leu Val Lys Asp Tyr Phe Pro Glu Pro Val
                        165                 170                 175
        Thr Val Ser Trp Asn Ser Gly Ala Leu Thr Ser Gly Val His Thr Phe
                        180                 185                 190
        Pro Ala Val Leu Gln Ser Ser Gly Leu Tyr Ser Leu Ser Ser Val Val
```

195                 200                 205
Thr Val Pro Ser Ser Leu Gly Thr Gln Thr Tyr Ile Cys Asn Val
        210                 215                 220
Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 8
<211> LENGTH: 468
<212> TYPE: PRT
<213> ORGANISM: Artificial Sequence
<220> FEATURE:
<223> OTHER INFORMATION: Affinity matured heavy chain 4071

<400> SEQUENCE: 8

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Ser
    50                  55                  60

Pro Glu Lys Gly Leu Glu Trp Val Ala Glu Ile Arg Asp Lys Thr Lys
65                  70                  75                  80

Asn Tyr Val Thr Tyr Tyr Ala Glu Ser Val Lys Gly Arg Phe Thr Ile

```
            85                  90                  95
Ser Arg Asp Asp Ser Lys Gly Arg Val Tyr Leu Gln Met Asn Asn Leu
            100                 105                 110

Arg Thr Glu Asp Thr Gly Ile Tyr Tyr Cys Thr Gly Ala Met Asp Tyr
            115                 120                 125

Trp Gly Gln Gly Thr Ser Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 9
<211> LENGTH: 468
<212> TYPE: PRT
<213> ORGANISM: Artificial Sequence
```

-continued

<220> FEATURE:
<223> OTHER INFORMATION: Affinity matured heavy chain 4072

<400> SEQUENCE: 9

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Thr
    50                  55                  60

Pro Glu Lys Gly Leu Glu Trp Val Ala Glu Ile Arg Asp Arg Glu Thr
65                  70                  75                  80

Lys Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

Arg Thr Glu Asp Thr Gly Ile Tyr Tyr Cys Thr Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400
```

```
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 10
<211> LENGTH: 468
<212> TYPE: PRT
<213> ORGANISM: Artificial Sequence
<220> FEATURE:
<223> OTHER INFORMATION: Affinity matured heavy chain 4073

<400> SEQUENCE: 10

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Phe Glu Glu Ser Gly
            20                  25                  30

Gly Gly Leu Val Gln Pro Gly Gly Ser Ile Lys Leu Ser Cys Ala Ala
        35                  40                  45

Ser Gly Val Thr Phe Ser Glu Ala Trp Met Asp Trp Val Arg Gln Ser
    50                  55                  60

Pro Glu Lys Gly Leu Glu Trp Val Ala Glu Ile Arg Asp Lys Gln Asn
65                  70                  75                  80

Glu Tyr Val Thr Tyr Tyr Ala Glu Ser Val Lys Gly Arg Phe Thr Ile
                85                  90                  95

Ser Arg Asp Asp Ser Lys Ser Arg Val Tyr Leu Gln Met Asn Asn Leu
            100                 105                 110

Arg Thr Glu Asp Thr Gly Ile Tyr Tyr Cys Thr Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly
465

<210> SEQ ID NO 11
<211> LENGTH: 239
<212> TYPE: PRT
<213> ORGANISM: Artificial Sequence
<220> FEATURE:
<223> OTHER INFORMATION: Affinity matured light chain 4041

<400> SEQUENCE: 11

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Ile Gly Gln Pro Ala Ser Ile Ser Cys Lys Ser Ser Gln Ser
        35                  40                  45

Leu Leu Tyr Ser Asn Gly Lys Thr Tyr Leu Asn Trp Leu Gln Gln Arg
    50                  55                  60

Pro Gly Gln Ser Pro Lys Arg Leu Ile Tyr Gln Val Ser Lys Leu Asp
65                  70                  75                  80

Pro Gly Thr Pro Asp Arg Phe Ser Gly Ser Gly Ser Glu Thr Asp Phe
            85                  90                  95

Thr Leu Lys Ile Ser Arg Val Glu Ala Glu Asp Leu Gly Ile Tyr Tyr
        100                 105                 110

Cys Met Gln Gly Thr Ser Thr Pro Trp Thr Phe Gly Gly Gly Thr Lys
    115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175
```

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 12
<211> LENGTH: 239
<212> TYPE: PRT
<213> ORGANISM: Artificial Sequence
<220> FEATURE:
<223> OTHER INFORMATION: Affinity matured light chain 4042

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Ile Gly Gln Pro Ala Ser Ile Ser Cys Lys Ser Ser Gln Ser
            35                  40                  45

Leu Leu Tyr Ser Asn Gly Lys Thr Tyr Leu Asn Trp Leu Gln Gln Arg
        50                  55                  60

Pro Gly Gln Ser Pro Lys Arg Leu Ile Tyr Gln Val Ser Lys Leu Asp
65                  70                  75                  80

Pro Gly Ile Pro Asp Arg Phe Ser Gly Ser Gly Ser Glu Thr Asp Phe
                85                  90                  95

Thr Leu Lys Ile Ser Arg Val Glu Ala Glu Asp Leu Gly Ile Tyr Tyr
            100                 105                 110

Cys Met Gln Gly Ala Ser Leu Pro Trp Thr Phe Gly Gly Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 13
<211> LENGTH: 239
<212> TYPE: PRT
<213> ORGANISM: Artificial Sequence
<220> FEATURE:
<223> OTHER INFORMATION: Affinity matured light chain 4043

<400> SEQUENCE: 13

Met Glu Thr Asp Thr Leu Leu Leu Trp Val Leu Leu Leu Trp Val Pro

```
            1               5                   10                  15
        Gly Ser Thr Gly Asp Ile Val Met Thr Gln Thr Pro Leu Ser Leu Ser
                        20                  25                  30

Val Thr Ile Gly Gln Pro Ala Ser Ile Ser Cys Lys Ser Ser Gln Ser
                        35                  40                  45

Leu Leu Tyr Ser Asn Gly Lys Thr Tyr Leu Asn Trp Leu Gln Gln Arg
                        50                  55                  60

Pro Gly Gln Ser Pro Lys Arg Leu Ile Tyr Gln Val Ser Lys Leu Asp
        65                  70                  75                  80

Pro Gly Thr Pro Asp Arg Phe Ser Gly Ser Gly Ser Glu Thr Asp Phe
                            85                  90                  95

Thr Leu Lys Ile Ser Arg Val Glu Ala Glu Asp Leu Gly Ile Tyr Tyr
                        100                 105                 110

Cys Met Gln Gly Ala Ser Val Pro Trp Thr Phe Gly Gly Gly Thr Lys
                        115                 120                 125

Leu Glu Ile Lys Arg Thr Val Ala Ala Pro Ser Val Phe Ile Phe Pro
                        130                 135                 140

Pro Ser Asp Glu Gln Leu Lys Ser Gly Thr Ala Ser Val Val Cys Leu
        145                 150                 155                 160

Leu Asn Asn Phe Tyr Pro Arg Glu Ala Lys Val Gln Trp Lys Val Asp
                            165                 170                 175

Asn Ala Leu Gln Ser Gly Asn Ser Gln Glu Ser Val Thr Glu Gln Asp
                        180                 185                 190

Ser Lys Asp Ser Thr Tyr Ser Leu Ser Ser Thr Leu Thr Leu Ser Lys
                        195                 200                 205

Ala Asp Tyr Glu Lys His Lys Val Tyr Ala Cys Glu Val Thr His Gln
                        210                 215                 220

Gly Leu Ser Ser Pro Val Thr Lys Ser Phe Asn Arg Gly Glu Cys
        225                 230                 235

<210> SEQ ID NO 14
<211> LENGTH: 239
<212> TYPE: PRT
<213> ORGANISM: Artificial Sequence
<220> FEATURE:
<223> OTHER INFORMATION: affinity matured light chain 4069

<400> SEQUENCE: 14

Met Glu Thr Asp Thr Leu Leu Leu Trp Val Leu Leu Leu Trp Val Pro
        1               5                   10                  15

Gly Ser Thr Gly Asp Ile Val Met Thr Gln Thr Pro Leu Ser Leu Ser
                        20                  25                  30

Val Thr Ile Gly Gln Pro Ala Ser Ile Ser Cys Lys Ser Ser Gln Ser
                        35                  40                  45

Leu Leu Tyr Ser Asn Gly Lys Thr Tyr Leu Asn Trp Leu Gln Gln Arg
                        50                  55                  60

Pro Gly Gln Ser Pro Lys Arg Leu Ile Tyr Gln Val Ser Lys Leu Asp
        65                  70                  75                  80

Pro Gly Ile Pro Asp Arg Phe Ser Gly Ser Gly Ser Glu Thr Asp Phe
                            85                  90                  95

Thr Leu Lys Ile Ser Arg Val Glu Ala Glu Asp Leu Gly Ile Tyr Tyr
                        100                 105                 110

Cys Met Gln Gly Thr Tyr Leu Pro Trp Thr Phe Gly Gly Gly Thr Lys
                        115                 120                 125

Leu Glu Ile Lys Arg Thr Val Ala Ala Pro Ser Val Phe Ile Phe Pro
```

```
                130                 135                 140
Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
                210                 215                 220

Gly Leu Ser Ser Pro Val Thr Lys Ser Phe Asn Arg Gly Glu Cys
225                 230                 235

<210> SEQ ID NO 15
<211> LENGTH: 239
<212> TYPE: PRT
<213> ORGANISM: Artificial Sequence
<220> FEATURE:
<223> OTHER INFORMATION: Affinity matured light chain 4070

<400> SEQUENCE: 15

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
                20                  25                  30

Val Thr Ile Gly Gln Pro Ala Ser Ile Ser Cys Lys Ser Ser Gln Ser
                35                  40                  45

Leu Leu Tyr Ser Asn Gly Lys Thr Tyr Leu Asn Trp Leu Gln Gln Arg
50                  55                  60

Pro Gly Gln Ser Pro Lys Arg Leu Ile Tyr Gln Val Ser Lys Leu Asp
65                  70                  75                  80

Pro Gly Ile Pro Asp Arg Phe Ser Gly Ser Gly Ser Glu Thr Asp Phe
                85                  90                  95

Thr Leu Lys Ile Ser Arg Val Glu Ala Glu Asp Leu Gly Ile Tyr Tyr
                100                 105                 110

Cys Met Gln Gly Thr Ser Leu Pro Trp Thr Phe Gly Gly Gly Thr Lys
                115                 120                 125

Leu Glu Ile Lys Arg Thr Val Ala Ala Pro Ser Val Phe Ile Phe Pro
                130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
                210                 215                 220

Gly Leu Ser Ser Pro Val Thr Lys Ser Phe Asn Arg Gly Glu Cys
225                 230                 235

<210> SEQ ID NO 16
<211> LENGTH: 239
<212> TYPE: PRT
```

<213> ORGANISM: Artificial Sequence
<220> FEATURE:
<223> OTHER INFORMATION: Affinity matured light chain 4071 (PP6373)

<400> SEQUENCE: 16

```
Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Ile Gly Gln Pro Ala Ser Ile Ser Cys Lys Ser Gln Ser
        35                  40                  45

Leu Leu Tyr Ser Asn Gly Lys Thr Tyr Leu Asn Trp Leu Gln Gln Arg
    50                  55                  60

Pro Gly Gln Ser Pro Lys Arg Leu Ile Tyr Gln Val Ser Lys Leu Asp
65                  70                  75                  80

Pro Gly Ile Pro Asp Arg Phe Ser Gly Ser Gly Ser Glu Thr Asp Phe
                85                  90                  95

Thr Leu Lys Ile Ser Arg Val Glu Ala Glu Asp Leu Gly Ile Tyr Tyr
            100                 105                 110

Cys Met Gln Gly Ser Ser Leu Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 17
<211> LENGTH: 479
<212> TYPE: PRT
<213> ORGANISM: Artificial Sequence
<220> FEATURE:
<223> OTHER INFORMATION: PP6373 single chain

<400> SEQUENCE: 17

```
Glu Val Lys Phe Glu Glu Ser Gly Gly Gly Leu Val Gln Pro Gly Gly
1               5                   10                  15

Ser Ile Lys Leu Ser Cys Ala Ala Ser Gly Val Thr Phe Ser Glu Ala
            20                  25                  30

Trp Met Asp Trp Val Arg Gln Ser Pro Glu Lys Gly Leu Glu Trp Val
        35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Thr Glu Asp Thr Gly Ile Tyr
                85                  90                  95
```

-continued

Tyr Cys Thr Gly Ala Met Asp Tyr Trp Gly Gln Gly Thr Ser Val Thr
            100                 105                 110

Val Ser Ser Gly Ser Thr Gly Gly Gly Ser Gly Gly Gly Ser
    115                 120                 125

Gly Gly Gly Ser Asp Ile Val Met Thr Gln Thr Pro Leu Ser Leu
130                 135                 140

Ser Val Thr Ile Gly Gln Pro Ala Ser Ile Ser Cys Lys Ser Ser Gln
145                 150                 155                 160

Ser Leu Leu Tyr Ser Asn Gly Lys Thr Tyr Leu Asn Trp Leu Gln Gln
                165                 170                 175

Arg Pro Gly Gln Ser Pro Lys Arg Leu Ile Tyr Gln Val Ser Lys Leu
            180                 185                 190

Asp Pro Gly Ile Pro Asp Arg Phe Ser Gly Ser Gly Ser Glu Thr Asp
            195                 200                 205

Phe Thr Leu Lys Ile Ser Arg Val Glu Ala Glu Asp Leu Gly Ile Tyr
210                 215                 220

Tyr Cys Met Gln Gly Ser Ser Leu Pro Trp Thr Phe Gly Gly Gly Thr
225                 230                 235                 240

Lys Leu Glu Ile Lys Ile Ser Ala Met Val Arg Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 18
<211> LENGTH: 476
<212> TYPE: PRT
<213> ORGANISM: Artificial Sequence
<220> FEATURE:
<223> OTHER INFORMATION: OKT3 single chain

<400> SEQUENCE: 18

```
Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Thr Pro Gly Lys
                165                 170                 175

Ala Pro Lys Arg Trp Ile Tyr Asp Thr Ser Lys Leu Ala Ser Gly Val
            180                 185                 190

Pro Ser Arg Phe Ser Gly Ser Gly Ser Gly Thr Asp Tyr Thr Phe Thr
        195                 200                 205

Ile Ser Ser Leu Gln Pro Glu Asp Ile Ala Thr Tyr Tyr Cys Gln Gln
    210                 215                 220

Trp Ser Ser Asn Pro Phe Thr Phe Gly Gln Gly Thr Lys Leu Gln Ile
225                 230                 235                 240

Thr Arg Ile Ser Ala Met Val Arg Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
```

```
            405                 410                 415
Glu Asn Asn Tyr Lys Thr Thr Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 19
<211> LENGTH: 479
<212> TYPE: PRT
<213> ORGANISM: Artificial Sequence
<220> FEATURE:
<223> OTHER INFORMATION: PP6373 hole

<400> SEQUENCE: 19

Glu Val Lys Phe Glu Glu Ser Gly Gly Gly Leu Val Gln Pro Gly Gly
1               5                   10                  15

Ser Ile Lys Leu Ser Cys Ala Ala Ser Gly Val Thr Phe Ser Glu Ala
            20                  25                  30

Trp Met Asp Trp Val Arg Gln Ser Pro Glu Lys Gly Leu Glu Trp Val
        35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Thr Glu Asp Thr Gly Ile Tyr
                85                  90                  95

Tyr Cys Thr Gly Ala Met Asp Tyr Trp Gly Gln Gly Thr Ser Val Thr
            100                 105                 110

Val Ser Ser Gly Ser Thr Gly Gly Gly Ser Gly Gly Gly Ser
            115                 120                 125

Gly Gly Gly Gly Ser Asp Ile Val Met Thr Gln Thr Pro Leu Ser Leu
130                 135                 140

Ser Val Thr Ile Gly Gln Pro Ala Ser Ile Ser Cys Lys Ser Ser Gln
145                 150                 155                 160

Ser Leu Leu Tyr Ser Asn Gly Lys Thr Tyr Leu Asn Trp Leu Gln Gln
                165                 170                 175

Arg Pro Gly Gln Ser Pro Lys Arg Leu Ile Tyr Gln Val Ser Lys Leu
            180                 185                 190

Asp Pro Gly Ile Pro Asp Arg Phe Ser Gly Ser Gly Ser Glu Thr Asp
        195                 200                 205

Phe Thr Leu Lys Ile Ser Arg Val Glu Ala Glu Asp Leu Gly Ile Tyr
    210                 215                 220

Tyr Cys Met Gln Gly Ser Ser Leu Pro Trp Thr Phe Gly Gly Gly Thr
225                 230                 235                 240

Lys Leu Glu Ile Lys Ile Ser Ala Met Val Arg Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
```

```
            290                 295                 300
Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Thr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 20
<211> LENGTH: 479
<212> TYPE: PRT
<213> ORGANISM: Artificial Sequence
<220> FEATURE:
<223> OTHER INFORMATION: PP6373 knob

<400> SEQUENCE: 20

Glu Val Lys Phe Glu Ser Gly Gly Gly Leu Val Gln Pro Gly Gly
1               5                   10                  15

Ser Ile Lys Leu Ser Cys Ala Ala Ser Gly Val Thr Phe Ser Glu Ala
                20                  25                  30

Trp Met Asp Trp Val Arg Gln Ser Pro Glu Lys Gly Leu Glu Trp Val
            35                  40                  45

Ala Glu Ile Arg Asp Lys Pro Asn Ser Tyr Val Thr Tyr Tyr Ala Glu
        50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Thr Glu Asp Thr Gly Ile Tyr
                85                  90                  95

Tyr Cys Thr Gly Ala Met Asp Tyr Trp Gly Gln Gly Thr Ser Val Thr
            100                 105                 110

Val Ser Ser Gly Ser Thr Gly Gly Gly Ser Gly Gly Gly Ser
        115                 120                 125

Gly Gly Gly Gly Ser Asp Ile Val Met Thr Gln Thr Pro Leu Ser Leu
    130                 135                 140

Ser Val Thr Ile Gly Gln Pro Ala Ser Ile Ser Cys Lys Ser Ser Gln
145                 150                 155                 160

Ser Leu Leu Tyr Ser Asn Gly Lys Thr Tyr Leu Asn Trp Leu Gln Gln
                165                 170                 175

Arg Pro Gly Gln Ser Pro Lys Arg Leu Ile Tyr Gln Val Ser Lys Leu
```

```
                180             185             190
Asp Pro Gly Ile Pro Asp Arg Phe Ser Gly Ser Gly Ser Glu Thr Asp
                195             200             205

Phe Thr Leu Lys Ile Ser Arg Val Glu Ala Glu Asp Leu Gly Ile Tyr
        210             215             220

Tyr Cys Met Gln Gly Ser Ser Leu Pro Trp Thr Phe Gly Gly Gly Thr
225             230             235             240

Lys Leu Glu Ile Lys Ile Ser Ala Met Val Arg Ser Asp Lys Thr His
                245             250             255

Thr Cys Pro Pro Cys Pro Ala Pro Glu Leu Leu Gly Gly Pro Ser Val
            260             265             270

Phe Leu Phe Pro Pro Lys Pro Lys Asp Thr Leu Met Ile Ser Arg Thr
        275             280             285

Pro Glu Val Thr Cys Val Val Asp Val Ser His Glu Asp Pro Glu
    290             295             300

Val Lys Phe Asn Trp Tyr Val Asp Gly Val Glu Val His Asn Ala Lys
305             310             315             320

Thr Lys Pro Arg Glu Glu Gln Tyr Asn Ser Thr Tyr Arg Val Val Ser
                325             330             335

Val Leu Thr Val Leu His Gln Asp Trp Leu Asn Gly Lys Glu Tyr Lys
            340             345             350

Cys Lys Val Ser Asn Lys Ala Leu Pro Ala Pro Ile Glu Lys Thr Ile
        355             360             365

Ser Lys Ala Lys Gly Gln Pro Arg Glu Pro Gln Val Tyr Thr Leu Pro
    370             375             380

Pro Ser Arg Glu Glu Met Thr Lys Asn Gln Val Ser Leu Tyr Cys Leu
385             390             395             400

Val Lys Gly Phe Tyr Pro Ser Asp Ile Ala Val Glu Trp Glu Ser Asn
                405             410             415

Gly Gln Pro Glu Asn Asn Tyr Lys Thr Thr Pro Pro Val Leu Asp Ser
            420             425             430

Asp Gly Ser Phe Phe Leu Tyr Ser Lys Leu Thr Val Asp Lys Ser Arg
        435             440             445

Trp Gln Gln Gly Asn Val Phe Ser Cys Ser Val Met His Glu Ala Leu
    450             455             460

His Asn His Tyr Thr Gln Lys Ser Leu Ser Leu Ser Pro Gly Lys
465             470             475

<210> SEQ ID NO 21
<211> LENGTH: 476
<212> TYPE: PRT
<213> ORGANISM: Artificial Sequence
<220> FEATURE:
<223> OTHER INFORMATION: OKT3 hole

<400> SEQUENCE: 21

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
```

```
                 65                  70                  75                  80

Leu Gln Met Asp Ser Leu Arg Pro Glu Asp Thr Ala Val Tyr Tyr Cys
                     85                  90                  95

Ala Arg Tyr Tyr Asp Asp His Tyr Cys Leu Asp Tyr Trp Gly Gln Gly
                100                 105                 110

Thr Thr Leu Thr Val Ser Ser Gly Gly Gly Gly Ser Gly Gly Gly
            115                 120                 125

Gly Ser Gly Gly Gly Gly Ser Asp Ile Gln Met Thr Gln Ser Pro Ser
        130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Thr Pro Gly Lys
                165                 170                 175

Ala Pro Lys Arg Trp Ile Tyr Asp Thr Ser Lys Leu Ala Ser Gly Val
            180                 185                 190

Pro Ser Arg Phe Ser Gly Ser Gly Ser Gly Thr Asp Tyr Thr Phe Thr
        195                 200                 205

Ile Ser Ser Leu Gln Pro Glu Asp Ile Ala Thr Tyr Tyr Cys Gln Gln
    210                 215                 220

Trp Ser Ser Asn Pro Phe Thr Phe Gly Gln Gly Thr Lys Leu Gln Ile
225                 230                 235                 240

Thr Arg Ile Ser Ala Met Val Arg Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Thr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 22
```

```
<211> LENGTH: 476
<212> TYPE: PRT
<213> ORGANISM: Artificial Sequence
<220> FEATURE:
<223> OTHER INFORMATION: OKT3 knob

<400> SEQUENCE: 22

Gln Val Gln Leu Val Gln Ser Gly Gly Gly Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Thr Pro Gly Lys
                165                 170                 175

Ala Pro Lys Arg Trp Ile Tyr Asp Thr Ser Lys Leu Ala Ser Gly Val
            180                 185                 190

Pro Ser Arg Phe Ser Gly Ser Gly Ser Gly Thr Asp Tyr Thr Phe Thr
        195                 200                 205

Ile Ser Ser Leu Gln Pro Glu Asp Ile Ala Thr Tyr Tyr Cys Gln Gln
    210                 215                 220

Trp Ser Ser Asn Pro Phe Thr Phe Gly Gln Gly Thr Lys Leu Gln Ile
225                 230                 235                 240

Thr Arg Ile Ser Ala Met Val Arg Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380
```

```
Glu Met Thr Lys Asn Gln Val Ser Leu Tyr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
        420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475
```

<210> SEQ ID NO 23
<211> LENGTH: 736
<212> TYPE: PRT
<213> ORGANISM: Artificial Sequence
<220> FEATURE:
<223> OTHER INFORMATION: PP6373-OKT3

<400> SEQUENCE: 23

```
Glu Val Lys Phe Glu Glu Ser Gly Gly Gly Leu Val Gln Pro Gly Gly
1               5                   10                  15

Ser Ile Lys Leu Ser Cys Ala Ala Ser Gly Val Thr Phe Ser Glu Ala
            20                  25                  30

Trp Met Asp Trp Val Arg Gln Ser Pro Glu Lys Gly Leu Glu Trp Val
        35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Thr Glu Asp Thr Gly Ile Tyr
                85                  90                  95

Tyr Cys Thr Gly Ala Met Asp Tyr Trp Gly Gln Gly Thr Ser Val Thr
            100                 105                 110

Val Ser Ser Gly Ser Thr Gly Gly Gly Ser Gly Gly Gly Gly Ser
        115                 120                 125

Gly Gly Gly Gly Ser Asp Ile Val Met Thr Gln Thr Pro Leu Ser Leu
    130                 135                 140

Ser Val Thr Ile Gly Gln Pro Ala Ser Ile Ser Cys Lys Ser Ser Gln
145                 150                 155                 160

Ser Leu Leu Tyr Ser Asn Gly Lys Thr Tyr Leu Asn Trp Leu Gln Gln
                165                 170                 175

Arg Pro Gly Gln Ser Pro Lys Arg Leu Ile Tyr Gln Val Ser Lys Leu
            180                 185                 190

Asp Pro Gly Ile Pro Asp Arg Phe Ser Gly Ser Gly Ser Glu Thr Asp
        195                 200                 205

Phe Thr Leu Lys Ile Ser Arg Val Glu Ala Glu Asp Leu Gly Ile Tyr
    210                 215                 220

Tyr Cys Met Gln Gly Ser Ser Leu Pro Trp Thr Phe Gly Gly Gly Thr
225                 230                 235                 240

Lys Leu Glu Ile Lys Gly Gly Gly Gly Ser Gly Gly Gly Gly Ser Gly
                245                 250                 255

Gly Gly Gly Ser Gln Val Gln Leu Val Gln Ser Gly Gly Gly Val Val
            260                 265                 270
```

```
Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Val Lys Asp Arg Phe Thr Ile Ser Thr Asp Lys Ser Lys
                325                 330                 335

Ser Thr Ala Phe Leu Gln Met Asp Ser Leu Arg Pro Glu Asp Thr Ala
            340                 345                 350

Val Tyr Tyr Cys Ala Arg Tyr Tyr Asp Asp His Tyr Cys Leu Asp Tyr
        355                 360                 365

Trp Gly Gln Gly Thr Thr Leu Thr Val Ser Ser Thr Gly Gly Gly Gly
    370                 375                 380

Ser Gly Gly Gly Gly Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Asn Trp Tyr Gln Gln
            420                 425                 430

Thr Pro Gly Lys Ala Pro Lys Arg Trp Ile Tyr Asp Thr Ser Lys Leu
        435                 440                 445

Ala Ser Gly Val Pro Ser Arg Phe Ser Gly Ser Gly Ser Gly Thr Asp
    450                 455                 460

Tyr Thr Phe Thr Ile Ser Ser Leu Gln Pro Glu Asp Ile Ala Thr Tyr
465                 470                 475                 480

Tyr Cys Gln Gln Trp Ser Ser Asn Pro Phe Thr Phe Gly Gln Gly Thr
                485                 490                 495

Lys Leu Gln Ile Thr Arg Ile Ser Ala Met Val Arg Ser Asp Lys Thr
            500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
    530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
                565                 570                 575

Lys Thr Lys Pro Arg Glu Glu Gln Tyr Asn Ser Thr Tyr Arg Val Val
            580                 585                 590

Ser Val Leu Thr Val Leu His Gln Asp Trp Leu Asn Gly Lys Glu Tyr
        595                 600                 605

Lys Cys Lys Val Ser Asn Lys Ala Leu Pro Ala Pro Ile Glu Lys Thr
    610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
                645                 650                 655

Leu Val Lys Gly Phe Tyr Pro Ser Asp Ile Ala Val Glu Trp Glu Ser
            660                 665                 670

Asn Gly Gln Pro Glu Asn Asn Tyr Lys Thr Thr Pro Pro Val Leu Asp
        675                 680                 685
```

```
Ser Asp Gly Ser Phe Phe Leu Tyr Ser Lys Leu Thr Val Asp Lys Ser
    690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
                725                 730                 735
```

<210> SEQ ID NO 24
<211> LENGTH: 736
<212> TYPE: PRT
<213> ORGANISM: Artificial Sequence
<220> FEATURE:
<223> OTHER INFORMATION: OKT3-PP6373

<400> SEQUENCE: 24

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Thr Pro Gly Lys
                165                 170                 175

Ala Pro Lys Arg Trp Ile Tyr Asp Thr Ser Lys Leu Ala Ser Gly Val
            180                 185                 190

Pro Ser Arg Phe Ser Gly Ser Gly Ser Gly Thr Asp Tyr Thr Phe Thr
        195                 200                 205

Ile Ser Ser Leu Gln Pro Glu Asp Ile Ala Thr Tyr Tyr Cys Gln Gln
    210                 215                 220

Trp Ser Ser Asn Pro Phe Thr Phe Gly Gln Gly Thr Lys Leu Gln Ile
225                 230                 235                 240

Thr Arg Gly Gly Gly Gly Ser Gly Gly Gly Gly Ser Gly Gly Gly Gly
                245                 250                 255

Ser Glu Val Lys Phe Glu Glu Ser Gly Gly Gly Leu Val Gln Pro Gly
            260                 265                 270

Gly Ser Ile Lys Leu Ser Cys Ala Ala Ser Gly Val Thr Phe Ser Glu
        275                 280                 285

Ala Trp Met Asp Trp Val Arg Gln Ser Pro Glu Lys Gly Leu Glu Trp
    290                 295                 300

Val Ala Glu Ile Arg Asp Lys Pro Asn Ser Tyr Val Thr Tyr Tyr Ala
305                 310                 315                 320
```

-continued

```
Glu Ser Val Lys Gly Arg Phe Thr Ile Ser Arg Asp Asp Ser Lys Ser
            325                 330                 335

Arg Val Tyr Leu Gln Met Asn Asn Leu Arg Thr Glu Asp Thr Gly Ile
        340                 345                 350

Tyr Tyr Cys Thr Gly Ala Met Asp Tyr Trp Gly Gln Gly Thr Ser Val
        355                 360                 365

Thr Val Ser Ser Gly Ser Thr Gly Gly Gly Ser Gly Gly Gly Gly
        370                 375                 380

Ser Gly Gly Gly Ser Asp Ile Val Met Thr Gln Thr Pro Leu Ser
385                 390                 395                 400

Leu Ser Val Thr Ile Gly Gln Pro Ala Ser Ile Ser Cys Lys Ser Ser
            405                 410                 415

Gln Ser Leu Leu Tyr Ser Asn Gly Lys Thr Tyr Leu Asn Trp Leu Gln
            420                 425                 430

Gln Arg Pro Gly Gln Ser Pro Lys Arg Leu Ile Tyr Gln Val Ser Lys
        435                 440                 445

Leu Asp Pro Gly Ile Pro Asp Arg Phe Ser Gly Ser Gly Ser Glu Thr
    450                 455                 460

Asp Phe Thr Leu Lys Ile Ser Arg Val Glu Ala Glu Asp Leu Gly Ile
465                 470                 475                 480

Tyr Tyr Cys Met Gln Gly Ser Ser Leu Pro Trp Thr Phe Gly Gly Gly
            485                 490                 495

Thr Lys Leu Glu Ile Lys Ile Ser Ala Met Val Arg Ser Asp Lys Thr
            500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
    530                 535                 540

Thr Pro Glu Val Thr Cys Val Val Asp Val Ser His Glu Asp Pro
545                 550                 555                 560

Glu Val Lys Phe Asn Trp Tyr Val Asp Gly Val Glu Val His Asn Ala
            565                 570                 575

Lys Thr Lys Pro Arg Glu Glu Gln Tyr Asn Ser Thr Tyr Arg Val Val
        580                 585                 590

Ser Val Leu Thr Val Leu His Gln Asp Trp Leu Asn Gly Lys Glu Tyr
        595                 600                 605

Lys Cys Lys Val Ser Asn Lys Ala Leu Pro Ala Pro Ile Glu Lys Thr
    610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
            645                 650                 655

Leu Val Lys Gly Phe Tyr Pro Ser Asp Ile Ala Val Glu Trp Glu Ser
        660                 665                 670

Asn Gly Gln Pro Glu Asn Asn Tyr Lys Thr Thr Pro Pro Val Leu Asp
        675                 680                 685

Ser Asp Gly Ser Phe Phe Leu Tyr Ser Lys Leu Thr Val Asp Lys Ser
    690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
            725                 730                 735
```

```
<210> SEQ ID NO 25
<211> LENGTH: 671
<212> TYPE: PRT
<213> ORGANISM: Artificial Sequence
<220> FEATURE:
<223> OTHER INFORMATION: VL6373-CL-VHOKT3-CH1-Fc

<400> SEQUENCE: 25

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Gln Gln Arg Pro Gly Gln Ser
        35                  40                  45

Pro Lys Arg Leu Ile Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Ile Tyr Tyr Cys Met Gln Gly
                85                  90                  95

Ser Ser Leu Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gln Val
    210                 215                 220

Gln Leu Val Gln Ser Gly Gly Gly Val Val Gln Pro Gly Arg Ser Leu
225                 230                 235                 240

Arg Leu Ser Cys Lys Ala Ser Gly Tyr Thr Phe Thr Arg Tyr Thr Met
                245                 250                 255

His Trp Val Arg Gln Ala Pro Gly Lys Gly Leu Glu Trp Ile Gly Tyr
            260                 265                 270

Ile Asn Pro Ser Arg Gly Tyr Thr Asn Tyr Asn Gln Lys Val Lys Asp
        275                 280                 285

Arg Phe Thr Ile Ser Thr Asp Lys Ser Lys Ser Thr Ala Phe Leu Gln
    290                 295                 300

Met Asp Ser Leu Arg Pro Glu Asp Thr Ala Val Tyr Tyr Cys Ala Arg
305                 310                 315                 320

Tyr Tyr Asp Asp His Tyr Cys Leu Asp Tyr Trp Gly Gln Gly Thr Thr
                325                 330                 335

Leu Thr Val Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
```

```
                    370                 375                 380
Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Leu Leu Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 26
<211> LENGTH: 218
<212> TYPE: PRT
<213> ORGANISM: Artificial Sequence
<220> FEATURE:
<223> OTHER INFORMATION: VH6373-CH1

<400> SEQUENCE: 26

Glu Val Lys Phe Glu Glu Ser Gly Gly Gly Leu Val Gln Pro Gly Gly
1               5                   10                  15

Ser Ile Lys Leu Ser Cys Ala Ala Ser Gly Val Thr Phe Ser Glu Ala
            20                  25                  30

Trp Met Asp Trp Val Arg Gln Ser Pro Glu Lys Gly Leu Glu Trp Val
        35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Arg
```

```
                65                  70                  75                  80
Val Tyr Leu Gln Met Asn Asn Leu Arg Thr Glu Asp Thr Gly Ile Tyr
                    85                  90                  95

Tyr Cys Thr Gly Ala Met Asp Tyr Trp Gly Gln Gly Thr Ser Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys
210                 215

<210> SEQ ID NO 27
<211> LENGTH: 214
<212> TYPE: PRT
<213> ORGANISM: Artificial Sequence
<220> FEATURE:
<223> OTHER INFORMATION: VLOKT3-CL

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
```

-continued

```
<210> SEQ ID NO 28
<211> LENGTH: 522
<212> TYPE: PRT
<213> ORGANISM: Artificial Sequence
<220> FEATURE:
<223> OTHER INFORMATION: anti-CD24IgV-sc

<400> SEQUENCE: 28
```

| Glu | Val | Lys | Phe | Glu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ile | Lys | Leu | Ser | Cys | Ala | Ala | Ser | Gly | Val | Thr | Phe | Ser | Glu | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Met | Asp | Trp | Val | Arg | Gln | Ser | Pro | Glu | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Glu | Ile | Arg | Asp | Lys | Pro | Asn | Ser | Tyr | Val | Thr | Tyr | Tyr | Ala | Glu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Val | Lys | Gly | Arg | Phe | Thr | Ile | Ser | Arg | Asp | Asp | Ser | Lys | Ser | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Tyr | Leu | Gln | Met | Asn | Asn | Leu | Arg | Thr | Glu | Asp | Thr | Gly | Ile | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Cys | Thr | Gly | Ala | Met | Asp | Tyr | Trp | Gly | Gln | Gly | Thr | Ser | Val | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Ser | Ser | Gly | Ser | Thr | Gly | Gly | Gly | Ser | Gly | Gly | Gly | Gly | Ser |
|-----|-----|-----|-----|-----|-----|-----|-----|-----|-----|-----|-----|-----|-----|-----|
|     |     |     | 115 |     |     |     | 120 |     |     |     |     | 125 |     |     |

| Gly | Gly | Gly | Gly | Ser | Asp | Ile | Val | Met | Thr | Gln | Thr | Pro | Leu | Ser | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Val | Thr | Ile | Gly | Gln | Pro | Ala | Ser | Ile | Ser | Cys | Lys | Ser | Ser | Gln |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Leu | Leu | Tyr | Ser | Asn | Gly | Lys | Thr | Tyr | Leu | Asn | Trp | Leu | Gln | Gln |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Arg | Pro | Gly | Gln | Ser | Pro | Lys | Arg | Leu | Ile | Tyr | Gln | Val | Ser | Lys | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Asp | Pro | Gly | Ile | Pro | Asp | Arg | Phe | Ser | Gly | Ser | Gly | Ser | Glu | Thr | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Phe | Thr | Leu | Lys | Ile | Ser | Arg | Val | Glu | Ala | Glu | Asp | Leu | Gly | Ile | Tyr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Tyr | Cys | Met | Gln | Gly | Ser | Ser | Leu | Pro | Trp | Thr | Phe | Gly | Gly | Gly | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Lys | Leu | Glu | Ile | Lys | Arg | Ser | Val | Thr | Val | Ser | Ser | Ala | Ala | Ala | Ile |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Glu | Val | Met | Tyr | Pro | Pro | Pro | Tyr | Leu | Asp | Asn | Glu | Lys | Ser | Asn | Gly |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Thr | Ile | Ile | His | Val | Lys | Gly | Lys | His | Leu | Cys | Pro | Ser | Pro | Leu | Phe |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Pro | Gly | Pro | Ser | Lys | Pro | Phe | Trp | Val | Leu | Val | Val | Val | Gly | Gly | Val |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Ala | Cys | Tyr | Ser | Leu | Leu | Val | Thr | Val | Ala | Phe | Ile | Ile | Phe | Trp |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Arg | Ser | Lys | Arg | Ser | Arg | Leu | Leu | His | Ser | Asp | Tyr | Met | Asn | Met |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Thr | Pro | Arg | Arg | Pro | Gly | Pro | Thr | Arg | Lys | His | Tyr | Gln | Pro | Tyr | Ala |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Pro | Pro | Arg | Asp | Phe | Ala | Ala | Tyr | Arg | Ser | Arg | Phe | Ser | Val | Val | Lys |
|-----|-----|-----|-----|-----|-----|-----|-----|-----|-----|-----|-----|-----|-----|-----|-----|

```
                355                 360                 365
Arg Gly Arg Lys Lys Leu Leu Tyr Ile Phe Lys Gln Pro Phe Met Arg
    370                 375                 380

Pro Val Gln Thr Thr Gln Glu Asp Gly Cys Ser Cys Arg Phe Pro
385                 390                 395                 400

Glu Glu Glu Glu Gly Cys Glu Leu Arg Val Lys Phe Ser Arg Ser
                405                 410                 415

Ala Asp Ala Pro Ala Tyr Gln Gln Gly Gln Asn Gln Leu Tyr Asn Glu
                420                 425                 430

Leu Asn Leu Gly Arg Arg Glu Glu Tyr Asp Val Leu Asp Lys Arg Arg
            435                 440                 445

Gly Arg Asp Pro Glu Met Gly Gly Lys Pro Gln Arg Arg Lys Asn Pro
        450                 455                 460

Gln Glu Gly Leu Tyr Asn Glu Leu Gln Lys Asp Lys Met Ala Glu Ala
465                 470                 475                 480

Tyr Ser Glu Ile Gly Met Lys Gly Glu Arg Arg Arg Gly Lys Gly His
                485                 490                 495

Asp Gly Leu Tyr Gln Gly Leu Ser Thr Ala Thr Lys Asp Thr Tyr Asp
                500                 505                 510

Ala Leu His Met Gln Ala Leu Pro Pro Arg
            515                 520
```

```
<210> SEQ ID NO 29
<211> LENGTH: 115
<212> TYPE: PRT
<213> ORGANISM: Artificial Sequence
<220> FEATURE:
<223> OTHER INFORMATION: Hu Onc-VHv1

<400> SEQUENCE: 29

Glu Val Gln Phe Val Glu Ser Gly Gly Gly Leu Val Gln Pro Gly Gly
1               5                   10                  15

Ser Leu Lys Leu Ser Cys Ala Ala Ser Gly Val Thr Phe Ser Glu Ala
            20                  25                  30

Trp Met Asp Trp Val Arg Gln Ala Ser Gly Lys Gly Leu Glu Trp Val
        35                  40                  45

Gly Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Gly Ala Met Asp Tyr Trp Gly Gln Gly Thr Leu Val Thr
            100                 105                 110

Val Ser Ser
        115

<210> SEQ ID NO 30
<211> LENGTH: 115
<212> TYPE: PRT
<213> ORGANISM: Artificial Sequence
<220> FEATURE:
<223> OTHER INFORMATION: Hu Onc-VHv2

<400> SEQUENCE: 30

Glu Val Gln Phe Val Glu Ser Gly Gly Gly Leu Val Gln Pro Gly Gly
1               5                   10                  15
```

Ser Leu Lys Leu Ser Cys Ala Ala Ser Gly Val Thr Phe Ser Glu Ala
            20                  25                  30

Trp Met Asp Trp Val Arg Gln Ala Ser Gly Lys Gly Leu Glu Trp Val
            35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Gly Ala Met Asp Tyr Trp Gly Gln Gly Thr Leu Val Thr
            100                 105                 110

Val Ser Ser
        115

<210> SEQ ID NO 31
<211> LENGTH: 115
<212> TYPE: PRT
<213> ORGANISM: Artificial Sequence
<220> FEATURE:
<223> OTHER INFORMATION: Hu Onc-VHv3

<400> SEQUENCE: 31

Glu Val Gln Phe Val Glu Ser Gly Gly Gly Leu Val Gln Pro Gly Gly
1               5                   10                  15

Ser Leu Lys Leu Ser Cys Ala Ala Ser Gly Val Thr Phe Ser Glu Ala
            20                  25                  30

Trp Met Asp Trp Val Arg Gln Ala Ser Gly Lys Gly Leu Glu Trp Val
            35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Ile Tyr
                85                  90                  95

Tyr Cys Thr Gly Ala Met Asp Tyr Trp Gly Gln Gly Thr Leu Val Thr
            100                 105                 110

Val Ser Ser
        115

<210> SEQ ID NO 32
<211> LENGTH: 115
<212> TYPE: PRT
<213> ORGANISM: Artificial Sequence
<220> FEATURE:
<223> OTHER INFORMATION: Hu Onc-VHv4

<400> SEQUENCE: 32

Glu Val Gln Phe Val Glu Ser Gly Gly Gly Leu Val Gln Pro Gly Gly
1               5                   10                  15

Ser Leu Lys Leu Ser Cys Ala Ala Ser Gly Val Thr Phe Ser Glu Ala
            20                  25                  30

Trp Met Asp Trp Val Arg Gln Ala Ser Gly Lys Gly Leu Glu Trp Val
            35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Lys Thr Glu Asp Thr Ala Ile Tyr
                85                  90                  95

Tyr Cys Thr Gly Ala Met Asp Tyr Trp Gly Gln Gly Thr Leu Val Thr
            100                 105                 110

Val Ser Ser
        115

<210> SEQ ID NO 33
<211> LENGTH: 113
<212> TYPE: PRT
<213> ORGANISM: Artificial Sequence
<220> FEATURE:
<223> OTHER INFORMATION: Hu Onc-VLv1

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Gln Val Ser Lys Leu Asp Pro Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Ser Leu Pro Trp Thr Phe Gly Gly Gly Thr Lys Val Glu Ile Lys
            100                 105                 110

Arg

<210> SEQ ID NO 34
<211> LENGTH: 113
<212> TYPE: PRT
<213> ORGANISM: Artificial Sequence
<220> FEATURE:
<223> OTHER INFORMATION: Hu Onc-VLv2

<400> SEQUENCE: 34

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Gln Val Ser Lys Leu Asp Pro Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Ser Leu Pro Trp Thr Phe Gly Gly Gly Thr Lys Val Glu Ile Lys
            100                 105                 110

Arg

<210> SEQ ID NO 35
<211> LENGTH: 113

```
<212> TYPE: PRT
<213> ORGANISM: Artificial Sequence
<220> FEATURE:
<223> OTHER INFORMATION: Hu Onc-VLv3

<400> SEQUENCE: 35

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Lys Arg Leu Ile Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ser Ser Leu Pro Trp Thr Phe Gly Gly Gly Thr Lys Val Glu Ile Lys
            100                 105                 110

Arg

<210> SEQ ID NO 36
<211> LENGTH: 113
<212> TYPE: PRT
<213> ORGANISM: Artificial Sequence
<220> FEATURE:
<223> OTHER INFORMATION: Hu Onc-VLv4

<400> SEQUENCE: 36

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Lys Arg Leu Ile Tyr Gln Val Ser Lys Leu Asp Pro Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Ser Leu Pro Trp Thr Phe Gly Gly Gly Thr Lys Val Glu Ile Lys
            100                 105                 110

Arg

<210> SEQ ID NO 37
<211> LENGTH: 671
<212> TYPE: PRT
<213> ORGANISM: Artificial Sequence
<220> FEATURE:
<223> OTHER INFORMATION: VL6373-L3-CL-VHOKT3-CH1-Fc

<400> SEQUENCE: 37

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30
```

```
Asn Gly Lys Thr Tyr Leu Asn Trp Leu Leu Gln Lys Pro Gly Gln Ser
         35                  40                  45

Pro Lys Arg Leu Ile Tyr Gln Val Ser Lys Leu Asp Pro Gly Ile Pro
 50                  55                  60

Asp Arg Phe Ser Gly Ser Gly Ser Glu Thr Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Ser Ser Leu Pro Trp Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Ser Gly Gln Val
210                 215                 220

Gln Leu Val Gln Ser Gly Gly Val Val Gln Pro Gly Arg Ser Leu
225                 230                 235                 240

Arg Leu Ser Cys Lys Ala Ser Gly Tyr Thr Phe Thr Arg Tyr Thr Met
                245                 250                 255

His Trp Val Arg Gln Ala Pro Gly Lys Gly Leu Glu Trp Ile Gly Tyr
                260                 265                 270

Ile Asn Pro Ser Arg Gly Tyr Thr Asn Tyr Asn Gln Lys Val Lys Asp
        275                 280                 285

Arg Phe Thr Ile Ser Thr Asp Lys Ser Lys Ser Thr Ala Phe Leu Gln
290                 295                 300

Met Asp Ser Leu Arg Pro Glu Asp Thr Ala Val Tyr Tyr Cys Ala Arg
305                 310                 315                 320

Tyr Tyr Asp Asp His Tyr Cys Leu Asp Tyr Trp Gly Gln Gly Thr Thr
                325                 330                 335

Leu Thr Val Ser Ser Ala Ser Thr Lys Gly Pro Ser Val Phe Pro Leu
                340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
                420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Leu Leu Gly Gly Pro Ser Val
```

```
                450             455             460
Phe Leu Phe Pro Pro Lys Pro Lys Asp Thr Leu Met Ile Ser Arg Thr
465                 470                 475                 480

Pro Glu Val Thr Cys Val Val Asp Val Ser His Glu Asp Pro Glu
            485                 490                 495

Val Lys Phe Asn Trp Tyr Val Asp Gly Val Glu Val His Asn Ala Lys
                500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
            530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
            610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 38
<211> LENGTH: 218
<212> TYPE: PRT
<213> ORGANISM: Artificial Sequence
<220> FEATURE:
<223> OTHER INFORMATION: VH6373-H3-CH1

<400> SEQUENCE: 38

Glu Val Gln Phe Val Glu Ser Gly Gly Gly Leu Val Gln Pro Gly Gly
1               5                   10                  15

Ser Leu Lys Leu Ser Cys Ala Ala Ser Gly Val Thr Phe Ser Glu Ala
            20                  25                  30

Trp Met Asp Trp Val Arg Gln Ala Ser Gly Lys Gly Leu Glu Trp Val
        35                  40                  45

Ala Glu Ile Arg Asp Lys Pro Asn Ser Tyr Val Thr Tyr Tyr Ala Glu
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Ile Tyr
                85                  90                  95

Tyr Cys Thr Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
```

```
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
    210                 215

<210> SEQ ID NO 39
<211> LENGTH: 693
<212> TYPE: PRT
<213> ORGANISM: Artificial Sequence
<220> FEATURE:
<223> OTHER INFORMATION: WBP4002-A1 (mutate D to A on Fc)

<400> SEQUENCE: 39

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Thr Pro Leu Ser
            20                  25                  30

Leu Ser Val Thr Ile Gly Gln Pro Ala Ser Ile Ser Cys Lys Ser Ser
        35                  40                  45

Gln Ser Leu Leu Tyr Ser Asn Gly Lys Thr Tyr Leu Asn Trp Leu Leu
    50                  55                  60

Gln Lys Pro Gly Gln Ser Pro Lys Arg Leu Ile Tyr Gln Val Ser Lys
65                  70                  75                  80

Leu Asp Pro Gly Ile Pro Asp Arg Phe Ser Gly Ser Gly Ser Glu Thr
                85                  90                  95

Asp Phe Thr Leu Lys Ile Ser Arg Val Glu Ala Glu Asp Val Gly Ile
            100                 105                 110

Tyr Tyr Cys Met Gln Gly Ser Ser Leu Pro Trp Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys Gly Ser Gly Gln Val Gln Leu Val Gln Ser Gly Gly Gly Val Val
                245                 250                 255

Gln Pro Gly Arg Ser Leu Arg Leu Ser Cys Lys Ala Ser Gly Tyr Thr
            260                 265                 270

Phe Thr Arg Tyr Thr Met His Trp Val Arg Gln Ala Pro Gly Lys Gly
        275                 280                 285

Leu Glu Trp Ile Gly Tyr Ile Asn Pro Ser Arg Gly Tyr Thr Asn Tyr
```

```
                290                 295                 300
Asn Gln Lys Val Lys Asp Arg Phe Thr Ile Ser Thr Asp Lys Ser Lys
305                 310                 315                 320

Ser Thr Ala Phe Leu Gln Met Asp Ser Leu Arg Pro Glu Asp Thr Ala
                325                 330                 335

Val Tyr Tyr Cys Ala Arg Tyr Tyr Asp His Tyr Cys Leu Asp Tyr
                340                 345                 350

Trp Gly Gln Gly Thr Thr Leu Thr Val Ser Ser Ala Ser Thr Lys Gly
                355                 360                 365

Pro Ser Val Phe Pro Leu Ala Pro Ser Ser Lys Ser Thr Ser Gly Gly
370                 375                 380

Thr Ala Ala Leu Gly Cys Leu Val Lys Asp Tyr Phe Pro Glu Pro Val
385                 390                 395                 400

Thr Val Ser Trp Asn Ser Gly Ala Leu Thr Ser Gly Val His Thr Phe
                405                 410                 415

Pro Ala Val Leu Gln Ser Ser Gly Leu Tyr Ser Leu Ser Ser Val Val
                420                 425                 430

Thr Val Pro Ser Ser Ser Leu Gly Thr Gln Thr Tyr Ile Cys Asn Val
                435                 440                 445

Asn His Lys Pro Ser Asn Thr Lys Val Asp Lys Lys Val Glu Pro Lys
                450                 455                 460

Ser Cys Asp Lys Thr His Thr Cys Pro Pro Cys Pro Ala Pro Glu Leu
465                 470                 475                 480

Leu Gly Gly Pro Ser Val Phe Leu Phe Pro Pro Lys Pro Lys Asp Thr
                485                 490                 495

Leu Met Ile Ser Arg Thr Pro Glu Val Thr Cys Val Val Val Ala Val
                500                 505                 510

Ser His Glu Asp Pro Glu Val Lys Phe Asn Trp Tyr Val Asp Gly Val
                515                 520                 525

Glu Val His Asn Ala Lys Thr Lys Pro Arg Glu Glu Gln Tyr Asn Ser
530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
                565                 570                 575

Pro Ile Glu Lys Thr Ile Ser Lys Ala Lys Gly Gln Pro Arg Glu Pro
                580                 585                 590

Gln Val Tyr Thr Leu Pro Pro Ser Arg Glu Glu Met Thr Lys Asn Gln
                595                 600                 605

Val Ser Leu Thr Cys Leu Val Lys Gly Phe Tyr Pro Ser Asp Ile Ala
                610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
                645                 650                 655

Thr Val Asp Lys Ser Arg Trp Gln Gln Gly Asn Val Phe Ser Cys Ser
                660                 665                 670

Val Met His Glu Ala Leu His Asn His Tyr Thr Gln Lys Ser Leu Ser
                675                 680                 685

Leu Ser Pro Gly Lys
    690

<210> SEQ ID NO 40
```

<211> LENGTH: 237
<212> TYPE: PRT
<213> ORGANISM: Artificial Sequence
<220> FEATURE:
<223> OTHER INFORMATION: WBP4002-A2

<400> SEQUENCE: 40

```
Met Glu Phe Gly Leu Ser Trp Leu Phe Leu Val Ala Ile Leu Lys Gly
1               5                   10                  15

Val Gln Cys Glu Val Gln Phe Val Glu Ser Gly Gly Gly Leu Val Gln
            20                  25                  30

Pro Gly Gly Ser Leu Lys Leu Ser Cys Ala Ala Ser Gly Val Thr Phe
        35                  40                  45

Ser Glu Ala Trp Met Asp Trp Val Arg Gln Ala Ser Gly Lys Gly Leu
    50                  55                  60

Glu Trp Val Ala Glu Ile Arg Asp Lys Pro Asn Ser Tyr Val Thr Tyr
65                  70                  75                  80

Tyr Ala Glu Ser Val Lys Gly Arg Phe Thr Ile Ser Arg Asp Asp Ser
                85                  90                  95

Lys Ser Thr Ala Tyr Leu Gln Met Asn Ser Leu Lys Thr Glu Asp Thr
            100                 105                 110

Ala Ile Tyr Tyr Cys Thr Gly Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys
225                 230                 235
```

<210> SEQ ID NO 41
<211> LENGTH: 235
<212> TYPE: PRT
<213> ORGANISM: Artificial Sequence
<220> FEATURE:
<223> OTHER INFORMATION: WBP4002-A3 (delete extra R between VLQKT3 and CL)

<400> SEQUENCE: 41

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Ser Ser Val Ser Tyr Met Asn Trp Tyr Gln Gln Thr Pro Gly Lys Ala
    50                  55                  60

Pro Lys Arg Trp Ile Tyr Asp Thr Ser Lys Leu Ala Ser Gly Val Pro
65                  70                  75                  80
```

```
Ser Arg Phe Ser Gly Ser Gly Ser Gly Thr Asp Tyr Thr Phe Thr Ile
             85                  90                  95

Ser Ser Leu Gln Pro Glu Asp Ile Ala Thr Tyr Tyr Cys Gln Gln Trp
            100                 105                 110

Ser Ser Asn Pro Phe Thr Phe Gly Gln Gly Thr Lys Leu Gln Ile Thr
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 42
<211> LENGTH: 30
<212> TYPE: PRT
<213> ORGANISM: Artificial Sequence
<220> FEATURE:
<223> OTHER INFORMATION: CD24 mapping epitope

<400> SEQUENCE: 42

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 43
<211> LENGTH: 10
<212> TYPE: PRT
<213> ORGANISM: Artificial Sequence
<220> FEATURE:
<223> OTHER INFORMATION: Mapping peptide 1

<400> SEQUENCE: 43

Ser Glu Thr Thr Thr Gly Thr Ser Ser Asn
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Mapping peptide 2

<400> SEQUENCE: 44

Gly Thr Ser Ser Asn Ser Ser Gln Ser Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Mapping peptide 3
```

```
<400> SEQUENCE: 45

Ser Ser Gln Ser Thr Ser Asn Ser Gly Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Mapping peptide 4

<400> SEQUENCE: 46

Ser Asn Ser Gly Leu Ala Pro Asn Pro Thr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Mapping peptide 5

<400> SEQUENCE: 47

Ala Pro Asn Pro Thr Asn Ala Thr Thr Lys
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Minimal binding peptide

<400> SEQUENCE: 48

Ser Asn Ser Gly Leu Ala Pro Asn
1               5

<210> SEQ ID NO 49
<211> LENGTH: 15
<212> TYPE: PRT
<213> ORGANISM: Artificial Sequence
<220> FEATURE:
<223> OTHER INFORMATION: Flexible linker

<400> SEQUENCE: 49

Gly Gly Gly Gly Ser Gly Gly Gly Gly Ser Gly Gly Gly Gly Ser
1               5                   10                  15
```